US012570664B2

(12) United States Patent
Mohamed et al.

(10) Patent No.: US 12,570,664 B2
(45) Date of Patent: Mar. 10, 2026

(54) PROCESSES FOR THE PREPARATION OF (3S,4R)-3-ETHYL-4-(3H-IMIDAZO[1,2-α] PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

(71) Applicant: AbbVie Inc., North Chicago, IL (US)

(72) Inventors: Mohamed-Eslam F. Mohamed, Gurnee, IL (US); Ahmed A. Othman, Libertyville, IL (US); Ben Klünder, Ludwigshafen (DE); Heidi S. Camp, Winnetka, IL (US); Robert J. Padley, Highland Park, IL (US); Jeffrey W. Voss, Hudson, MA (US); Aileen L. Pangan, La Grange, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 19/182,366

(22) Filed: Apr. 17, 2025

(65) Prior Publication Data

US 2025/0250277 A1 Aug. 7, 2025

Related U.S. Application Data

(63) Continuation-in-part of application No. 19/174,569, filed on Apr. 9, 2025, which is a continuation of application No. 18/812,217, filed on Aug. 22, 2024, now abandoned, which is a continuation of application No. 18/533,564, filed on Dec. 8, 2023, now abandoned, which is a continuation of application No. 18/137,804, filed on Apr. 21, 2023, now abandoned, which is a continuation of application No. 17/902,690, filed on Sep. 2, 2022, now abandoned, which is a continuation of application No. 17/184,194, filed on Feb. 24, 2021, now abandoned, which is a continuation of application No. 16/656,237, filed on Oct. 17, 2019, now abandoned, which is a continuation of application No. 15/891,012, filed on Feb. 7, 2018, now abandoned, which is a continuation of application No. 15/295,561, filed on Oct. 17, 2016, now abandoned.

(60) Provisional application No. 63/635,277, filed on Apr. 17, 2024, provisional application No. 62/352,380, filed on Jun. 20, 2016, provisional application No. 62/301,537, filed on Feb. 29, 2016, provisional application No. 62/267,672, filed on Dec. 15, 2015, provisional application No. 62/242,797, filed on Oct. 16, 2015.

(51) Int. Cl.
C07D 487/14 (2006.01)
A61K 9/00 (2006.01)
A61K 31/4985 (2006.01)
A61K 47/02 (2006.01)
A61K 47/12 (2006.01)
A61K 47/38 (2006.01)
C07D 487/04 (2006.01)

(52) U.S. Cl.
CPC .......... *C07D 487/14* (2013.01); *A61K 9/0053* (2013.01); *A61K 31/4985* (2013.01); *A61K 47/02* (2013.01); *A61K 47/12* (2013.01); *A61K 47/38* (2013.01); *C07D 487/04* (2013.01); *C07B 2200/13* (2013.01)

(58) Field of Classification Search
CPC .. C07D 487/14; C07D 487/04; A61K 9/0053; A61K 31/4985; A61K 47/02; A61K 47/12; A61K 47/38; C07B 2200/13
USPC ......................................................... 514/250
See application file for complete search history.

(56) References Cited

U.S. PATENT DOCUMENTS

| | | | |
|---|---|---|---|
| 3,119,742 A | 1/1964 | Macdonnell et al. |
| 3,492,397 A | 1/1970 | Lieberman et al. |
| 3,538,214 A | 11/1970 | Shoop et al. |
| 4,060,598 A | 11/1977 | Groppenbacher et al. |
| 4,173,626 A | 11/1979 | Dempski et al. |
| 12,365,689 B2 | 7/2025 | Mohamed et al. |
| 2008/0038347 A1 | 2/2008 | Eisenreich et al. |
| 2009/0169618 A1 | 7/2009 | Ari-Pardo et al. |
| 2012/0231083 A1 | 9/2012 | Carley et al. |
| 2023/0233555 A1 | 7/2023 | Mohamed |
| 2024/0317770 A1 | 9/2024 | Allian et al. |
| 2024/0376115 A1 | 11/2024 | Allian et al. |
| 2025/0163071 A1 | 5/2025 | Allian et al. |

FOREIGN PATENT DOCUMENTS

WO WO-2011068881 A1 * 6/2011 ............. A61P 37/08

OTHER PUBLICATIONS

Vasculitis [online], [retrieved on Jul. 31, 2025] Retrieved from the Internet, URL: https://www.nhlbi.nih.gov/health/vasculitis.html (Year: 2025).*
Center for Drug Evaluation and Research, "Clinical Pharmacology and Biopharmaceutics Review(s)", Application No. 211675Orig1s000, 138 pages (Sep. 12, 2019).

(Continued)

*Primary Examiner* — Kristin A Vajda
(74) *Attorney, Agent, or Firm* — WOMBLE BOND DICKINSON (US) LLP; Danielle L. Herritt; Scott R. Breining

(57) ABSTRACT
The present disclosure relates to processes for preparing (3S,4R)-3-ethyl-4-(3H-imidazo[1,2-a]pyrrolo[2,3-e] pyrazin-8-yl)-N-(2,2,2-trifluoroethyl)pyrrolidine-1-carboxamide, solid state forms thereof, and corresponding pharmaceutical compositions, methods of treatment (including treatment of rheumatoid arthritis and vasculitis), kits, methods of synthesis, and products-by-process. In various aspects, provided are methods for treating giant cell arteritis (GCA).

15 Claims, 27 Drawing Sheets

(56) References Cited

OTHER PUBLICATIONS

AbbVie, Press Release on Jan. 8, 2018, "AbbVie's Upadacitinib Granted Breatkthrough Therapy Designation from the U.S. Food and Drug Administration for Atopic Dermatitis", accessed at http://news.abbvie.com/2018-01-08-AbbVies-Upadacitinib-Granted-Breakthrough-Therapy-Designation-from-the-U-S-Food-and-Drug-Administration-for-Atopic-Dermatitis, 2 pages.

* cited by examiner

FIG. 1A

ACR RESPONSE AT WEEK 12

PLACEBO
3 mg BID
6 mg BID
12 mg BID
18 mg BID

PATIENTS ACHIEVING DAS28(CRP) ≤3.2 OR <2.6 AT WEEK 12 IN SUBJECTS WITH ACTIVE RHEUMATOID ARTHRITIS AND PRIOR INADEQUATE RESPONSE OR INTOLERANCE TO AN ANTI-TNF BIOLOGICAL AGENT

MEAN HEMOGLOBIN CHANGE FROM BASELINE OVER TIME (ALL SUBJECTS WITH ACTIVE RHEUMATOID ARTHRITIS AND PRIOR INADEQUATE RESPONSE OR INTOLERANCE TO AN ANTI-TNF BIOLOGIC AGENT WITH hsCRP>ULN)

MEAN HEMOGLOBIN LEVELS OVER TIME (ALL SUBJECTS WITH ACTIVE RHEUMATOID ARTHRITIS AND PRIOR INADEQUATE RESPONSE OR INTOLERANCE TO AN ANTI-TNF BIOLOGIC AGENT)

FIG. 5A

PATIENT DISPOSITION

FIG. 5B

ACR20 RESPONSES OVER TIME (NRI ANALYSIS) IN
SUBJECTS WITH ACTIVE RHEUMATOID ARTHRITIS
AND INADEQUATE RESPONSE TO METHOTREXATE

FIG. 9A

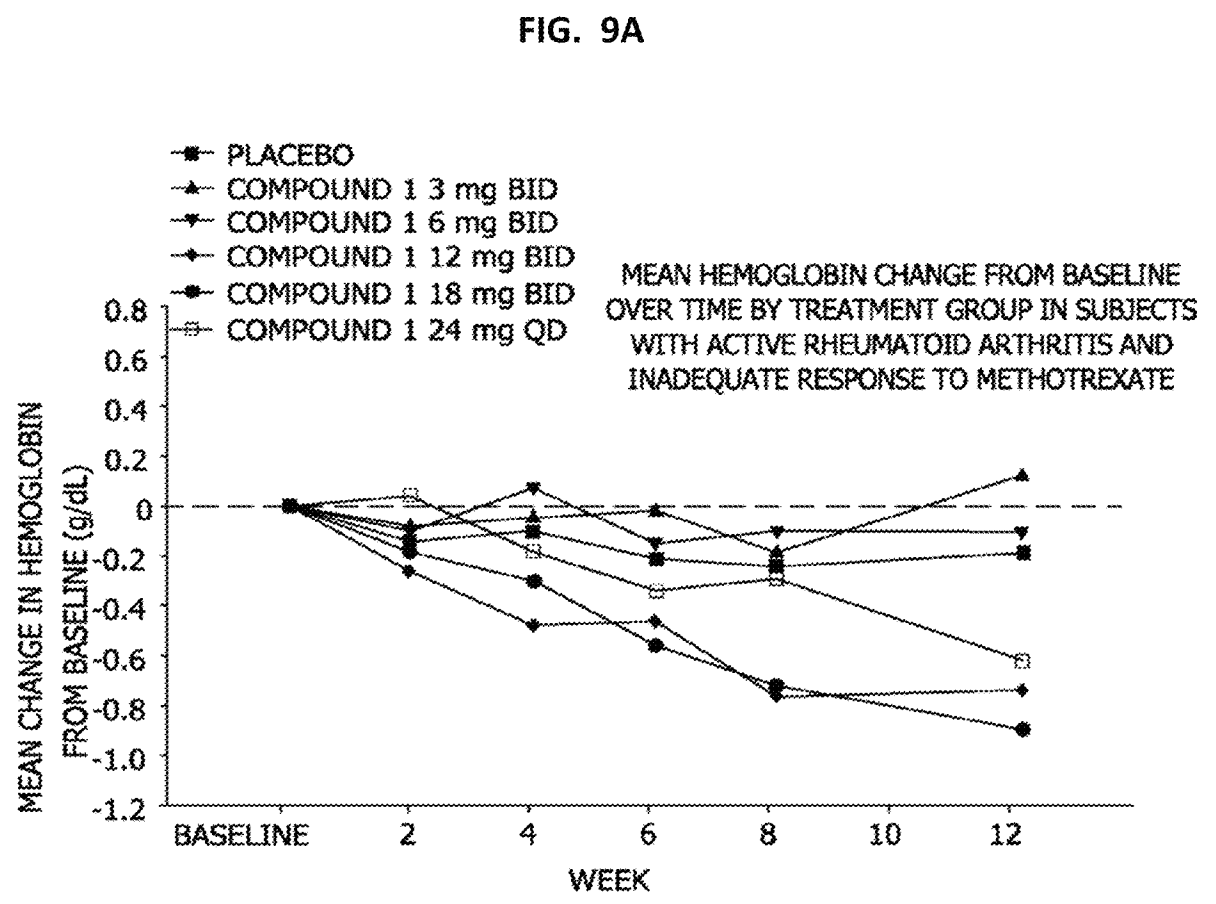

MEAN HEMOGLOBIN CHANGE FROM BASELINE OVER TIME BY TREATMENT GROUP IN SUBJECTS WITH ACTIVE RHEUMATOID ARTHRITIS AND INADEQUATE RESPONSE TO METHOTREXATE

- PLACEBO
- COMPOUND 1 3 mg BID
- COMPOUND 1 6 mg BID
- COMPOUND 1 12 mg BID
- COMPOUND 1 18 mg BID
- COMPOUND 1 24 mg QD

WEEK

MEAN CHANGE IN HEMOGLOBIN FROM BASELINE (g/dL)

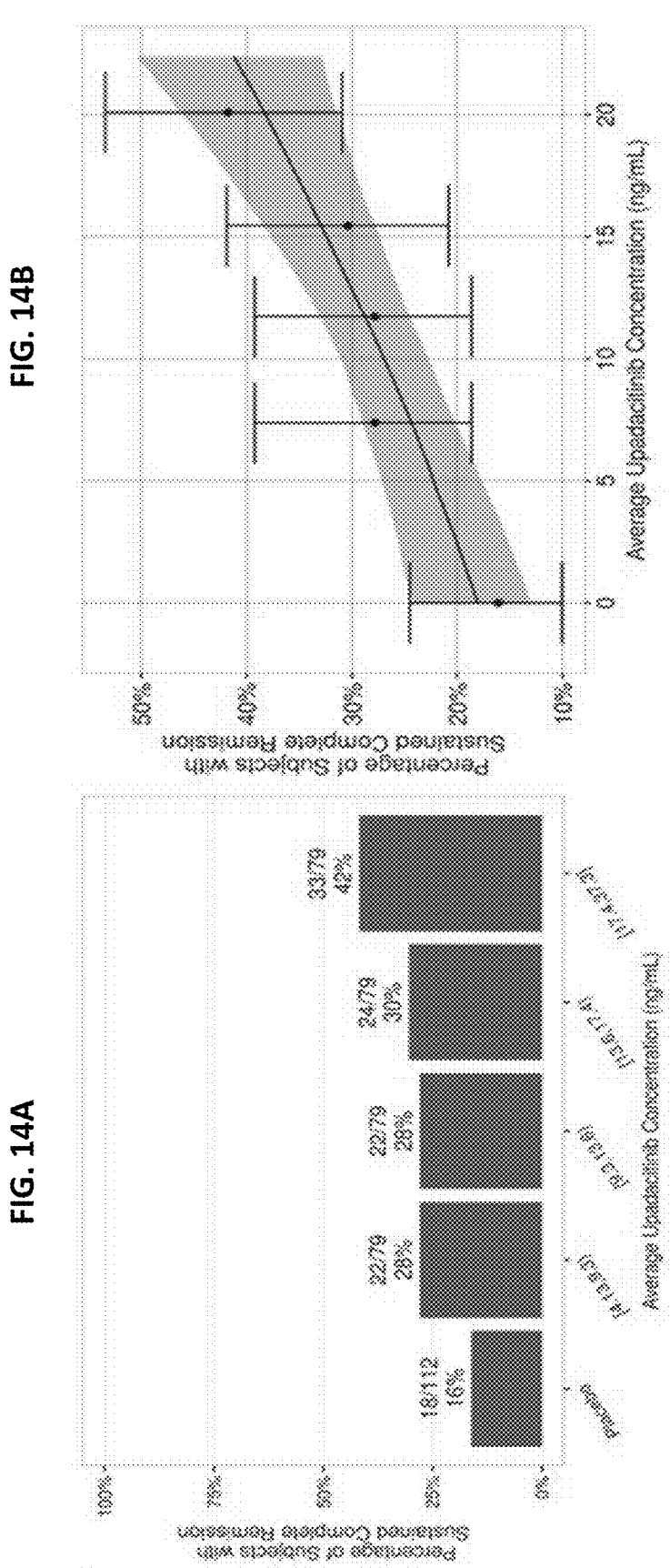

PROCESSES FOR THE PREPARATION OF (3S,4R)-3-ETHYL-4-(3H-IMIDAZO[1,2-α] PYRROLO[2,3-E]-PYRAZIN-8-YL)-N-(2,2,2-TRIFLUOROETHYL) PYRROLIDINE-1-CARBOXAMIDE AND SOLID STATE FORMS THEREOF

CROSS-REFERENCE TO RELATED APPLICATIONS

This application is a continuation-in-part of U.S. patent application Ser. No. 19/174,569, filed Apr. 9, 2025, which is a continuation of U.S. patent application Ser. No. 18/812, 217, filed Aug. 22, 2024; which is a continuation of U.S. patent application Ser. No. 18/533,564, filed Dec. 8, 2023; which is a continuation of U.S. patent application Ser. No. 18/137,804, filed Apr. 21, 2023; which is a continuation of U.S. patent application Ser. No. 17/902,690, filed Sep. 2, 2022; which is a continuation of U.S. patent application Ser. No. 17/184,194, filed Feb. 24, 2021; which is a continuation of U.S. patent application Ser. No. 16/656,237, filed Oct. 17, 2019; which is a continuation of U.S. patent application Ser. No. 15/891,012, filed Feb. 7, 2018; which is a continuation of U.S. patent application Ser. No. 15/295,561, filed Oct. 17, 2016; and which claims the benefit of U.S. Provisional Application No. 62/242,797, filed Oct. 16, 2015; and claims the benefit of U.S. Provisional Application No. 62/267,672, filed Dec. 15, 2015; and claims the benefit of U.S. Provisional Application No. 62/301,537, filed Feb. 29, 2016; and claims the benefit of U.S. Provisional Application No. 62/352,380, filed Jun. 20, 2016; this application also claims the benefit of U.S. Provisional Application No. 63/635,277, filed Apr. 17, 2024, all of which are herein incorporated by reference in their entirety.

FIELD OF THE INVENTION

The present disclosure relates to: (a) processes for the preparation of (3S,4R)-3-ethyl-4-(3H-imidazo[1,2-a]pyrrolo [2,3-e]pyrazin-8-yl)-N-(2,2,2-trifluoroethyl)pyrrolidine-1-carboxamide (referred to herein as "Compound 1"), (b) intermediates used in the preparation of Compound 1 and processes for preparing the intermediates; (c) solid-state forms of Compound 1, (d) pharmaceutical compositions comprising one or more solid-state forms of Compound 1, and, optionally, one or more additional therapeutic agents; (e) methods of treating Janus kinase-associated conditions (including rheumatoid arthritis) by administering one or more solid-state forms of Compound 1 to a subject in need thereof; (f) kits comprising a first pharmaceutical composition comprising a solid-state form of Compound 1, and, optionally, a second pharmaceutical composition comprising one or more additional therapeutic agents; (g) methods for the preparation of solid-state forms of Compound 1; and (h) solid-state forms of Compound 1 prepared in accordance with such methods. The present disclosure further relates to methods for treating vasculitis (e.g., giant cell arteritis (GCA)) with the JAK1 selective inhibitor upadacitinib.

BACKGROUND OF THE INVENTION (3S,4R)-3-ethyl-4-(3H-imidazo[1,2-a]pyrrolo[2,3-e] pyrazin-8-yl)-N-(2,2,2-trifluoroethyl)pyrrolidine-1-carbox-amide ("Compound 1"; "upadacitinib") was first disclosed in International Application WO2011/068881A1, which is herein incorporated by reference in its entirety. The compound has activity as a Janus kinase ("JAK") inhibitor, particularly as a JAK-1 inhibitor. Clinical trials are ongoing to evaluate the use of the compounds to treat rheumatoid arthritis and several other indications.

Vasculitis is a group of diseases whose main feature is inflammation of blood vessels. Giant cell arteritis (GCA), a type of vasculitis, mostly affects the arteries in the head, and especially those in the temples. The most common symptoms of giant cell arteritis are pain and tenderness, often severe, that usually affects both temples, and may also include headaches, scalp tenderness, jaw pain, fever, fatigue, weight loss, and vision problems. Left untreated, GCA can lead to blindness. The cause of GCA is unknown, but is believed to be of an autoimmune nature, and certain genetic and environmental factors are believed to increase susceptibility. GCA most commonly affects Caucasians in Northern Europe or of Scandinavian descent, with most patients developing signs and symptoms between the ages of 70 and 80. Women are about twice as likely to develop the condition than men, and about 50 percent of people with giant cell arteritis also have polymyalgia rheumatica (PMR).

First-line treatment for GCA is long-term administration of corticosteroids. Generally, patients taper off from corticosteroids completely after one to two years, and are susceptible to relapses following the discontinuation of treatment.

For reasons including patient convenience and compliance, particularly in long-term treatment, and to reduce or eliminate the need for corticosteroids, it would be desirable to provide an efficacious oral therapeutic for the treatment of GCA.

SUMMARY OF THE INVENTION

In one aspect, the present disclosure relates to methods of treating a JAK-associated condition (such as rheumatoid arthritis) in a human subject suffering from or susceptible to such a condition comprising administering to the subject a therapeutically effective amount of a solid-state form of Compound 1. In another aspect, the disclosure relates to a pharmaceutical composition comprising a therapeutically effective amount of a solid-state form of Compound 1 as described in the present disclosure, for use in treatment of a JAK-associated condition (such as rheumatoid arthritis) in a subject, particularly in a human subject suffering from or susceptible to the condition.

In another aspect, the present disclosure relates to methods of treating rheumatoid arthritis, wherein the term "rheumatoid arthritis" includes juvenile rheumatoid arthritis, juvenile idiopathic arthritis, ankylosing spondylitis disease, Sjogren's syndrome, psoriatic arthritis.

In another aspect, the present disclosure relates to methods of treating inflammatory bowel disease, wherein the term "inflammatory bowel disease" includes Crohn's disease, pediatric Crohn's disease and ulcerative colitis.

In another aspect, the present disclosure relates to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis and systemic lupus erythematosus in a human subject suffering from or susceptible to such a condition, the method comprising administering to the subject a therapeutically effective amount a solid-state form of Compound 1. In another aspect, the disclosure relates to a pharmaceutical composition comprising a therapeutically effective amount of a solid-state form of Compound 1 as described in the present disclosure, for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition.

In another aspect, the present disclosure relates to methods of treating a JAK-associated condition (such as rheumatoid arthritis) in a human subject suffering from or susceptible to such a condition comprising administering to the subject a solid-state form of Compound 1, in combination with one or more additional therapeutic agents (e.g., a therapeutic agent for treating rheumatoid arthritis that is not a JAK inhibitor). In another aspect, the disclosure relates to a pharmaceutical composition comprising a solid-state form of Compound 1, as described in the present disclosure, in combination with one or more additional therapeutic agents (e.g., a therapeutic agent for treating rheumatoid arthritis that is not a JAK inhibitor), for use in treatment of a JAK-associated condition (such as rheumatoid arthritis) in a subject, particularly in a human subject suffering from or susceptible to the condition.

In another aspect, the present disclosure relates to a method of treating moderate to severely active rheumatoid arthritis, the method comprising administering a therapeutically effective amount of Compound 1 in one or more forms as disclosed herein to a subject suffering from or susceptible to the condition. In a particular aspect, such a method may comprise administering 7.5 mg once daily or 15 mg once daily, or 30 mg once daily, or 45 mg once daily of the Compound 1, in one or more forms as disclosed herein, to the subject. In this or another particular aspect, the subject may be administered the Compound 1 in Freebase Form C. In this or yet another particular aspect, the subject may have an inadequate response to methotrexate. In this or yet another particular aspect, the subject may have an inadequate response to biologics medicines approved for rheumatoid arthritis. In this or yet another particular aspect, the subject may have not previously been administered biologics medicines approved for rheumatoid arthritis.

In another aspect, the present disclosure relates to a method of treating an adult subject having moderate to severely active rheumatoid arthritis, the method comprising administering to the subject: a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent. In one embodiment, the present disclosure is directed to a pharmaceutical composition for use in treating an adult subject having moderate to severely active rheumatoid arthritis, the use comprising administering the pharmaceutical composition to the subject, wherein the pharmaceutical composition comprises a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

In another embodiment, the present disclosure relates to a method of treating structural damage associated with rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened. In one embodiment, the disclosure relates to a pharmaceutical composition for use in treating structural damage associated with rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened.

In another aspect, the disclosure is directed to a method of treating moderate to severely active rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating. In one embodiment, the disclosure is directed to a pharmaceutical composition for use in treating moderate to severely active rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating.

In another aspect, the disclosure is directed to a method of reducing signs and symptoms of rheumatoid arthritis in an adult subject with moderately to severely active rheumatoid arthritis, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent. In one embodiment, the disclosure is directed to a pharmaceutical composition for use in reducing signs and symptoms of rheumatoid arthritis in an adult subject with moderately to severely active rheumatoid arthritis, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of Compound 1 freebase, or a crystalline hydrate of Compound 1 in an amount sufficient to deliver to the subject about 7.5 mg, or about 15 mg, or about 30 mg, or about 45 mg of Compound 1 freebase equivalent. In this or another particular aspect, the hydrate may be a hemihydrate. In this or another aspect, the hemihydrate may be Freebase Hydrate Form C. In this or yet another particular aspect, the subject may have an inadequate response or tolerance to one or more disease-modifying antirheumatic drugs (DMARDS), such as methotrexate. In this or yet another particular aspect, the subject may have not previously been administered DMARDS. In this or yet another particular aspect, the subject may further be administered one or more DMARD.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg per day of Compound 1 freebase or a crystalline hydrate of Compound 1 in an amount sufficient to deliver to the subject about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 15 mg per day of Compound 1 freebase or a crystalline hydrate of Compound 1 in an amount sufficient to deliver to the subject about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 30 mg per day of Compound 1 freebase or a crystalline hydrate of Compound 1 in an amount sufficient to deliver to the subject about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 45 mg per day of Compound 1 freebase or a crystalline hydrate of Compound 1 in an amount sufficient to deliver to the subject about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of a crystalline hydrate of Compound 1. In this or another particular aspect, the hydrate may be a hemihydrate. In this or another aspect, the hemihydrate may be Freebase Hydrate Form C.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of a crystalline hydrate of Compound 1, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of a crystalline hydrate of Compound 1, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg, or about 15 mg, or about 30 mg, or about 45 mg per day of a crystalline hydrate of Compound 1. In this or another particular aspect, the hydrate may be a hemihydrate. In this or another aspect, the hemihydrate may be Freebase Hydrate Form C.

In another aspect, the present disclosure is directed to an extended-release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

The present disclosure is further directed to a method for treating vasculitis with the selective JAK1 inhibitor, upadacitinib. The treatment method generally comprises administering to a patient in need thereof a therapeutically effective amount of upadacitinib.

Accordingly, in one aspect is provided a method of treating vasculitis in a human patient in need thereof, the method comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg.

In some embodiments, the patient is an adult.

In some embodiments, the patient had inadequately responded to treatment with oral corticosteroids.

In some embodiments, the method further comprises administering an oral corticosteroid to the patient.

In some embodiments, the therapeutically effective amount of Compound 1 is administered as 15.4 mg of Freebase Hydrate Form C.

The present disclosure is further directed to a method for treating giant cell arteritis (GCA) with the selective JAK1 inhibitor, upadacitinib. The treatment method generally comprises administering to a patient in need thereof a therapeutically effective amount of upadacitinib.

Accordingly, in one aspect is provided a method of treating GCA in a patient, the method comprising orally administering once daily to the patient 15 mg of upadacitinib.

In another aspect is provided a method of inducing remission of GCA in a patient, the method comprising orally administering once daily to the patient 15 mg of upadacitinib.

In another aspect is provided a method of treating GCA in a patient, the method comprising orally administering once daily to the patient 7.5 mg of upadacitinib.

In another aspect is provided a method of inducing remission of GCA in a patient, the method comprising orally administering once daily to the patient 7.5 mg of upadacitinib.

In some embodiments, the patient achieves remission of GCA 12 weeks following the first daily administration. In some embodiments, the patient achieves sustained remission of GCA from 12 weeks following the first daily administration through 52 weeks after the first daily administration.

In one aspect is provided a method of inducing and sustaining remission of GCA in a patient, the method comprising orally administering once daily to the patient 15 mg of upadacitinib.

In some embodiments, the patient achieves remission of GCA 12 weeks following the first daily administration, and remission is sustained from 12 weeks following the first daily administration through 52 weeks after the first daily administration. In some embodiments, the patient achieves glucocorticoid free sustained remission at week 52 after the first daily administration.

In some embodiments, the patient achieves remission of GCA 12 weeks following the first daily administration and sustains remission of GCA through 52 weeks after the first daily administration.

In one aspect is provided a method of inducing complete remission of GCA in a patient, the method comprising orally administering once daily to the patient 15 mg of upadacitinib.

In some embodiments, the patient achieves complete remission of GCA 12 weeks following the first daily administration. In some embodiments, the patient achieves sustained complete remission of GCA from 12 weeks following the first daily administration through 52 weeks after the first daily administration.

In one aspect is provided a method of inducing and sustaining complete remission of GCA in a patient, the method comprising orally administering once daily to the patient 15 mg of upadacitinib.

In some embodiments, the patient achieves remission of GCA 12 weeks following the first daily administration, and remission is sustained from 12 weeks following the first daily administration through 52 weeks after the first daily administration. In some embodiments, the patient achieves glucocorticoid free sustained complete remission at week 52 after the first daily administration.

In some embodiments, the patient achieves complete remission of GCA 12 weeks following the first daily administration and sustains complete remission of GCA through week 52 after the first daily administration.

In some embodiments, the patient achieves a reduction in cumulative exposure to corticosteroids through week 52 after the first daily administration, relative to a patient that has not been treated with upadacitinib.

In some embodiments, the patient achieves an increase in time to disease flare through week 52 after the first daily administration, relative to a patient that has not been treated with upadacitinib.

In some embodiments, the patient achieves a reduction in a number of disease flares through week 52 after the first daily administration, relative to a patient that has not been treated with upadacitinib.

In some embodiments, the patient achieves, relative to a patient that has not been treated with upadacitinib, one or more of the following:

a positive change from baseline in a 36-item Short Form Quality of Life Questionnaire (SF-36) Physical Component Score (PCS);

a positive change from baseline in a Functional Assessment of Chronic Illness Therapy-Fatigue (FACIT-Fatigue);

a positive change from baseline in an Assessment of Treatment Satisfaction Questionnaire for Medication (TSQM) Patient Global Satisfaction Subscale.

In some embodiments, the patient is currently receiving a tapering course of glucocorticoids.

In some embodiments, the patient is currently receiving at least 20 mg oral corticosteroid once daily at the time of the first daily administration.

In some embodiments, the method further comprises tapering a dose of the oral corticosteroid over a period of 26 weeks.

In some embodiments, the patient has:

a history of erythrocyte sedimentation rate (ESR)>=50 mm/hour or high sensitivity C-reactive protein (hsCRP)/CRP >=1.0 mg/dL;

unequivocal cranial symptoms of GCA, unequivocal symptoms of polymyalgia rheumatica (PMR), or both;

a temporal artery biopsy revealing features of GCA, evidence of large vessel vasculitis by angiography or cross-sectional imaging, or both;

active GCA, either new onset or relapsing, within 8 weeks prior to the first administration; and clinically stable GCA.

In some embodiments, the patient has not received any Janus Kinase (JAK) inhibitor within 4 weeks prior to initiating the method. Examples of JAK inhibitors include, but are not limited to, upadacitinib, tofacitinib, baricitinib, delgocitinib, pacritinib, fedratinib, ritlecitinib, ruxolitinib, and abrocitinib.

In some embodiments, the patient has not received any interleukin-6 (IL-6) inhibitor within 4 weeks prior to initiating the treatment or has not had a disease flare during prior treatment with an IL-6 inhibitor.

In some embodiments, the patient has not received:

anakinra within 1 week prior to initiating the treatment;

methotrexate, hydroxychloroquine, cyclosporine, aza-thioprine, or mycophenolate within 4 weeks prior to initiating the treatment;

greater than or equal to 8 weeks for leflunomide if no elimination procedure was followed; and cell-depleting agents or alkylating agents including cyclo-phosphamide within 6 months prior to initiating the treatment.

In some embodiments, the patient is 50 years of age or older. In some embodiments, the patient is 50 years of age or older with new-onset or relapsing GCA.

In some embodiments, the patient does not have and has not previously had herpes zoster, herpes simplex, or human immunodeficiency virus (HIV).

In some embodiments, the patient does not have active tuberculosis, an active or chronic recurring infection, or active hepatitis B or C.

BRIEF DESCRIPTION OF THE DRAWINGS

Figure 1A:
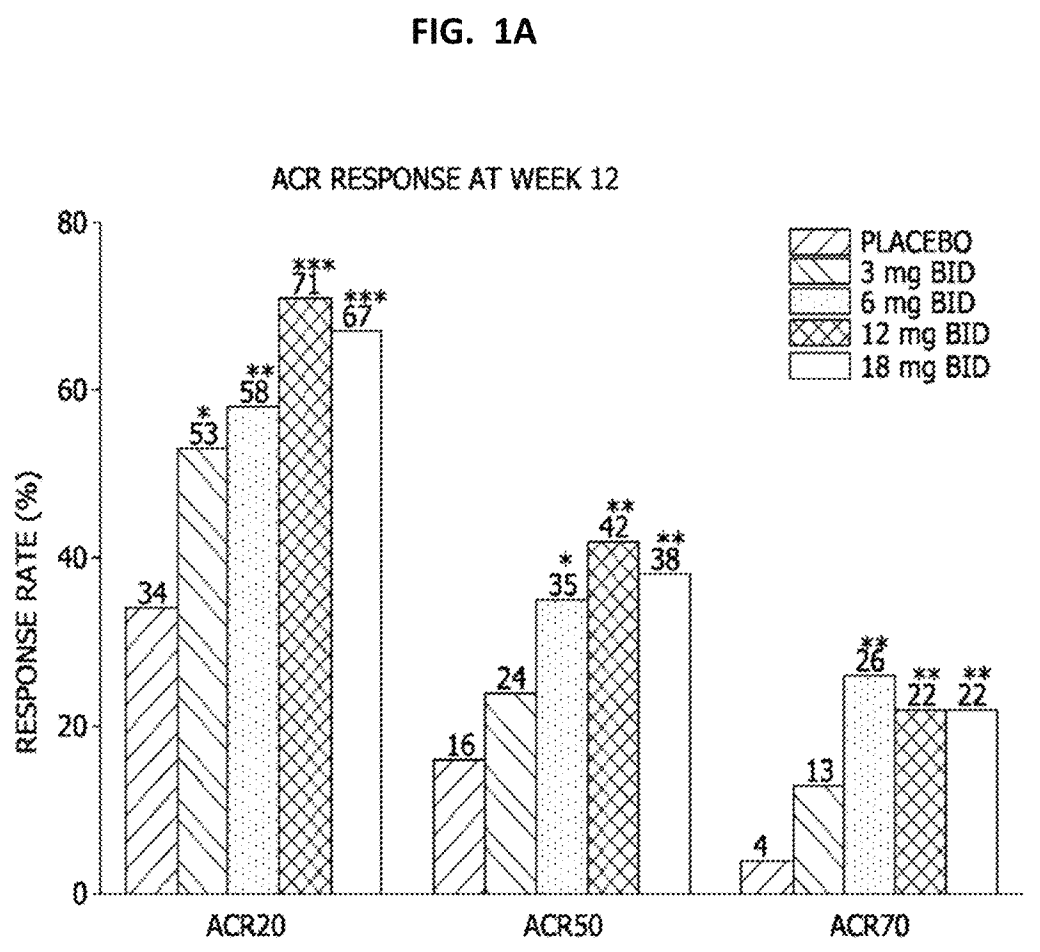

FIG. 1A shows the ACR20, ACR50, and ACR70 response rate at week 12 following administration of placebo or various doses of Compound 1 to subjects with active rheumatoid arthritis and prior inadequate response or intolerance to an anti-TNF biologic agent (*P<0.05;  P<0.01; * P<0.001 relative to placebo; modified intent-to-treat population (NRI)).

FIGS. 5A and 5B show the subject disposition for the study described in Example 33.

FIGS. 9A-9C show the mean change in hemoglobin from baseline over time by treatment group in all subjects (FIG. 9A), subjects with hsCRP≤5 mg/mL at baseline (FIG. 9B), and subjects with hsCRP >5 mg/mL at baseline (FIG. 9C) following administration of placebo or various doses of Compound 1 to subjects with active rheumatoid arthritis and inadequate response to methotrexate (safety population with observed data (no imputation of missing values)).

FIG. 14A is a graphical depiction of the proportion of patients achieving sustained complete remission from week 12 to week 52 in the clinical study of Example 34 (Quartile plot).

FIG. 14B is a graphical depiction of the proportion of patients achieving sustained complete remission from week 12 to week 52 in the clinical study of Example 34 (Logistic regression model).

13

DETAILED DESCRIPTION OF THE INVENTION

Figure 1B:
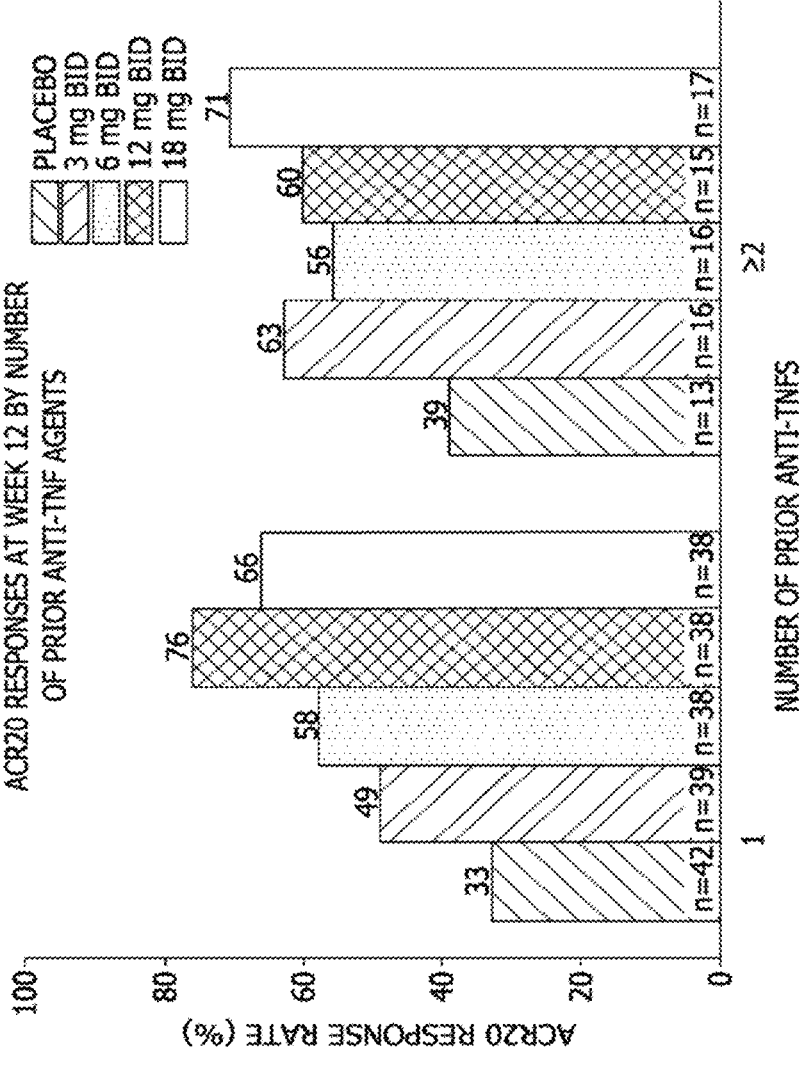
FIG. 1B shows the ACR20 response rate at week 12 in the same population, broken down by number of prior anti-TNF biologic agents.

This written description uses examples to disclose the invention and also to enable any person skilled in the art to practice the invention, including making and using any of the disclosed solid-state forms or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "AUC" refers to the area under the curve. AUC is the definite integral of a curve that describes the variation of a drug concentration in blood plasma as a function of time.

The term "$C_{max}$" refers to the plasma concentration of the referent drug at $T_{max}$, expressed herein as ng/mL, produced by the oral ingestion of a single dose, or indicated number of doses, of the dosage form or pharmaceutical composition, such as the dosage forms and compositions of the present disclosure. Unless specifically indicated, $C_{max}$ refers to the overall maximum observed concentration The term "pharmaceutically acceptable" (such as in the recitation of a "pharmaceutically acceptable salt" or a "pharmaceutically acceptable diluent") refers to a material that is compatible with administration to a human subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, mono-malic acid, mono oxalic acid, tartaric acid such as mono tartaric acid (e.g., (+) or (−)-tartaric acid or mixtures thereof), amino acids (e.g., (+) or (−)-amino acids or mixtures thereof), and the like. These salts can be prepared by methods known to those skilled in the art. Examples of pharmaceutically acceptable salts of upadacitinib may be found in WO 2017/066775, which is hereby incorporated by reference in its entirety.

The term "subject" refers to a human subject.

A "population of subjects" refers to the group of subjects participating in a clinical trial, with all subjects suffering from the same disease or symptom to be treated, wherein the clinical trial comprises a treatment arm (a subgroup of the subjects treated with the JAK1 inhibitor), and a placebo arm (a subgroup of the subjects not treated with the JAK1 inhibitor). When used in connection with the treatment of a population of subjects, the phrase "at least X % of the subjects in the treated population achieve" a particular response refers to the placebo corrected X % response (subjects treated-subjects not treated).

As used herein, the term "pediatric patient" refers to a human patient of less than 18 years old.

The terms "patient" and "subject" are used interchangeably herein.

The terms "treating" and "treatment" refer to ameliorating, suppressing, eradicating, reducing the severity of, decreasing the frequency of incidence of, preventing, reducing the risk of, slowing the progression of damage caused by or delaying the onset of the condition or improving the quality of life of a patient suffering from the condition.

The abbreviation "% CV" refers to the coefficient of variation, expressed as a percent. % CV is calculated according to the following equation: % CV=(SD/x)*100, wherein x is the mean value and SD is the standard deviation.

As used herein, the term "entry into a use environment" means contact of a formulation of the disclosure with the gastric fluids of the subject to whom it is administered, or with a fluid intended to simulate gastric fluid.

The abbreviation "MTX" refers to methotrexate.

The term "upadacitinib freebase" refers to freebase (non-salt, neutral) forms of upadacitinib. Examples of upadacitinib freebase solid-state forms include amorphous upadacitinib freebase and crystalline freebases of upadacitinib, such as crystalline freebase solvates, crystalline freebase hydrates, crystalline freebase hemihydrates, and crystalline freebase anhydrates of upadacitinib. Specific examples of upadacitinib freebase solid-state forms include but are not limited to Amorphous Upadacitinib Freebase, Upadacitinib Freebase Solvate Form A, Upadacitinib Freebase Hydrate Form B, Upadacitinib Freebase Hydrate Form C (which is a hemihydrate), and Upadacitinib Freebase Anhydrate Form D, each as described in WO 2017/066775 and WO 2018/165581.

The term "upadacitinib freebase equivalent" amount of the neutral upadacitinib freebase (active ingredient) administered, and not including any coformer (e.g., solvent or water molecule(s)) of a solvate or hydrate (including hemihydrate), and not including any pharmaceutically acceptable salt counteranions of a pharmaceutically acceptable salt. For example, 15.4 mg of crystalline upadacitinib freebase hemihydrate (which includes ½ of a water conformer molecule per upadacitinib freebase molecule) delivers 15 mg of upadacitinib freebase equivalent, while 30.7 mg of crystalline upadacitinib freebase hemihydrate (which includes ½ of a water conformer molecule per upadacitinib freebase molecule) delivers 30 mg of upadacitinib freebase equivalent.

The term "remission" is defined as having all of the following:

Absence of GCA signs and symptoms; and

Adherence to the 26-week CS taper regimen in Table 1 below.

The term "sustained remission" is defined as having all of the following:

Absence of GCA signs and symptoms over a period of time;

Adherence to the 26-week CS taper regimen in Table 1 below.

The term "complete remission" is defined as having all of the following:

Absence of GCA signs and symptoms;

Normalization of ESR (to <30 mm/hr); if ESR ≥30 mm/hr and elevation is not attributable to GCA, this criterion can still be met;

Normalization of hsCRP (to <1 mg/dL without elevation [on 2 consecutive visits] to ≥1 mg/dL); and Adherence to the 26-week CS taper regimen in Table A below.

The term "sustained complete remission" is defined as having all of the following:

Absence of GCA signs and symptoms over a period of time;

Normalization of ESR (to <30 mm/hr) over a period of time; if ESR ≥30 mm/hr and elevation is not attributable to GCA, this criterion can still be met;

Normalization of hsCRP (to <1 mg/dL without elevation [on 2 consecutive visits] to ≥1 mg/dL) over a period of time; and Adherence to the 26-week CS taper regimen in Table A below.

TABLE A

| Corticosteroid Tapering Schedule | | | | | | | | | | | |
|---|---|---|---|---|---|---|---|---|---|---|---|
| 52 Week Corticosteroid* Taper (Dose in mg) | | | | | | 26 Week Corticosteroid* Taper (Dose in mg) | | | | | |
| Baseline | 20 | 30 | 40 | 50 | 60 | Baseline | 20 | 30 | 40 | 50 | 60 |
| Wk 1 | 17 | 25 | 35 | 40 | 50 | Wk 1 | 15 | 25 | 35 | 40 | 50 |
| Wk 2 | 17 | 20 | 30 | 35 | 40 | Wk 2 | 12 | 20 | 30 | 35 | 40 |
| Wk 3 | 15 | 17 | 25 | 30 | 35 | Wk 3 | 12 | 15 | 25 | 30 | 35 |
| Wk 4 | 15 | 17 | 20 | 25 | 30 | Wk 4 | 10 | 12 | 20 | 25 | 30 |
| Wk 5 | 12 | 15 | 17 | 20 | 25 | Wk 5 | 9 | 12 | 15 | 20 | 25 |
| Wk 6 | 10 | 15 | 17 | 17 | 20 | Wk 6 | 8 | 10 | 12 | 15 | 20 |
| Wk 7 | 10 | 12 | 15 | 17 | 17 | Wk 7 | 7 | 9 | 12 | 12 | 15 |
| Wk 8 | 10 | 10 | 15 | 15 | 17 | Wk 8 | 6 | 8 | 10 | 12 | 12 |
| Wk 9 | 10 | 10 | 12 | 15 | 15 | Wk 9 | 6 | 7 | 9 | 10 | 12 |
| Wk 10 | 9 | 10 | 10 | 12 | 15 | Wk 10 | 5 | 6 | 8 | 9 | 10 |
| Wk 11 | 9 | 10 | 10 | 10 | 12 | Wk 11 | 5 | 6 | 7 | 8 | 9 |
| Wk 12 | 9 | 9 | 10 | 10 | 10 | Wk 12 | 4 | 5 | 6 | 7 | 8 |
| Wk 13 | 9 | 9 | 10 | 10 | 10 | Wk 13 | 4 | 5 | 6 | 6 | 7 |
| Wk 14 | 8 | 9 | 9 | 10 | 10 | Wk 14 | 3 | 4 | 5 | 6 | 6 |
| Wk 15 | 8 | 9 | 9 | 9 | 10 | Wk 15 | 3 | 4 | 5 | 5 | 6 |
| Wk 16 | 8 | 8 | 9 | 9 | 9 | Wk 16 | 2 | 3 | 4 | 5 | 5 |
| Wk 17 | 8 | 8 | 9 | 9 | 9 | Wk 17 | 2 | 3 | 4 | 4 | 5 |
| Wk 18 | 7 | 8 | 8 | 9 | 9 | Wk 18 | 1 | 2 | 3 | 4 | 4 |
| Wk 19 | 7 | 8 | 8 | 8 | 9 | Wk 19 | 1 | 2 | 3 | 3 | 4 |
| Wk 20 | 7 | 7 | 8 | 8 | 8 | Wk 20 | 0 | 1 | 2 | 3 | 3 |
| Wk 21 | 7 | 7 | 8 | 8 | 8 | Wk 21 | 0 | 1 | 2 | 2 | 3 |
| Wk 22 | 6 | 7 | 7 | 8 | 8 | Wk 22 | 0 | 0 | 1 | 2 | 2 |
| Wk 23 | 6 | 7 | 7 | 7 | 8 | Wk 23 | 0 | 0 | 1 | 1 | 2 |
| Wk 24 | 6 | 6 | 7 | 7 | 7 | Wk 24 | 0 | 0 | 0 | 1 | 1 |
| Wk 25 | 6 | 6 | 7 | 7 | 7 | Wk 25 | 0 | 0 | 0 | 0 | 1 |

16

TABLE A-continued

| Corticosteroid Tapering Schedule | | | | | | | | | | | |
|---|---|---|---|---|---|---|---|---|---|---|---|
| 52 Week Corticosteroid* Taper (Dose in mg) | | | | | | 26 Week Corticosteroid* Taper (Dose in mg) | | | | | |
| Baseline | 20 | 30 | 40 | 50 | 60 | Baseline | 20 | 30 | 40 | 50 | 60 |
| Wk 26 | 5 | 6 | 6 | 7 | 7 | Wk 26 | 0 | 0 | 0 | 0 | 0 |
| Wk 27 | 5 | 6 | 6 | 6 | 7 | Wk 27 | 0 | 0 | 0 | 0 | 0 |
| Wk 28 | 5 | 5 | 6 | 6 | 6 | Wk 28 | 0 | 0 | 0 | 0 | 0 |
| Wk 29 | 5 | 5 | 6 | 6 | 6 | Wk 29 | 0 | 0 | 0 | 0 | 0 |
| Wk 30 | 4 | 5 | 5 | 6 | 6 | Wk 30 | 0 | 0 | 0 | 0 | 0 |
| Wk 31 | 4 | 5 | 5 | 5 | 6 | Wk 31 | 0 | 0 | 0 | 0 | 0 |
| Wk 32 | 4 | 4 | 5 | 5 | 5 | Wk 32 | 0 | 0 | 0 | 0 | 0 |
| Wk 33 | 4 | 4 | 5 | 5 | 5 | Wk 33 | 0 | 0 | 0 | 0 | 0 |
| Wk 34 | 3 | 4 | 4 | 5 | 5 | Wk 34 | 0 | 0 | 0 | 0 | 0 |
| Wk 35 | 3 | 4 | 4 | 4 | 5 | Wk 35 | 0 | 0 | 0 | 0 | 0 |
| Wk 36 | 3 | 3 | 4 | 4 | 4 | Wk 36 | 0 | 0 | 0 | 0 | 0 |
| Wk 37 | 3 | 3 | 4 | 4 | 4 | Wk 37 | 0 | 0 | 0 | 0 | 0 |
| Wk 38 | 2 | 3 | 3 | 4 | 4 | Wk 38 | 0 | 0 | 0 | 0 | 0 |
| Wk 39 | 2 | 3 | 3 | 3 | 4 | Wk 39 | 0 | 0 | 0 | 0 | 0 |
| Wk 40 | 2 | 2 | 3 | 3 | 3 | Wk 40 | 0 | 0 | 0 | 0 | 0 |
| Wk 41 | 2 | 2 | 3 | 3 | 3 | Wk 41 | 0 | 0 | 0 | 0 | 0 |
| Wk 42 | 1 | 2 | 2 | 3 | 3 | Wk 42 | 0 | 0 | 0 | 0 | 0 |
| Wk 43 | 1 | 2 | 2 | 2 | 3 | Wk 43 | 0 | 0 | 0 | 0 | 0 |
| Wk 44 | 1 | 1 | 2 | 2 | 2 | Wk 44 | 0 | 0 | 0 | 0 | 0 |
| Wk 45 | 1 | 1 | 2 | 2 | 2 | Wk 45 | 0 | 0 | 0 | 0 | 0 |
| Wk 46 | 0 | 1 | 1 | 2 | 2 | Wk 46 | 0 | 0 | 0 | 0 | 0 |
| Wk 47 | 0 | 1 | 1 | 1 | 2 | Wk 47 | 0 | 0 | 0 | 0 | 0 |
| Wk 48 | 0 | 0 | 1 | 1 | 1 | Wk 48 | 0 | 0 | 0 | 0 | 0 |
| Wk 49 | 0 | 0 | 1 | 1 | 1 | Wk 49 | 0 | 0 | 0 | 0 | 0 |
| Wk 50 | 0 | 0 | 0 | 1 | 1 | Wk 50 | 0 | 0 | 0 | 0 | 0 |
| Wk 51 | 0 | 0 | 0 | 0 | 1 | Wk 51 | 0 | 0 | 0 | 0 | 0 |
| Wk 52 | 0 | 0 | 0 | 0 | 0 | Wk 52 | 0 | 0 | 0 | 0 | 0 |

Open label taper until 20 mg
*Prednisone or Prednisolone

The terms "treating", "treatment", and "therapy" and the like, as used herein, are meant to include therapeutic measures for a disease or disorder leading to a clinically desirable or beneficial effect, including but not limited to clinically significant improvement in the signs and symptoms of GCA over a period of time.

The dosage strength of upadacitinib recited in the present application is based on the weight of anhydrous freebase upadacitinib present in the active ingredient delivered to the patient. For example, a dose of "15 mg of upadacitinib" or "UPA 15 MG" refers to the 15 mg amount of the neutral upadacitinib freebase present in the active ingredient, not including any coformer (e.g., solvent or water molecule(s)) of a solvate or hydrate (including hemihydrate) or counteranions of a pharmaceutically acceptable salt), that may also be present in the active ingredient. So, for example, the administration of "15 mg of upadacitinib" includes the administration of 15.4 mg of crystalline upadacitinib freebase hemihydrate (which includes ½ of a water conformer molecule per upadacitinib freebase molecule) which delivers 15 mg of anhydrous freebase upadacitinib to a patient.

II. Methods of Treatment

The present disclosure relates to methods of treating a JAK-associated condition in a subject, particularly a human subject suffering from or susceptible to the condition, comprising administering to the subject a therapeutically effective amount of Compound 1 freebase or a pharmaceutically acceptable salt thereof or one or more solid-state forms of Compound 1 as described in the present disclosure. Another aspect of the disclosure relates to Compound 1 freebase or a pharmaceutically acceptable salt thereof or one or more solid-state forms of Compound 1 as described in the present disclosure for use in treatment of a JAK-associated condition in a subject, particularly in a human subject suffering from or susceptible to the condition, the use comprising administering to the subject a therapeutically effective amount of Compound 1 freebase or a pharmaceutically acceptable salt thereof or one or more solid-state forms of Compound 1. In one aspect, the condition is a JAK-1-associated condition. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of immunomodulation, inflammation, and proliferative disorders (such as cancer) in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of immunomodulation, inflammation, and proliferative disorders (such as cancer) in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Anhydrate Form D. In another aspect, the solid-state form is the Freebase Hydrate Form B. In another aspect, the solid-state form is the Freebase Hydrate Form C. In another aspect, the solid-state form is the Tartrate Hydrate.

In one embodiment, the present disclosure relates to methods of treating a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B.

In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), auto-immune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), auto-immune mediated hypoglycaemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition, the use comprising administering to the subject a therapeutically effective amount of Compound 1 freebase or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating arthritis in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of arthritis in a subject, particularly in a human subject suffering from or susceptible to arthritis, the use comprising administering to the subject a therapeutically effective amount of Compound 1 freebase or a pharmaceutically acceptable salt thereof or a solid-state form of Compound 1. In one aspect, the arthritis is selected from the group consisting of rheumatoid arthritis, juvenile idiopathic arthritis, and psoriatic arthritis. In another aspect, the arthritis is rheumatoid arthritis. In another aspect, the arthritis is juvenile idiopathic arthritis. In another aspect, the arthritis is psoriatic arthritis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a spondyloarthropathy in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of spondyloarthropathy, particularly in a human subject suffering from or susceptible to spondyloarthropathy, the use comprising administering to the subject a therapeutically effective amount of Compound 1 freebase or a pharmaceutically acceptable salt thereof or a solid-state form of Compound 1. In one aspect, the spondyloarthropathy is ankylosing spondylitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a gastrointestinal condition in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a gastrointestinal condition, particularly in a human subject suffering from or susceptible to a gastrointestinal condition, the use comprising administering to the subject a therapeutically effective amount of Compound 1 freebase or a pharmaceutically acceptable salt thereof or a solid-state form of Compound 1. In one aspect, the gastrointestinal condition is selected from the group consisting of Crohn's disease and ulcerative colitis. In another aspect, the gastrointestinal condition is Crohn's disease. In another aspect, the gastrointestinal condition is ulcerative colitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a skin condition, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a skin condition, particularly in a human subject suffering from or susceptible to a skin condition, the use comprising administering to the subject a therapeutically effective amount of Compound 1 freebase or a pharmaceutically acceptable salt thereof or a solid-state form of Compound 1. In one aspect, the skin condition is selected from the group consisting of psoriasis, plaque psoriasis, nail psoriasis, and hidradenitis suppurativa. In another aspect, the skin condition is psoriasis. In another aspect, the skin condition is plaque psoriasis. In another aspect, the skin condition is nail psoriasis. In another aspect, the skin condition is hidradenitis suppurativa. In another aspect, the skin condition is atopic dermatitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

The therapeutically effective dose level for any particular subject will depend upon the specific situation and can depend upon a variety of factors including the type, age, weight, sex, diet, and condition of the subject being treated; the severity of the pathological condition; activity of the specific compound employed; the specific composition employed; the age, body weight, general health, sex and diet of the subject; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The total daily dose of the solid-state form (administered in single or divided doses) typically is from about 0.001 to about 100 mg/kg, or from about 0.001 to about 30 mg/kg, or from about 0.001 to about 15 mg/kg. In another embodiment, the total daily dose is from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

In one embodiment, the daily dose of the solid-state form administered to the subject is from about 0.01 mg to about 3000 mg. In one aspect, the daily dose is from about 0.1 mg to about 1000 mg. In another aspect, the daily dose is from is from about 1 mg to about 500 mg. In another aspect, the daily dose is from about 1 mg to about 250 mg. In another aspect, the daily dose is from about 1 mg to about 100 mg. In another aspect, the daily dose is from about 1 mg to about 50 mg. In another aspect, the daily dose is from about 1 mg to about 45 mg. In another aspect, the daily dose is from about 1 mg to about 30 mg. In another aspect, the daily dose is from about 1 mg to about 25 mg. In another aspect, the daily dose is from about 1 mg to about 24 mg. In another aspect, the daily dose is from about 1 mg to about 15 mg. In another aspect, the daily dose is from about 1 mg to about 7.5 mg. In another aspect, the daily dose is from about 25 mg to about 50 mg. In another aspect, the daily dose is from about 1 mg to about 10 mg. In another aspect, the daily dose is from about 10 mg to about 20 mg. In another aspect, the daily dose is from about 20 mg to about 30 mg. In another aspect, the daily dose is from about 30 mg to about 40 mg. In another aspect, the daily dose is from about 7.5 mg to about 45 mg. In another aspect, the daily dose is from about 15 mg to about 30 mg. In another aspect, the daily dose is about 3 mg. In another aspect, the daily dose is about 6 mg. In another aspect, the daily dose is about 7.5 mg. In another aspect, the daily dose is about 12 mg. In another aspect, the daily dose is about 15 mg. In another aspect, the daily dose is about 18 mg. In another aspect, the daily dose is about 24 mg. In another aspect, the daily dose is about 30 mg. In another aspect, the daily dose is about 36 mg. In another aspect, the daily dose is about 45 mg.

In one embodiment, a dose of about 3 mg, about 6 mg, about 12 mg, or about 24 mg per unit dosage form (e.g., per tablet or capsule) of a solid-state form of Compound 1 is administered orally BID (twice daily) in equal amounts (e.g., twice a day, about 3 mg each time) to a human subject.

In one embodiment, the disclosure relates to a method of treating a subject having rheumatoid arthritis, the method comprising administering to the subject about 3 mg, per unit dosage form (e.g., per tablet or capsule) of a solid-state form of Compound 1 orally BID (twice daily) in equal amounts (e.g., twice a day, about 3 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 3 mg, per unit dosage form (e.g., per tablet or capsule) of a solid-state form of Compound 1 orally BID (twice daily) in equal amounts (e.g., twice a day, about 3 mg each time).

In one embodiment, the disclosure relates to a method of treating a subject having rheumatoid arthritis, the method comprising administering to the subject about 6 mg, per unit dosage form (e.g., per tablet or capsule) of a solid-state form of Compound 1 orally BID (twice daily) in equal amounts (e.g., twice a day, about 6 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 6 mg, per unit dosage form (e.g., per tablet or capsule) of a solid-state form of Compound 1 orally BID (twice daily) in equal amounts (e.g., twice a day, about 6 mg each time).

In one embodiment, the disclosure relates to a method of treating a subject having rheumatoid arthritis, the method comprising administering to the subject about 12 mg, per unit dosage form (e.g., per tablet or capsule) of a solid-state form of Compound 1 orally BID (twice daily) in equal amounts (e.g., twice a day, about 12 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 12 mg, per unit dosage form (e.g., per tablet or capsule) of a solid-state form of Compound 1 orally BID (twice daily) in equal amounts (e.g., twice a day, about 12 mg each time).

In one embodiment, the disclosure relates to a method of treating a subject having rheumatoid arthritis, the method comprising administering to the subject about 24 mg, per unit dosage form (e.g., per tablet or capsule) of a solid-state form of Compound 1 orally BID (twice daily) in equal amounts (e.g., twice a day, about 24 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 24 mg, per unit dosage form (e.g., per tablet or capsule) of a solid-state form of Compound 1 orally BID (twice daily) in equal amounts (e.g., twice a day, about 24 mg each time).

In another embodiment, the methods or uses comprise administering orally QD (once daily) to a human subject a dose of about 7.5 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 7.5 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 7.5 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 15 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 15 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 15 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 24 mg of Compound 1 freebase or a pharmaceutically acceptable salt thereof. The 24 mg QD dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously.

In another embodiment, the methods or uses comprise administering orally QD (once daily) to a human subject a dose of about 24 mg of a solid-state form of Compound 1. In one embodiment, the methods or uses comprise administering orally QD (once daily) to a human subject a solid-state form of Compound 1 in an amount sufficient to deliver 24 mg of Compound 1 freebase equivalent to the subject. The 24 mg QD dose of the solid-state form of Compound 1 may be administered as either a single dosage form comprising about 24 mg per unit dosage form (e.g., per tablet or capsule) of the solid-state form of Compound 1, or two dosage forms comprising about 12 mg per unit dosage form (e.g., per tablet or capsule) of the solid-state form of Compound 1 administered simultaneously. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 30 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 30 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 30 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 36 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 36 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 36 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 45 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 45 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 45 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In certain embodiments, Compound 1 freebase or a pharmaceutically acceptable salt thereof and/or solid-state forms thereof can be used to treat rheumatoid arthritis (RA), including reducing signs and symptoms of RA, inducing a major clinical response, inhibiting the progression of or treating structural damage associated with RA, and improving physical function in adult subjects, such as adult subjects with moderately to severely active RA. In one embodiment, Compound 1 freebase or a pharmaceutically acceptable salt thereof and/or solid-state forms thereof are used to treat RA in adult subjects. In one embodiment, Compound 1 freebase or a pharmaceutically acceptable salt thereof and/or solid-state forms thereof are used to reduce signs and symptoms of RA in adult subjects. In one embodiment, Compound 1 freebase or a pharmaceutically acceptable salt thereof and/or solid-state forms thereof induce a major clinical response in adult subjects with RA. In one embodiment, Compound 1 freebase or a pharmaceutically acceptable salt thereof and/or solid-state forms thereof are used to inhibit the progression of structural damage associated with RA in adult subjects. In one embodiment, Compound 1 freebase and/or solid-state forms thereof are used to treat structural damage associated with RA in adult subjects. In one embodiment, Compound 1 freebase or a pharmaceutically acceptable salt thereof and/or solid-state forms thereof are used to improve physical function in adult subjects. In one embodiment, the adult subjects have RA. In another embodiment, the adult subjects have moderately to severely active RA.

Compound 1 freebase or a pharmaceutically acceptable salt thereof or solid-state forms thereof may be used alone, or in combination with methotrexate or other non-biologic disease-modifying anti-rheumatic drugs (DMARDs), and/or in combination with anti-TNFα biological agents, such as TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept).

Patients having active rheumatoid arthritis (RA) may be diagnosed according to 1987-revised American College of Rheumatology (ACR) classification criteria or the 2010 ACR/EULAR criteria. In certain embodiments, RA may be diagnosed based on patients having at least 6 swollen and 6 tender joints. In certain embodiments, patients treatable with Compound 1 or solid-state forms thereof may include those who have failed therapy with at least one (e.g., at least one but no more than four) DMARDs and/or have inadequate response to methotrexate, adalimumab, infliximab, etanercept, or other anti-TNFα biological agents, or non-anti-TNF biologics.

In certain embodiments, Compound 1 freebase or a pharmaceutically acceptable salt thereof or solid-state forms thereof halt disease progression, and/or relieves at least a symptom of the disease, which may be detected or monitored by X-ray results, including radiographic progression of joint damage.

In certain embodiments, therapeutic efficacy can be measured by improvements in ACR20, ACR50, and/or ACR70, either in individual patients or a population of patients in need of treatment. In certain embodiments, statistically significant improvement (as compared placebo or untreated control) over a treatment period (e.g., 1 week, 2 weeks, 4 weeks, 6 weeks, 8 weeks, 12 weeks, 2 months, 3 months, 6 months, 1 year, 2 years, 5 years, 10 years or more) in one or more of the ACR criteria is achieved. Statistical significance is manifested by a p value of less than 0.05, or less than 0.01.

Components of the ACR responses are well known in the art, and may include the median number of tender joints, the median number of swollen joints, physician global assessment such as one measured by visual analog scale (VAS), patient global assessment such as one measured by visual analog scale, pain such as one measured by visual analog scale, disability index of the Health Assessment Questionnaire (HAQ-DI score), and C-reactive protein (CRP) (mg/dL).

In certain embodiments, an ACR20 response is determined based on a 20% or greater improvement in tender joint count (TJC) and swollen joint count (SJC) and greater than or equal to 3 of the 5 measures of Patient's Assessment of Pain (VAS), Patient's Global Assessment of Disease Activity (VAS), Physician's Global Assessment of Disease Activity (VAS), HAQ-DI, or high sensitivity C-reactive protein (hsCRP). In some embodiments, an ACR50 response is determined based on a 50% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. An ACR70 response is determined based on a 70% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. In certain embodiments, the ACR20, ACR50, or ACR70 response occurs by week 12 of treatment.

In certain embodiments, a DAS28 (disease activity score based on the 28 joints examined) score is determined as a composite score derived from four of the following measures: examination of joints for swelling and tenderness, global scores of pain and overall status, blood markers of inflammation (e.g. ESR (erythrocyte sedimentation rate) and CRP (C reactive protein), referred to herein as DAS28 (CRP)), questionnaires (e.g. the HAQ (health assessment questionnaire) which assess function) and X-rays and other imaging techniques such as ultrasound and MRI.

In certain embodiments, structural joint damage can be assessed radiographically and expressed as change in Total Sharp Score (TSS) and its components, the erosion score and Joint Space Narrowing (JSN) score, for example, at week 12 compared to baseline, or at week 24 as compared to baseline.

In certain embodiments, improvement in signs and symptoms of the disease can be measured by patient physical function response, such as disability index of Health Assessment Questionnaire (HAQ-DI), and/or the health-outcomes as assessed by The Short Form Health Survey (SF 36). In one embodiment, improvement in signs and symptoms of the disease is measured by HAQ-DI, including the minimal clinically important difference (MCID) of −0.22. Improvement can also be measured by one or both of Physical Component Summary (PCS) and the Mental Component Summary (MCS). Improvements can further be measured by Work Instability Scale for RA (RA-WIS) (see Gilworth et al., Arthritis & Rheumatism (Arthritis Care & Research) 49 (3): 349-354, 2003, incorporated by reference).

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 7.5 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of a solid-state form of Compound 1 orally QD (once daily). In one embodiment, the solid-state form delivers about 7.5 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 15 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of a solid-state form of Compound 1 orally QD (once daily). In one embodiment, the solid-state form delivers about 15 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 24 mg of Compound 1 freebase or a pharmaceutically acceptable salt thereof orally QD (once daily). The 24 mg dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of a solid-state form of Compound 1 orally QD (once daily). In one embodiment, the method comprising administering to the subject a solid-state form of Compound 1 orally QD (once daily) in an amount sufficient to deliver 24 mg of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 24 mg of a solid-state form of Compound 1 orally QD (once daily). In one embodiment, the solid-state form delivers about 24 mg of Compound 1 freebase equivalent to the subject. The 24 mg dose of the solid-state form of Compound 1 may be administered as either a single dosage form comprising about 24 mg per unit dosage form (e.g., per tablet or capsule) of the solid-state form of Compound 1, or two dosage forms comprising about 12 mg per unit dosage form (e.g., per tablet or capsule) of the solid-state form of Compound 1 administered simultaneously. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 30 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of a solid-state form of Compound 1 orally QD (once daily). In one embodiment, the solid-state form delivers about 30 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 36 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of a solid-state form of Compound 1 orally QD (once daily). In one embodiment, the solid-state form delivers about 36 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of Compound 1 freebase or a pharmaceutically acceptable salt thereof orally QD (once daily). In another aspect, the present disclosure relates to Compound 1 free-base or a pharmaceutically acceptable salt thereof for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 45 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of a solid-state form of Compound 1 orally QD (once daily). In one embodiment, the solid-state form delivers about 45 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhdyrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating moderate to severely active rheumatoid arthritis in an adult subject, particularly in a human subject suffering from or susceptible to moderate to severely active rheuma-toid arthritis, the method comprising administering to the subject a therapeutically effective amount of Compound 1 (freebase), or a pharmaceutically acceptable salt thereof or a solid-state form of Compound 1. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule) of Compound 1 freebase equivalent. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid-state form of Compound 1. In one embodiment, the Compound 1 (freebase) or a pharmaceu-tically acceptable salt thereof or the solid-state form of Compound 1 is administered to the subject orally QD (once daily). In another aspect, the disclosure relates to Compound 1 freebase or a pharmaceutically acceptable salt thereof or a solid-state form of Compound 1 (e.g., a crystalline hydrate or crystalline anhydrate), as described in the present disclo-sure, for use in treatment of moderate to severely active rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystal-line hydrate is a hemihydrate. In one embodiment, the hemihydrate is Freebase Hydrate Form C. In one embodi-ment, the solid-state form is a crystalline anhydrate. In one embodiment, the crystalline anhydrate is Freebase Anhy-drate Form D. In one embodiment, the solid-state form is the Freebase Solvate Form A. In another aspect, the solid-state form is the Hydrochloride Solvate form AA. In one embodi-ment, the solid-state form is the Hydrochloride Solvate Form BB. In one embodiment, the solid-state form is the Hydrochloride Solvate Form CC. In one embodiment, the solid-state form is the L-Maleate Form AAA. In one embodiment, the solid-state form is the L-Maleate Form BBB. In one embodiment, the Compound 1 (freebase) or a pharmaceutically acceptable salt thereof or the solid-state form of Compound 1 is in a once daily extended-release formulation. In one embodiment, the formulation delivers about 7.5 mg or about 15 mg or about 30 mg or about 45 mg per unit dosage form (e.g., per tablet or capsule) of Com-pound 1 (freebase equivalent) or a solid-state form of Compound 1 orally QD (once daily).

In one embodiment, the subject having moderate to severely active rheumatoid arthritis has, prior to treatment, at least one of the following identifying characteristics: at least 6 swollen joints (based on 66 joint counts), at least 6 tender joints (based on 68 joint counts), high-sensitivity C-reactive protein (hsCRP) greater than the upper limit of normal (ULN), or positive test results for both rheumatoid factor (RF) and anti-cyclic citrullinated peptide (CCP). In one embodiment, the subject having moderate to severely active rheumatoid arthritis has, prior to treatment, at least 6 swollen joints (based on 66 joint counts) and at least 6 tender joints (based on 68 joint counts). Methods for assessing tender and swollen joints are known, and described in, for example, Scott, et al., Clinical and Experimental Rheuma-tology, 2014, Vol. 32 (Supp. 85), S7-S12.

Thus, in another embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid-state form of Compound 1 (e.g., a crystalline hydrate or a crystalline anhydrate) as described herein, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid-state form of Compound 1 in an amount sufficient to deliver to the subject about 7.5 or about 15 mg or about 30 mg or about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule) of a solid-state form of Compound 1. In another aspect, the disclosure relates to Compound 1 freebase or a pharmaceutically acceptable salt thereof or a solid-state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject a therapeutically effective amount of Compound 1 freebase or a pharmaceutically acceptable salt thereof or a solid-state form of Compound 1. In one embodiment, the therapeutically effective amount of the solid-state form of Compound 1 delivers to the subject about 7.5 mg or about 15 mg or about 30 mg or about 45 mg per unit dosage form (e.g., per tablet or capsule) of Compound 1 (freebase equivalent) or a solid-state form of Compound 1 orally QD (once daily). In one embodiment, the Compound 1 (freebase) or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is administered to the subject orally QD (once daily). In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is Tartrate Hydrate. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 15 mg, per unit dosage form (e.g., per tablet or capsule), per day of Compound 1 (freebase), or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 30 mg, per unit dosage form (e.g., per tablet or capsule), per day of Compound 1 (freebase), or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 45 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 45 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the adult subject receiving the treatment achieves an ACR20 response after treatment. In one embodiment, the adult subject achieves an ACR20 response after treatment for at least twelve weeks (e.g., at week 12 of treating). In another embodiment, the adult subject receiving the treatment achieves an ACR50 response after treatment. In one embodiment, the adult subject achieves an ACR50 response after treatment for at least twelve weeks (e.g., at week 12 of treating), or after at least twenty-four weeks (e.g., at week 24). In another embodiment, the adult subject receiving the treatment achieves an ACR70 response after treatment. In one embodiment, the adult subject achieves an ACR70 response after treatment for at least twelve weeks (e.g., at week 12 of treating). In certain embodiments, the adult subject achieves an ACR20 response, an ACR50 response, and/or an ACR70 response following treatment for at least twelve weeks (e.g., at week 12 of treating).

In one embodiment, the adult subject receiving the treatment achieves an ACR20 response after treatment for at least 8 weeks (e.g., at week 8 of treating). In another embodiment, the adult subject receiving the treatment achieves an ACR20 response after treatment for at least 6 weeks (e.g., at week 6 of treating). In another embodiment, the adult subject receiving the treatment achieves an ACR20 response after treatment for at least 4 weeks (e.g., at week 4 of treating). In another embodiment, the adult subject receiving the treatment achieves an ACR20 response after treatment for at least 2 weeks (e.g., at week 2 of treating).

In one embodiment, the adult subject receiving the treatment achieves an ACR50 response after treatment for at least 8 weeks (e.g., at week 8 of treating). In another embodiment, the adult subject receiving the treatment achieves an ACR50 response after treatment for at least 6 weeks (e.g., at week 6 of treating). In another embodiment, the adult subject receiving the treatment achieves an ACR50 response after treatment for at least 4 weeks (e.g., at week 4 of treating). In another embodiment, the adult subject receiving the treatment achieves an ACR50 response after treatment for at least 2 weeks (e.g., at week 2 of treating).

In one embodiment, the adult subject receiving the treatment achieves an ACR70 response after treatment for at least 8 weeks (e.g., at week 8 of treating). In another embodiment, the adult subject receiving the treatment achieves an ACR70 response after treatment for at least 6 weeks (e.g., at week 6 of treating). In another embodiment, the adult subject receiving the treatment achieves an ACR70 response after treatment for at least 4 weeks (e.g., at week 4 of treating).

In one embodiment, the adult subject receiving the treatment achieves a change in DAS28 score after treatment. In one embodiment, the change in DAS score is a decrease in DAS28 (CRP) after treatment, as compared to baseline (i.e., DAS28 (CRP) prior to treatment). In one embodiment, the adult subject achieves a decrease in DAS28 score as compared to baseline after treatment for at least twelve weeks (e.g., at week 12 of treating). In one embodiment, the adult subject achieves a decrease in DAS28 (CRP) as compared to baseline after treatment for at least 12 weeks (e.g., at week 12 of treating). In another embodiment, the adult subject achieves a decrease in DAS28 (CRP) as compared to baseline after treatment for at least 8 weeks (e.g., at week 8 of treating). In another embodiment, the adult subject achieves a decrease in DAS28 (CRP) as compared to baseline after treatment for at least 6 weeks (e.g., at week 6 of treating). In another embodiment, the adult subject achieves a decrease in DAS28 (CRP) as compared to baseline after treatment for at least 4 weeks (e.g., at week 4 of treating). In another embodiment, the adult subject achieves a decrease in DAS28 (CRP) as compared to baseline after treatment for at least 2 weeks (e.g., at week 2 of treating).

In another embodiment, the adult subject receiving the treatment achieves a low disease activity (LDA) score or clinical remission after treatment. In one embodiment, the LDA score or clinical remission is measured as a DAS28 score (in particular, DAS28 (CRP)) of 3.2 or less. In another embodiment, the LDA score or clinical remission is measured as a DAS28 (CRP) of less than 2.6. In another embodiment, the LDA score or clinical remission is assessed using Clinical Disease Activity Index (CDAI) criteria. In one embodiment, the adult subject achieves a CDAI score of 10 or less after treatment. In another embodiment, the adult subject achieves a CDAI score of 2.8 or less after treatment. In one embodiment, the adult subject achieves the LDA score or clinical remission after treatment for at least 12 weeks (e.g., at week 12 of treating). In one embodiment, the adult subject achieves the LDA score or clinical remission after treatment for at least 8 weeks (e.g., at week 8 of treating). In one embodiment, the adult subject achieves the LDA score or clinical remission after treatment for at least 6 weeks (e.g., at week 6 of treating). In one embodiment, the adult subject achieves the LDA score or clinical remission after treatment for at least 4 weeks (e.g., at week 4 of treating). In one embodiment, the adult subject achieves the LDA score or clinical remission after treatment for at least 2 weeks (e.g., at week 2 of treating).

In one embodiment, the adult subject receiving the treatment achieves a change in mean modified Total Sharp Score (mTSS). In one embodiment, the adult subject receiving the treatment achieves a change in mTSS after treatment for at least twelve weeks (e.g., at week 12 of treating), or after treatment for at least twenty-four weeks (e.g., at week 24 of treating). In one embodiment, mTSS may be determined by scoring x-rays of the hand/wrist and feet joints for erosions and joint space narrowing. The erosion score and narrowing score are added to determine the total score.

In one embodiment, the adult subject receiving the treatment achieves a change in HAQ-DI score. In one embodiment, the adult subject receiving the treatment achieves a change in HAQ-DI score after treatment for at least twelve weeks (e.g., at week 12 of treating).

In one embodiment, the adult subject receiving the treatment achieves a change in Short Form 36 (SF-36) physical component score (PCS). In one embodiment, the adult subject receiving the treatment achieves a change in SF-36 PCS after treatment for at least twelve weeks (e.g., at week 12 of treating). SF-36 is a 36 item participant questionnaire with questions relating to participant health and daily activities.

In one embodiment, the adult subject receiving the treatment achieves a clinical remission (CR). In one embodiment, the adult subject receiving the treatment achieves a CR after treatment for at least twelve weeks (e.g., at week 12 of treating). In one embodiment, CR is determined based on DAS28 C-Reactive Protein (DAS28 (CRP)) response rate. In one embodiment, CR is a DAS28 (CRP) score of less than 2.6.

In one embodiment, the adult subject receiving the treatment achieves a change in functional assessment of chronic illness therapy (FACIT-F). In one embodiment, the adult subject receiving the treatment achieves a change in FACIT-F after treatment for at least twelve weeks (e.g., at week 12 of treating). FACIT-F is a participant questionnaire with 13 indexes rated on a 5 point scale. The indexes relate to the participant's level of fatigue during the past seven days.

In one embodiment, the adult subject receiving the treatment achieves a change in work instability score for rheumatoid arthritis (RA-WIS). In one embodiment, the adult subject receiving the treatment achieves a change in RA-WIS after treatment for at least twelve weeks (e.g., at week 12 of treating). RA-WIS is a participant questionnaire containing 23 questions relating to the participant's functioning in their work environment.

In one embodiment, the adult subject receiving the treatment achieves a change in morning stiffness severity. In one embodiment, the adult subject receiving the treatment achieves a change in morning stiffness severity after treatment for at least twelve weeks (e.g., at week 12 of treating). Morning stiffness severity is determined by the Patient's Assessment of Severity and Duration of Morning Stiffness questionnaire.

In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent to the subject, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves an ACR70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 7.5 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 15 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, the adult subject is a subject who has had an inadequate response or intolerance to one or more disease-modifying antirheumatic drugs (DMARDs). In one embodiment, the DMARD is a conventional synthetic DMARD (csDMARD). In another embodiment, the DMARD is a biologic DMARD (bDMARD). Examples of csDMARDs include, but are not limited to, methotrexate (MTX), sulfasalazine, hydroxychloroquine, chloroquine, leflunomide, and azathioprine. Examples of bDMARDs include, but are not limited to, tocilizumab such as ACTEMRA™, etanercept such as p75TNFR1gG (EN-BREL™ brand etanercept), adalimumab (such as HUMIRA™ brand adalimumab), and golimumab such as SIMPONI™ (golimumab). In one embodiment, the csD-MARD is MTX. In one embodiment, the bDMARD is an anti-TNF biologic. An inadequate response or intolerance to one or more DMARDs can be measured using any of the indices described herein (e.g., failure to achieve an ACR20 response). In one embodiment, a subject having an inadequate response to a DMARD is a subject who does not achieve reduced disease activity, does not achieve an improvement in physical function, exhibits no evidence of stopping disease progression, or who experiences disease relapse after treatment with the DMARD. In one embodiment, a subject having an inadequate response to a DMARD is a subject who does not achieve an ACR20 response after treatment with the DMARD. In one embodiment, a subject having an inadequate tolerance (intolerance) to a DMARD is a subject who experiences toxicity or complicating co-morbidities after treatment with the DMARD.

In one embodiment, the adult subject is a subject who has had an inadequate response to stable methotrexate therapy. In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject received a supplement of folic acid for at least four weeks prior to treatment. In another embodiment, the adult subject is administered a supplement of folic acid during treatment.

In one embodiment, the adult subject is a subject who has had an inadequate response or intolerance to at least one anti-TNF therapy. Anti-TNF biologic agents are described elsewhere herein, and include TNF antagonists such as chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept). In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject has been treated with at least one anti-TNF biologic agent for at least three months prior to treatment with Compound 1. In another embodiment, the adult subject received a supplement of folic acid for at least four weeks prior to treatment. In another embodiment, the adult subject is administered a supplement of folic acid during treatment In certain embodiments, the adult subject, who has had an inadequate response or tolerance to one or more DMARDS (including methotrexate and/or an anti-TNF biologic agent), achieves an ACR20 response, an ACR50 response, an ACR70 response, and/or a decrease in DAS28 (CRP) as compared to baseline following treatment for at least twelve weeks (e.g., at week 12 of treating), and/or following treatment for at least 8 weeks (e.g., at week 8 of treating), and/or following treatment for at least 6 weeks (e.g., at week 6 of treating), and/or following treatment for at least 4 weeks (e.g., at week 4 of treating), and/or following treatment for at least 2 weeks (e.g., at week 2 of treating).

For instance, in one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 7.5 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 15 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 24 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 30 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28 (CRP) as compared to baseline at week 8 of treating. In another embodiment, the subject achieves a decrease in DAS28 (CRP) as compared to baseline at week 6 of treating. In another embodiment, the subject achieves a decrease in DAS28 (CRP) as compared to baseline at week 4 of treating. In another embodiment, the subject achieves a decrease in DAS28 (CRP) as compared to baseline at week 2 of treating. In one embodiment, the method or use comprises administering about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, the adult subject is also administered a csDMARD or a bDMARD in a combination therapy, as described hereinafter. In certain embodiments, the DMARD is MTX. In certain embodiments, the adult subject receiving the combination therapy achieves an ACR20 response, an ACR50 response, an ACR70 response, and/or a decrease in DAS28 (CRP) as compared to baseline following treatment. In particular embodiments, the adult subject receiving the combination therapy achieves an ACR20 response, an ACR50 response, an ACR70 response, and/or a decrease in DAS28 (CRP) as compared to baseline at week 12 of treating, and/or at week 8 of treating, and/or at week 6 of treating, and/or at week 4 of treating, and/or at week 2 of treating. In one embodiment, the adult subject receiving the combination therapy is administered about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent. In one embodiment, the adult subject receiving the combination therapy is administered about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent. In one embodiment, the adult subject receiving the combination therapy is administered about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent. In one embodiment, the adult subject receiving the combination therapy is administered about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent. In one embodiment, the method comprises administering about 7.5 mg or about 15 mg or about 30 mg or about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, any of the methods of treating an adult subject having moderate to severely active rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the present disclosure relates to a method of treating structural damage associated with rheumatoid arthritis in an adult subject, particularly in a human subject suffering from or susceptible to structural damage associated with rheumatoid arthritis. The method comprises administering to the subject a therapeutically effective amount of Compound 1 (freebase), or a pharmaceutically acceptable salt thereof or a solid-state form of Compound 1 (e.g., a crystalline hydrate or a crystalline anhydrate) as described herein, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule) of a solid-state form of Compound 1, such that the structural damage in the adult subject is inhibited or lessened. In one embodiment, the Compound 1 (freebase) or a pharmaceutically acceptable salt thereof or the solid-state form of Compound 1 is administered to the subject orally QD (once daily). In one embodiment, the structural damage is selected from the group consisting of loss of bone and/or cartilage, bone erosion, joint space narrowing as measured by radiography, and combinations thereof. In one embodiment, the structural damaged is inhibited or lessened when the structural damage is reduced by at least 20%, or at least 25%, or at least 30%, or at least 50%. In other embodiments, structural damage is inhibited or lessened when there is no further radiographic progression of the structural damage. In certain embodiments, structural joint damage can be assessed radiographically and expressed as change in Total Sharp Score (TSS) and its components, the erosion score and Joint Space Narrowing (JSN) score, for example, at week 12 compared to baseline. In another aspect, the disclosure relates to a solid-state form (and in particular a crystalline hydrate) of Compound 1, as described in the present disclosure, for use in treatment of structural damage associated with rheumatoid arthritis in an adult subject, particularly in a human subject suffering from or susceptible to rheumatoid arthritis. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid-state form is a crystalline anhydrate. In one embodiment, the crystalline anhydrate is Freebase Anhydrate Form D. In one embodiment, the stolid state form is Tartrate Hydrate. In one embodiment, the Compound 1 (freebase) or a pharmaceutically acceptable salt thereof or the crystalline hydrate is in a once daily extended-release formulation. In one embodiment, the Compound 1 (freebase) or a pharmaceutically acceptable salt thereof or the crystalline hydrate is in a once daily extended-release formulation, and the formulation delivers about 7.5 mg or about 15 mg or about 30 mg or about 45 mg per unit dosage form (e.g., per tablet or capsule) of Compound 1 (freebase equivalent) orally QD (once daily).

In another aspect, the disclosure relates to Compound 1 freebase or a pharmaceutically acceptable salt thereof or a solid-state form of Compound 1 (e.g., a crystalline hydrate or crystalline anhydrate), as described in the present disclosure for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject a therapeutically effective amount of Compound 1 freebase or a pharmaceutically acceptable salt thereof or a solid-state form of Compound 1. In one embodiment, the solid-state form is a crystalline hydrate. In one embodiment, the crystalline hydrate is Freebase Hydrate Form B. In one embodiment, the crystalline hydrate is a hemihydrate. In one embodiment, the hemihydrate is Freebase Hydrate Form C. In one embodiment, the solid-state form is a crystalline anhydrate. In one embodiment, the crystalline anhydrate is Freebase Anhydrate Form D. In one embodiment, the Compound 1 (freebase) or a pharmaceutically acceptable salt thereof or the solid-state form of Compound 1 is in a once daily extended-release formulation. In one embodiment, the formulation delivers about 7.5 mg or about 15 mg or about 30 mg or about 45 mg per unit dosage form (e.g., per tablet or capsule) of Compound 1 (freebase equivalent) or a solid-state form of Compound 1 orally QD (once daily).

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 7.5 mg, per unit dosage form (e.g., per tablet or capsule), per day of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 15 mg, per unit dosage form (e.g., per tablet or capsule), per day of Compound 1 (freebase), or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent, such that the structural damage in the adult subject is inhibited or lessened. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 30 mg, per unit dosage form (e.g., per tablet or capsule), per day of Compound 1 (freebase), or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent, such that the structural damage in the adult subject is inhibited or lessened. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent, such that the structural damage in the adult subject is inhibited or lessened. In one embodiment, the method comprises administering to the subject about 45 mg, per unit dosage form (e.g., per tablet or capsule), per day of a solid-state form of Compound 1. In another aspect, the disclosure relates to Compound 1 free-base or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheuma-toid arthritis, such that the structural damage in the adult subject is inhibited or lessened, the use comprising admin-istering to the subject 45 mg, per unit dosage form (e.g., per tablet or capsule) of Compound 1 freebase or a pharmaceu-tically acceptable salt thereof or a solid-state form of Com-pound 1. In one embodiment, the solid-state form is a crystalline hydrate. In one embodiment, the crystalline hydrate is the Freebase Hydrate Form B. In one embodi-ment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodi-ment, the structural damage is selected from the group consisting of loss of bone and/or cartilage, bone erosion, joint space narrowing as measured by radiography, and combinations thereof.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises admin-istering to the subject a therapeutically effective amount of Compound 1 (freebase), or a pharmaceutically acceptable salt thereof or a solid-state form of Compound 1 (e.g., a crystalline hydrate or a crystalline anhydrate) as described herein. In one embodiment, the method comprises admin-istering to the subject about 7.5 mg or about 15 mg or about 30 mg or about 45 mg, per unit dosage form (e.g., per tablet or capsule), per day of Compound 1 (freebase) or a phar-maceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the method comprises administering to the subject about 7.5 mg or about 15 mg or about 30 mg or about 45 mg, per unit dosage form (e.g., per tablet or capsule) of a solid-state form of Compound 1. In one embodiment, the Compound 1 (freebase) or a pharmaceutically acceptable salt thereof or the solid-state form of Compound 1 is administered to the subject orally QD (once daily). In another aspect, the disclosure relates to Compound 1 freebase or a pharmaceu-tically acceptable salt thereof or a solid-state form (and in particular a crystalline hydrate) of Compound 1, as described in the present disclosure, for use in reducing signs and symptoms of rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceu-tically acceptable salt thereof or a solid-state form (and in particular a crystalline hydrate) of Compound 1. In one embodiment, the Compound 1 freebase or a pharmaceuti-cally acceptable salt thereof or the solid-state form of Compound 1 is in a once daily extended-release formula-tion. In one embodiment, the formulation delivers about 7.5 mg or about 15 mg or about 30 mg or about 45 mg per unit dosage form (e.g., per tablet or capsule) of Compound 1 (freebase equivalent) or the solid-state form of Compound 1 to the subject orally QD (once daily). In one embodiment, the solid-state form is a crystalline hydrate. In one embodi-ment, the crystalline hydrate is the Freebase Hydrate Form B. In one embodiment, the crystalline hydrate is the Free-base Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising admin-istering to the subject about 7.5 mg, per unit dosage form (e.g., per tablet or capsule), per day of Compound 1 (free-base), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystal-line hydrate is a hemihydrate. In one embodiment, the hemihydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 7.5 mg per unit dosage form (e.g., per tablet or capsule) of Compound 1 (freebase equivalent) or the solid-state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising admin-istering to the subject about 15 mg, per unit dosage form (e.g., per tablet or capsule), per day of Compound 1 (free-base) or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject, about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or the solid-state form of Compound 1 is administered orally QD (once daily). In one embodiment, the Compound 1 (freebase) or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 15 mg per unit dosage form (e.g., per tablet or capsule) of Compound 1 (freebase equivalent) or the solid-state form of Compound 1 orally QD (once daily) to the subject.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject about 30 mg, per unit dosage form (e.g., per tablet or capsule), per day of Compound 1 (freebase) or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 (freebase) or the crystalline hydrate is in a once daily extended-release formulation. In one embodiment, the Compound 1 (freebase) or a pharmaceutically acceptable salt thereof or the solid-state form of Compound 1 is in a once daily extended-release formulation, and the formulation delivers about 30 mg per unit dosage form (e.g., per tablet or capsule) of Compound 1 (freebase equivalent) or the solid-state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent. In one embodiment, the method comprises administering to the subject about 45 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 45 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 45 mg per unit dosage form (e.g., per tablet or capsule) of Compound 1 (freebase equivalent) or the solid-state form of Compound 1 orally QD (once daily) to the subject.

In another aspect, the disclosure relates to a solid-state form (and in particular a crystalline hydrate) of Compound 1, as described in the present disclosure, for use in reducing signs and symptoms of rheumatoid arthritis in an adult subject, particularly in a human subject suffering from or susceptible to rheumatoid arthritis.

In another embodiment, any of the methods of reducing signs and symptoms of rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the Compound 1 freebase or a pharmaceutically acceptable salt thereof and/or solid-state forms of Compound 1 used in any of the methods set forth herein may be administered to the subject in a once daily extended-release solid oral dosage form. In particular, in one embodiment, the methods comprise once daily administration to the subject of an extended-release (e.g., modified release) solid oral dosage form comprising the Compound 1 freebase or a pharmaceutically acceptable salt thereof or the solid-state form of Compound 1, and a pharmaceutically acceptable polymeric carrier substantially contributing to the modification of the release of the Compound 1 freebase or a pharmaceutically acceptable salt thereof or the solid-state form of Compound 1. In one aspect, the dosage form sustains release of the Compound 1 freebase or a pharmaceutically acceptable salt thereof or the solid-state form of Compound 1 for from about 4 hours to about 24 hours following entry of the dosage form into a use environment. In one embodiment, the dosage form has a release rate of not more than about 60% after passage of about 4 hours following entry of the dosage form into a use environment. The term "entry into a use environment" refers to contact of the dosage form with gastric fluids of the subject to whom it is administered. As used herein, the term "release rate" refers to the percentage of the active ingredient (e.g., Compound 1 or a solid-state form of Compound 1) in the dosage form that is released in the given time period, and under the specified conditions. In one embodiment, the dosage form comprises about 7.5 mg or about 15 mg or about 30 mg or about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the dosage form comprises about 7.5 mg or about 15 mg or about 30 mg or about 45 mg, per unit dosage form (e.g., per tablet or capsule), per day of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the pharmaceutically acceptable polymeric carrier is a release control polymer, as set forth herein.

Thus, in one aspect, the dosage form sustains release of the Compound 1 freebase or a pharmaceutically acceptable salt thereof or the solid-state form of Compound 1 for from about 4 hours to about 24 hours. In one embodiment, the dosage form releases the active ingredient (i.e., Compound 1 or a solid-state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising once daily administration to a subject suffering from or susceptible to the condition, of an extended-release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the use comprising once daily administration to a subject suffering from or susceptible to the condition, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another embodiment, the disclosure is directed to a method of treating an adult subject having moderate to severely active rheumatoid arthritis, the method comprising once daily administration to the subject, particularly a human subject suffering from or susceptible to rheumatoid arthritis, of an extended-release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In another aspect, the disclosure is directed to an extended-release solid oral dosage form comprising Compound 1 freebase or a pharmaceutically acceptable salt thereof or a solid-state form of Compound 1 for use in treating an adult subject having moderate to severely active rheumatoid arthritis, the use comprising once daily administration to the subject, particularly a subject suffering from or susceptible to moderately to severely active rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase or a pharmaceutically acceptable salt thereof, or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In one embodiment, the disclosure is directed to a method of treating structural damage associated with rheumatoid arthritis in an adult subject, the method comprising once daily administration to the subject, particularly a human subject suffering from or susceptible to rheumatoid arthritis, of an extended-release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase or a pharmaceutically acceptable salt thereof equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in treating structural damage associated with rheumatoid arthritis in an adult subject, the use comprising once daily administration to the subject, particularly a subject suffering from or susceptible to structural damage associated with rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In one embodiment, the disclosure is directed to a method of reducing signs and symptoms of rheumatoid arthritis in an adult subject, the method comprising once daily administration to the subject, particularly a human subject suffering from or susceptible to moderately to severely active rheumatoid arthritis, of an extended-release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in reducing signs and symptoms associated with rheumatoid arthritis in an adult subject, the use comprising once daily administration to the subject, particularly a subject suffering from or susceptible to rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In the foregoing methods, in one embodiment, the pharmaceutically acceptable polymeric carrier comprises a release control polymer. In one embodiment, the release control polymer is hydroxypropylmethyl cellulose. In one embodiment, the dosage form comprises a pH modifier. In one embodiment, the pH modifier is tartaric acid. In one embodiment, the dosage form comprises from about 10 w/w % to about 35 w/w % tartaric acid. In one embodiment, the dosage form comprises about 10 w/w % tartaric acid. In one embodiment, the dosage form comprises about 20 w/w % tartaric acid. In one embodiment, the dosage form comprises about 30 w/w % tartaric acid.

In another embodiment the methods of the present disclosure further comprise administering Compound 1 or a solid-state form thereof for at least 8 weeks. In another embodiment, the methods of the present disclosure comprise administering Compound 1 or a solid-state form thereof for at least 12 weeks.

In another embodiment, the present disclosure relates to the use of a solid-state form of Compound 1 for treating a condition as described in the various embodiments of the present disclosure.

In another embodiment, the present disclosure relates to a solid-state form of Compound 1 for use in treatment of a condition as described in the various embodiments of the present disclosure.

Treatment of Giant Cell Arteritis (GCA)

Provided herein is a method of treating GCA with the selective JAK1 inhibitor, upadacitinib. The method generally comprises orally administering the upadacitinib to the patient daily for a period of time.

The presence of GCA in a patient may be determined by various clinical observations or imaging techniques. These include the presence of symptoms, indicative lab results, biopsy, angiography, or imaging via MRI or the like. In some embodiments, a patient with GCA exhibits a history of erythrocyte sedimentation rate (ESR)>=50 mm/hour. In some embodiments, a patient with GCA exhibits a history of high sensitivity C-reactive protein (hsCRP)/CRP>=1.0 mg/dL. In some embodiments, a patient with GCA exhibits unequivocal cranial symptoms of GCA such as pain and tenderness affecting both temples, headaches, scalp tenderness, jaw pain, and visual disturbances. In some embodiments, a patient with GCA has polymyalgia rheumatica (PMR). In some embodiments, a patient with GCA has undergone a temporal artery biopsy which revealed features of GCA. In some embodiments, the patient with GCA has evidence of large vessel vasculitis by angiography or cross-sectional imaging.

In some embodiments, the patient has active GCA. In some embodiments, the patient has relapsing GCA.

In some embodiments, the patient has not received any interleukin-6 (IL-6) inhibitor within 4 weeks prior to initiating the treatment or has not had a disease flare during prior treatment with an IL-6 inhibitor. In some embodiments, the patient has not received the IL-6 inhibitor Tocilizumab (Actemra®) within 4 weeks prior to initiating the treatment or has not had a disease flare during prior treatment with Tocilizumab. In some embodiments, the patient has not received a Janus Kinase (JAK) inhibitor prior to initiating the treatment. In some embodiments, the patient has not received the interleukin-1 receptor antagonist (IL-1Ra) anakinra (KINERET®) within 1 week prior to initiating the treatment. In some embodiments, the patient has not received methotrexate, hydroxychloroquine, cyclosporine, azathioprine, or mycophenolate within 4 weeks prior to initiating the treatment. In some embodiments, the patient has not received leflunomide within 8 weeks prior to initiating the treatment if no elimination procedure was followed. In some embodiments, the patient has not received cell-depleting agents or alkylating agents, including but not limited to cyclophosphamide, within 6 months prior to initiating the treatment.

In some embodiments, the patient does not have and has not previously had herpes zoster, herpes simplex, or human immunodeficiency virus (HIV). In some embodiments, the patient does not have active tuberculosis, an active or chronic recurring infection, or active hepatitis B or C.

GCA affects adults only, and generally those 50 years of age or older. Typically, patients develop signs and symptoms between the ages of 70 and 80. Accordingly, in some embodiments, the patient is 50 years old or older, such as about 50, about 55, about 60, about 65, about 70, about 75, about 80, about 85, or about 90.

In some embodiments, the dose is orally administered once daily in an amount of 7.5 mg. In some embodiments, the dose is orally administered once daily in an amount of 15 mg. In some embodiments, the administration is continued at the same dose and dosing frequency over a treatment period.

In some embodiments, the patient with GCA is receiving, at the time of initiating the treatment, an oral corticosteroid such as prednisone. In some embodiments, the patient is receiving at least 20 mg of oral corticosteroid as a once daily dose. In some embodiments, the patient is receiving 20 mg, 30 mg, 40 mg, 50 mg, or 60 mg as a once daily oral dose. In some embodiments, the method further comprises tapering down the dose of corticosteroid during the period the patient is treated with upadacitinib. In some embodiments, the oral corticosteroid is tapered down according to the 26-week CS taper regimen in Table A. In some embodiments, the oral corticosteroid is tapered down according to the 52-week CS taper regimen in Table A. In some embodiments, the dose of the oral corticosteroid is tapered down to 0 mg over 26 weeks.

The duration of the treatment period may vary. For example, the treatment period may be at least one month, such as 3 months, 4 months, 6 months, 9 months, 1 year, 2 years, 5 years, 10 years, 20 years, 50 years, or more. In some embodiments, the treatment period is 12 weeks. In some embodiments, the treatment period is 26 weeks. In some embodiments, the treatment period is 52 weeks. In some embodiments, the treatment period is at least 12 weeks, at least 26 weeks, or at least 52 weeks.

In some embodiments, the complete remission is sustained through week 52 after the first daily administration.

In some embodiments, the patient achieves a reduction in cumulative exposure to corticosteroids through week 52 after the first daily administration, relative to a patient that has not been treated with upadacitinib.

In some embodiments, the patient achieves an increase in time to disease flare through week 52 after the first daily administration, relative to a patient that has not been treated with upadacitinib. As used herein, the term "disease flare" means recurrence of GCA signs or symptoms or an erythrocyte sedimentation rate (ESR) measurement >30 mm/hr (attributable to GCA); and which requires an increase in corticosteroid dose. In some embodiments, the patient achieves a reduction in a number of disease flares through week 52 after the first daily administration, relative to a patient that has not been treated with upadacitinib.

In some embodiments, the patient achieves, relative to a patient that has not been treated with upadacitinib, a positive change from baseline in a 36-item Short Form Quality of Life Questionnaire (SF-36) Physical Component Score (PCS). The SF-36 is a generic health-related quality-of-life instrument that can be used across age, disease and treatment groups and includes 8 domains: physical functioning, role limitations due to physical health problems, role limitations due to emotional health problems, social functioning, pain, energy/fatigue, emotional well-being, and general health problems.

In some embodiments, the patient achieves, relative to a patient that has not been treated with upadacitinib, a positive change from baseline in a Functional Assessment of Chronic Illness Therapy-Fatigue (FACIT-Fatigue). The FACIT-Fatigue is a 13-item electronic-patient reported outcome (ePRO) measure of fatigue, which has been validated in the general population and in other chronic diseases. The FACIT-Fatigue content and measurement validity and related reliability has been extensively tested in the psoriatic arthritis (PsA) population, with evidence of reliability, construct validity, and responsiveness.

In some embodiments, the patient achieves, relative to a patient that has not been treated with upadacitinib, a positive change from baseline in an Assessment of Treatment Satisfaction Questionnaire for Medication (TSQM) Patient Global Satisfaction Subscale. The Treatment Satisfaction Questionnaire for Medications (TSQM) is a generic ePRO measure of treatment satisfaction, developed to compare treatment satisfaction between medication types and conditions. TSQM comprises of 14 items to assess 4 domains (effectiveness, side effects, convenience, and global satisfaction). The TSQM items are rated on a Likert scale (1=extremely dissatisfied to 7=extremely satisfied). Scores for each of the 4 domains range from 0 to 100, with higher scores corresponding to higher satisfaction.

III. Combination Therapy and Fixed-Dose Combinations

The present disclosure further relates to (i) methods of treatment and uses as previously described that further comprise the administration of one or more additional therapeutic agents (i.e., combination therapies), and (ii) pharmaceutical compositions as previously described that further comprise one or more additional therapeutic agents (i.e., fixed-dose combinations). When administered to a subject in combination with one or more additional therapeutic agents, the solid-state form of Compound 1 and the additional therapeutic agent(s) can be administered as separate dosage forms or as a single dosage form comprising the solid-state form of Compound 1 and the additional therapeutic agent(s). If administered as a separate dosage form, the additional therapeutic agent may be administered either simultaneously with, or sequentially with, the dosage form comprising the solid-state form of Compound 1.

For example, the solid-state forms of the present disclosure may be administered in a pharmaceutically acceptable form either alone or in combination with one or more additional agents that modulate a mammalian immune system or with anti-inflammatory agents. These agents may include but are not limited to cyclosporin A (e.g., SANDIMMUNE® or NEORAL®), rapamycin, FK-506 (tacrolimus), leflunomide, deoxyspergualin, mycophenolate (e.g., CELLCEPT®), azathioprine (e.g., IMURAN®), daclizumab (e.g., ZENAPAX®), OKT3 (e.g., ORTHOCLONE®), AtGam, aspirin, acetaminophen, aminosalicylate, ciprofloxacin, corticosteroid, metronidazole, probiotic, tacrolimus, ibuprofen, naproxen, piroxicam, and anti-inflammatory steroids (e.g., prednisolone or dexamethasone). In certain embodiments, the one or more additional agents are selected from the group consisting of aspirin, acetaminophen, aminosalicylate, ciprofloxacin, corticosteroid, cyclosporine, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, penicillamine, sulfasalazine, leflunomide, tocilizumab, anakinra, abatacept, certolizumab pegol, golimumab, vedolizumab, natalizumab, ustekinumab, rituximab, efalizumab, belimumab, etanercept, infliximab, adalimumab, and immune modulator (e.g., activator) for CD4+CD25+ Treg cells.

Non-limiting examples of therapeutic agents for rheumatoid arthritis with which a compound of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L). Combinations of therapeutic agents may interfere at different points in the autoimmune and subsequent inflammatory cascade. Such examples may include TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11.

The solid-state form may also be combined with nonbiologic DMARDS or other agents, such as methotrexate, 6-mercaptopurine, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, and 6-mercaptopurines. The solid-state form may also be combined with methotrexate.

Non-limiting examples of therapeutic agents for inflammatory bowel disease (IBD) with which the solid-state form can be combined may include (but are not limited to) the following: budesonide; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate;

cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g., NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g., IL-4, IL-10, IL-11, IL-13 and TGFB). The solid-state form may also be combined with methotrexate.

Examples of therapeutic agents for Crohn's disease with which the solid-state form can be combined include the following: TNF antagonists, for example, anti-TNF antibodies, adalimumab (such as HUMIRA™ brand adalimumab), infliximab such as CA2 (REMICADE™ brand infliximab), certolizumab pegol such as CIMZIA™, golimumab such as SIMPONI™ (golimumab), CDP 571, TNFR-Ig constructs, etanercept such as p75TNFR1gG (ENBREL™ brand etanercept) and lenercept such as p55TNFR1gG (Lenercept™) inhibitors and PDE4 inhibitors.

The solid-state form can be combined with corticosteroids, for example, budesonide and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis (MS) with which the solid-state form can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of the invention can be combined with antibodies to cell surface molecules such as CD2, CD3, CD4, CD8, CD19, CD20, CD25, CD28, CD30, CD40, CD45, CD69, CD80, CD86, CD90 or their ligands. The solid-state form may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFB). Examples of therapeutic agents for multiple sclerosis in which a compound of the invention can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The solid-state form may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis (AS) with which the solid-state form can be combined include the following: ibuprofen, diclofenac, misoprostol, naproxen, meloxicam, indomethacin, diclofenac, celecoxib, rofecoxib, sulfasalazine, methotrexate, azathioprine, minocycline, prednisone, and anti-TNF antibodies, adalimumab (such as HUMIRA™ brand adalimumab), infliximab such as CA2 (REMICADE™ brand infliximab), CDP 571, TNFR-Ig constructs, etanercept such as p75TNFR1gG (ENBREL™ brand etanercept) and lenercept such as p55TNFR1gG (LENERCEPT™).

Non-limiting examples of therapeutic agents for psoriasis (Ps, such as moderate to severe plaque psoriasis) with which the solid-state form can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, ustekinumab, and adalimumab (such as HUMIRA™ brand adalimumab).

Non-limiting examples of therapeutic agents for psoriatic arthritis (PsA) with which the solid-state form can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab (such as HUMIRA™ brand adalimumab), and efalizumab.

Examples of therapeutic agents for SLE (Lupus) with which the solid-state form can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budesonide, dexamethasone; cytotoxics, for example, azathioprine, cyclophosphamide, mycophenolate mofetil, methotrexate; inhibitors of PDE4 or purine synthesis inhibitor, for example CELLCEPT®. The solid-state form may also be combined with agents such as sulfasalazine, 5-aminosalicylic acid, olsalazine, IMURAN® and agents which interfere with synthesis, production or action of proinflammatory cytokines such as IL-1, for example, caspase inhibitors like IL-1β converting enzyme inhibitors and IL-1ra. The solid-state form may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The solid-state form can be combined with IL-11 or anti-cytokine antibodies, for example, fontolizumab (anti-IFNg antibody), or anti-receptor receptor antibodies, for example, anti-IL-6 receptor antibody and antibodies to B-cell surface molecules. The solid-state form may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab (such as HUMIRA™ brand adalimumab), infliximab such as CA2 (REMICADE™ brand infliximab), CDP 571, TNFR-Ig constructs, etanercept such as p75TNFR1gG (ENBREL™ brand etanercept) and lenercept such as p55TNFR1gG (LENERCEPT™).

The solid-state form may also be combined with an immune modulator for CD4+CD25+ Treg cells. Treg cells are essential for maintaining normal immune homeostasis. In patients with autoimmune diseases, reduced numbers or functional impairment of Treg cells has been observed, leading to loss of this finely-tuned mechanism. A humanized agonistic monoclonal antibody, BT-061, binds to a unique epitope of human CD4, and induces Treg-specific signaling events that lead to their functional activation. Pre-clinical data using isolated Treg cells and rheumatoid arthritis synovial fluid indicate that BT-061 leads to suppression of CD4+ and CD8+T effector cell proliferation, reduction of the expression of pro-inflammatory cytokines, and increase in the production of the anti-inflammatory cytokine TGFβ. Thus similar immune modulators for CD4+CD25+ Treg cells can also be co-administered with a compound of the invention for treating any of the inflammatory disease/ disorder, or an autoimmune disease/disorder described herein, including but not limited to rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, or atopic dermatitis. In certain embodiments, the combination treats rheumatoid arthritis, Crohn's disease, psoriasis, or psoriatic arthritis, including moderately to severely active rheumatoid arthritis, Crohn's disease, psoriasis, or psoriatic arthritis. In certain embodiments, the rheumatoid arthritis, Crohn's disease, psoriasis, or psoriatic arthritis patient being treated has inadequately responded to or has discontinued therapy due to loss of response to or intolerance to a first line therapy (such as a DMARD, including methotrexate) or an anti-TNFα therapy.

In certain embodiments, the immune modulator has one or more (or all) of the following properties: (1) activates a subset of CD4+ T cells comprising CD4+CD25+ regulatory T cells (Treg), or CD4+CD25+ Treg cells; (2) binds only to a special epitope of the human CD4 antigen (such as the IgG-like C2 type 1 domain of CD4), which said epitope of human CD4 may be bound by a mouse IgG1 anti-CD4 monoclonal antibody B-F5 or a humanized version thereof, such as the BT-061 hB-F5 antibody tregalizumab as described in U.S. Pat. No. 7,452,981 (incorporated herein by reference, including all sequences of the VH and VL chains disclosed therein); (3) provides an activation signal to naturally occurring Treg cells but does not activate conventional T cells (e.g., CD4+ T cells that are not activated in (1), CD8+ cytotoxic T cells, etc.); and (4) is not a depleting anti-CD4 antibody that depletes CD4+ T cells, and/or does not appreciably trigger ADCC or CDC.

IV. Dosages and Dosing

In certain embodiments, the methods of the present disclosure comprise administering to an adult subject (e.g., a human subject) Compound 1 (freebase), or a pharmaceutically acceptable salt thereof, or a crystalline hydrate of Compound 1 in an amount sufficient to deliver to the subject 15 mg of Compound 1 freebase equivalent. In one embodiment, the freebase or the hydrate is in a once daily extended-release formulation.

In certain embodiments, the methods of the present disclosure comprise administering to an adult subject (e.g., a human subject) 30 mg of Compound 1 (freebase), or a pharmaceutically acceptable salt thereof or a crystalline hydrate of Compound 1 in an amount sufficient to deliver to the subject 30 mg of Compound 1 freebase equivalent. In one embodiment, the freebase or the hydrate is in a once daily extended-release formulation.

EXAMPLES

Examples 1-4: Extended-Release Tablets

The Freebase Hydrate Form C and Amorphous Freebase solid-state forms of Compound 1 were formulated into 24 mg extended-release tablets according to the formulations set forth in Table 2.

TABLE 2

| | | | | | |
|---|---|---|---|---|---|
| Extended-Release Tablets (no pH modifier) | | | | | |
| Component | Function | Ex. 1 (ER1) (mg) | Ex. 2 (ER2) (mg) | Ex .3 (ER3) (mg) | Ex. 4 (mg) |
| Freebase Hydrate Form C | Active | 24.0 | 24.0 | 24.0 | — |
| Amorphous Freebase | Active | — | — | — | 24.0 |
| Microcrystalline cellulose (Avicel ® PH 102) | Filler | 351.4 | 303.4 | 303.4 | 303.4 |
| HPMC (Methocel ® K100 Premium LVCRLH) | Release control polymer | 96.0 | 96.0 | — | — |
| HPMC (Methocel ® K4M Premium CR) | Release control polymer | — | 48.0 | 144.0 | 144.0 |
| Colloidal silicon dioxide | Glidant | 3.8 | 3.8 | 3.8 | 3.8 |
| Magnesium stearate impalpable powder | Lubricant | 4.8 | 4.8 | 4.8 | 4.8 |
| Uncoated weight of tablet | | 480.0 | 480.0 | 480.0 | 480.0 |

The formulations were prepared by combining and blending the active, microcrystalline cellulose, hydroxypropyl methyl cellulose (HPMC), and colloidal silicone dioxide. The blend was milled using a Mobil Mill fitted with a 610-micron screen. The magnesium stearate was screened through mesh #30 and was added to the bin and blended.

The lubricated granulation was compressed into 480 mg weight tablets using a rotary tablet press. The tablets may optionally be coated with any suitable film coating.

The effect of solid-state form on the dissolution profile of the tablets was evaluated. In particular, the dissolution profile of the Example 3 (containing Freebase Hydrate Form C as active) and Example 4 (containing Amorphous Freebase as active) tablets was evaluated at pH 6.8 (representative of the pH in the lower intestine). The dissolution test was carried out using the following dissolution parameters and conditions:

Apparatus: USP Dissolution Apparatus 2 and fraction collector

Medium: 900 mL of 50 mM sodium phosphate buffer solution, pH 6.8.

Temperature: 37° C.±0.5° C.

RPM: 75 RPM±4%

Filter: 35 μm PE filter, or equivalent, for automatic sampling

Sampling Times: 1, 2, 4, 6, 8, 10, 12, 16, and 20 Hours. Other samples may be taken at other times, as appropriate.

Sample Volume: 1.5 mL obtained automatically, without media replacement.

The medium used for the study was a 0.05 M sodium phosphate buffer solution, pH 6.8±0.05. The medium was prepared using an acid stage medium (0.1 N hydrochloric acid solution) and a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The medium was prepared by mixing 500 mL of the acid stage medium and 400 mL of buffer stage concentrate in an appropriate size container or directly in the dissolution vessel and adjusting the pH with 1 N phosphoric acid or 1 N sodium hydroxide, if the pH was not within 6.8±0.05.

For the dissolution test, one tablet each was added to a dissolution vessel containing 900 mL of the 0.05 M sodium phosphate buffer solution maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % of the labelled amount of active released (% LA Released) was calculated. The formulation containing Freebase Hydrate Form C (Example 3) as the active showed a slower rate of dissolution than the formulation containing Amorphous Freebase (Example 4) as the active at pH 6.8.

The dissolution profile of formulations comprising Freebase Hydrate Form C as an active was further evaluated at pH 6.8 and in a dual pH system. In particular, the dissolution profile of the Example 1 (ER1), Example 2 (ER2), and Example 3 (ER3) tablets at pH 6.8 was carried out as described above. The dissolution profile of the Examples 1-3 tablets was also carried out in a dual pH system using the following dissolution parameters and conditions:

Apparatus: USP Dissolution Apparatus 2 and fraction collector

Medium: Acid Stage: 500 mL of Acid Stage Medium (0.1 N hydrochloric acid solution)

Buffer Stage: 900 mL of 50 mM sodium phosphate buffer solution, pH 6.8.

Temperature: 37° C.±0.5° C.

RPM: 75 RPM±4%

Filter: 35 μm PE filter, or equivalent, for automatic sampling

Sampling Times: Acid Stage: 1 Hour

Buffer Stage: 2, 4, 6, 8, 10, 12, 16, and 20 Hours.

Other samples may be taken at other times, as appropriate.

Sample Volume: Acid: 1.5 mL obtained automatically, without media replacement.

The acid stage medium is a 0.1 N hydrochloric acid solution. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

For the dissolution test, one tablet each was added to a dissolution vessel containing 500 mL of a 0.1 N hydrochloric acid solution maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, maintained at 37° C. The dissolution test was continued, with the paddles remaining at a speed of 75 RPM. The sample filtrate was the sample preparation.

For the analysis of the sample, conventional liquid chromatography methods were utilized, wherein the % relative standard deviation (RSD) of peak areas was calculated for each set of six standard injections.

After the initial release at the low pH (representative of the pH in the stomach), release of the drug is slowed at the higher pH (representative of the pH in the lower intestine). Therefore, in order to achieve the desired bioavailability, a formulation which allowed pH independent release was required.

Examples 5-12: Extended-Release Tablets

The Freebase Hydrate Form C solid-state form of Compound 1 was formulated into 15 mg, 24 mg, or 30 mg extended-release tablets according to the formulations set forth in Table 3 using direct compression.

TABLE 3

| | | | | | | | Ex. 10 | | |
|---|---|---|---|---|---|---|---|---|---|
| | | | | | | | (mg) | Ex. 11 | Ex. 12 |
| | | Ex. 5 | Ex. 6 | Ex. 7 | Ex. 8 | Ex. 9 | (ER4, no | (mg) | (mg) |
| Component | Function | (mg) (ER7) | (mg) | (mg) | (mg) (ER8) | (mg) (ER4) | mannitol) | (ER5) | (ER6) |
|---|---|---|---|---|---|---|---|---|---|
| Freebase Hydrate Form C | Active | 15.4[a] | 15.4[a] | 15.4[a] | 30.7[b] | 24.6[c] | 24.6[c] | 24.6[c] | 24.6[c] |
| Microcrystalline cellulose (Avicel ® PH 102) | Filler | 162.4 | 162.4 | 162.4 | 147.1 | 158.0 | 210.6 | 282.6 | 258.6 |
| Mannitol (Pearlitol ® 100 SD) | Filler | 52.6 | 52.4 | — | 52.6 | 52.7 | — | — | — |
| Mannitol (Pearlitol ® 200 SD) | Filler | — | — | 52.4 | — | — | — | — | — |

Extended-Release Tablets (tartaric acid pH modifier)

TABLE 3-continued

Extended-Release Tablets (tartaric acid pH modifier)

| Component | Function | Ex. 5 (mg) (ER7) | Ex. 6 (mg) | Ex. 7 (mg) | Ex. 8 (mg) (ER8) | Ex. 9 (mg) (ER4) | Ex. 10 (mg) (ER4, no mannitol) | Ex. 11 (mg) (ER5) | Ex. 12 (mg) (ER6) |
|---|---|---|---|---|---|---|---|---|---|
| Tartaric acid | pH modifier | 144.0 | 144.0 | 144.0 | 144.0 | 144.0 | 144.0 | 96.0 | 96.0 |
| HPMC (Hypromellose 2208) | Release control polymer | 96.0 | — | — | 96.0 | — | | — | — |
| HPMC (Methocel ® K4M Premium CR) | Release control polymer | — | 96.0 | 96.0 | — | 96.0 | 96.0 | — | — |
| Carbopol ® 71G | Release control polymer | — | — | — | — | — | | 48.0 | 72.1 |
| Carbopol ® 971P | Release control polymer | — | — | — | — | — | | 24.0 | 24.0 |
| Colloidal silicon dioxide | Glidant | 2.4 | 2.4 | 2.4 | 2.4 | — | — | — | — |
| Magnesium stearate impalpable powder | Lubricant | 7.2 | 7.2 | 7.2 | 7.2 | 4.8 | 4.8 | 4.8 | 4.8 |
| Uncoated weight of tablet | | 480.0 | 479.8 | 479.8 | 480.0 | 480.1 | 480.0 | 480.0 | 480.1 |
| Opadry ® II Yellow (PVA based) | Film coat | 14.40 | — | — | 14.40 | — | — | — | — |
| Total weight of tablet | | 494.39 | | | 494.43 | — | — | — | — |

[a]Provides 15 mg of Compound 1 freebase equivalent.
[b]Provides 30 mg of Compound 1 freebase equivalent.
[c]Provides 24 mg of Compound 1 freebase equivalent.

The formulations were prepared by first milling the tartaric acid through a Fitz mill Model M5A, fitted with a 1512-0027 screen. The Freebase Hydrate Form C, microcrystalline cellulose, mannitol (when present), milled tartaric acid, release control polymer, and colloidal silicone dioxide (when present) were combined and blended. The blend was milled using a Mobil Mill fitted with a 610- or 1397-micron screen. The magnesium stearate was screened through mesh #30 and was then added to the bin and blended. The lubricated granulation was compressed into about 480 mg weight tablets using a rotary tablet press.

The Example 5 and 8 tablets were coated using a film coater, which sprayed a solution containing the Opadry® II Yellow film coat and purified water until 14.40 mg of coating had been applied to the tablets.

The dissolution profile of the Example 9 (ER4, 24 mg active), Example 10 (ER4, no mannitol, 24 mg active), Example 11 (ER5, 24 mg active), and Example 12 (ER6, 24 mg active) tablets was evaluated at pH 1.2, at pH 6.8, and in a dual pH system. The pH 6.8 study was performed as described above for Examples 3 and 4. For the dual pH study, an acid stage medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH. The mixture was diluted to 6 L with water and mixed. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6

L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

The dissolution test was carried out using the following dissolution parameters and conditions:

Apparatus: USP Dissolution Apparatus 2 and fraction collector

Medium: Acid Stage: 500 mL of Acid Stage Medium
   Buffer Stage: 900 mL of 50 mM sodium phosphate buffer solution, pH 6.8

Temperature: 37° C.±0.5° C.

RPM: 75 RPM±4%

Filter: 35 µm PE filter, or equivalent, for automatic sampling

Sampling Times: Acid Stage: 1 Hour
   Buffer Stage: 2, 4, 6, 8, 10, 12, 16, and 20 Hours.
   Other samples may be taken at other times, as appropriate.

Sample Volume: Acid and Buffer Stage: 1.5 mL obtained automatically, without media replacement.

For the dissolution test, one tablet each was added to a dissolution vessel containing 500 mL of the acid stage medium, maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, and then the mixture was maintained at 37° C. The dissolution test was continued, with the paddles remaining at a speed of 75 RPM. The sample filtrate was the sample preparation.

For the pH 1.2 study, the dissolution test was carried out using the following dissolution parameters and conditions:

Apparatus: USP Dissolution Apparatus 2 and fraction collector

Medium: 500 mL of Acidic Medium, pH 1.2

Temperature: 37° C.±0.5° C.

RPM: 75 RPM±4%

Filter: 35 μm PE filter, or equivalent, for automatic sampling

Sampling Times: 1, 2, 4, 6, 8, 10, 12, 16, and 20 Hours. Other samples may be taken at other times, as appropriate.

Sample Volume: 1.5 mL obtained automatically, without media replacement.

For this study, an acidic medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH of 1.2. The mixture was diluted to 6 L with water and mixed.

For the dissolution test, one tablet each was added to a dissolution vessel containing 500 mL of the acidic medium, maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % relative standard deviation (RSD) of peak areas was calculated for each set of six standard injections. The results shown that pH independence is achieved in the once daily formulations.

The dissolution profile of the Example 5 (ER7), Example 8 (ER8), and Example 9 (ER4) tablets were evaluated in a dual pH system, as described above. The formulations provide an extended-release profile of 80-100% over a period of about 8-10 hours.

The formulations of Examples 5 and 8-12 all exhibited pH independent release of the active ingredient. In contrast, after the initial release at the low pH, release of the active is slowed at the higher pH for the formulations of Examples 1-3. Without wishing to be bound to any particular theory, it is believed that the inclusion of tartaric acid as a pH modifier in the Example 5 and 8-12 formulations contributed to the pH independent release observed for these tablets.

Example 13: Extended Release Tablet

The Freebase Hydrate Form C solid-state form of Compound 1 was formulated into a 7.5 mg extended-release tablet according to the formulation set forth in Table 4.

TABLE 8

| Extended Release Tablets (tartaric acid pH modifier) | | |
| --- | --- | --- |
| Component | Function | Ex. 13 (mg) (ER9) |
| Freebase Hydrate Form C* | Active | 7.678[a] |
| Microcrystalline cellulose (Avicel ® PH 102) | Filler | 170.1 |
| Mannitol (Pearlitol ® 100 SD) | Filler | 52.62 |
| Tartaric acid (crystalline) | pH modifier | 144.0 |
| HPMC (Hypromellose 2208) | Release control polymer | 96.0 |
| Colloidal silicon dioxide | Glidant | 2.4 |
| Magnesium stearate | Lubricant | 7.2 |
| Uncoated weight of tablet | | 479.998 |
| Opadry ® II Yellow | Film coat | 14.40 |
| Purified water | Processing aid | n/a |
| Total weight of tablet | | 494.398 |

[a]Provides 7.5 mg of Compound 1 freebase equivalent.

The formulation was prepared by first milling the tartaric acid through a Fitz mill Model M5A, fitted with a 1512-0027 screen. The Freebase Hydrate Form C, microcrystalline cellulose, mannitol, milled tartaric acid, release control polymer, and colloidal silicone dioxide were combined and blended. The blend was milled using a Mobil Mill fitted with a 610-micron screen. The magnesium stearate was screened through mesh #30 and was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Examples 14-19: Extended-Release Tablets

The Freebase Hydrate Form C solid-state form of Compound 1 was formulated into 15 mg or 30 mg extended-release tablets according to the formulations set forth in Table 5. The tablets were prepared using a wet granulation process, and were compressed into tablets having a core weight of about 480 mg.

TABLE 5

| Extended-Release Tablets (tartaric acid pH modifier) | | | | | | | |
| --- | --- | --- | --- | --- | --- | --- | --- |
| Component | Function | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
| Tablet Core (Intragranular) | | | | | | | |
| Freebase Hydrate Form C | Active | 30.7[a] | 30.7[a] | 30.7[a] | 15.4[b] | 15.4[b] | 15.4[b] |
| Microcrystalline cellulose | Filler | 79.9 | 79.9 | 79.9 | 40.0 | 40.0 | 40.0 |

TABLE 5-continued

| | | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
|---|---|---|---|---|---|---|---|
| Component | Function | | | | | | |

Extended-Release Tablets (tartaric acid pH modifier)

| Component | Function | Ex. 14 (ER10) | Ex. 15 (ER11) | Ex. 16 (ER12) | Ex. 17 (ER13) | Ex. 18 (ER14) | Ex. 19 (ER15) |
|---|---|---|---|---|---|---|---|
| (Avicel ® PH 101) HPMC (Hypromellose 2208) Tablet Core (Extragranular) | Release control polymer | 9.5 | 9.5 | 9.5 | 4.8 | 4.8 | 4.8 |
| Microcrystalline cellulose (Avicel ® PH 102) | Filler | 67.2 | 67.2 | 67.2 | 122.5 | 122.5 | 122.5 |
| Mannitol | Filler | 52.6 | 100.6 | 148.6 | 52.6 | 100.6 | 148.6 |
| Tartaric acid (crystalline) | pH modifier | 144.0 | 96.0 | 48.0 | 144.0 | 96.0 | 48.0 |
| HPMC (Hypromellose 2208) | Release control polymer | 86.5 | 86.5 | 86.5 | 91.2 | 91.2 | 91.2 |
| Colloidal silicon dioxide/silica | Glidant | 2.4 | 2.4 | 2.4 | 2.4 | 2.4 | 2.4 |
| Magnesium stearate | Lubricant | 7.2 | 7.2 | 7.2 | 7.2 | 7.2 | 7.2 |
| Uncoated weight of tablet | | 480.0 | 480.0 | 480.0 | 480.1 | 480.1 | 480.1 |
| Opadry ® II Yellow[c] | Film coat | 14.4 | 14.4 | 14.4 | 14.4 | 14.4 | 14.4 |
| Total weight of tablet | | 494.4 | 494.4 | 494.4 | 494.5 | 494.5 | 494.5 |

[a]Provides 30 mg of Compound 1 freebase equivalent.
[b]Provides 15 mg of Compound 1 freebase equivalent.
[c]Film coat weight is approximate.

The formulation was prepared by first milling the tartaric acid through a Fitz mill Model M5A, fitted with a 1512-0027 screen. The intragranular portion of the hydroxypropylmethyl cellulose release control polymer, the Freebase Hydrate Form C, and intragranular portion of the microcrystalline cellulose filler were added to a granulator, and mixed. Water was sprayed to granulate. The granulated material was then dried and milled using a comill fitted with a 610-micron screen. The milled granulation was then added to the extragranular tablet components other than magnesium stearate and sieved using a comill fitted with a 1397-micron screen, followed by blending. The magnesium stearate was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Example 20: Evaluation of the Effect of Organic Acids on Dissolution Profile of Extended-Release Tablets In this example, the effect of various organic acid pH modifiers (e.g., tartaric acid, citric acid, succinic acid, and fumaric acid) on the release rate of Freebase Hydrate Form C from 24 mg once-daily extended-release (ER) tablets was evaluated. Freebase Hydrate Form C was formulated into 24 mg Extended-Release tablets according to the formulations set forth in Table 6.

TABLE 6

Extended Release Tablets

| Component | Function | Tartaric acid A | Tartaric acid B | Citric acid C | Citric acid D | Succinic acid E | Succinic acid F | Fumaric acid G | Fumaric acid H |
|---|---|---|---|---|---|---|---|---|---|
| Freebase Hydrate Form C | Active | 24.6 | 24.6 | 24.6 | 24.6 | 24.6 | 24.6 | 24.6 | 24.6 |
| Microcrystalline cellulose (Avicel ® PH102) | Filler | 306.6 | 306.6 | 306.6 | 306.6 | 306.6 | 306.6 | 306.6 | 306.6 |
| HPMC (Methocel ® K4M) | Release control polymer | 96.0 | — | 96.0 | — | 96.0 | — | 96.0 | — |
| Carbopol ® 71G | Release control polymer | — | 96.0 | — | 96.0 | — | 96.0 | — | 96.0 |

TABLE 6-continued

| | | Tartaric acid | | Citric acid | | Succinic acid | | Fumaric acid | |
|---|---|---|---|---|---|---|---|---|---|
| | | \multicolumn{10}{c}{Extended Release Tablets} | | | | | | | |
| Component | Function | A | B | C | D | E | F | G | H |
| Organic acid | pH modifier | 48.0 | 48.0 | 48.0 | 48.0 | 48.0 | 48.0 | 48.0 | 48.0 |
| Magnesium stearate | Lubricant | 4.8 | 4.8 | 4.8 | 4.8 | 4.8 | 4.8 | 4.8 | 4.8 |
| Total | | 480.0 | 480.0 | 480.0 | 480.0 | 480.0 | 480.0 | 480.0 | 480.0 |

The formulations were prepared by first milling the organic acid through a Fitz mill Model M5A, fitted with a 1512-0027 screen. The active, microcrystalline cellulose, milled organic acid, and release control polymer, were combined and blended. The blend was milled using a Mobil Mill fitted with a 610-micron screen. The magnesium stearate was screened through mesh #30 and was added to the bin and blended. The lubricated granulation was compressed into 480 mg weight tablets using a rotary tablet press.

The effect of the organic acids on the dissolution profile of the tablets was evaluated at pH 1.2 and pH 6.8. The dissolution tests were carried out using the dissolution parameters and conditions as described above in Examples 3 and 4 and 9-12. For analysis of the sample, conventional liquid chromatography methods were utilized, wherein the % of the labelled amount of active released (% LA Released) was calculated. The results show that organic acids improved dissolution rate at high pH, with tartaric acid showing the best improvement. The formulations comprising the control release polymer Carbopol® with tartaric acid provided near linear release at pH 6.8.

Example 21: Gel pH Measurements for Tablets with Different Amounts of Tartaric Acid To measure the pH of the environment created when Compound 1 reacts with HPMC, the following experiment was performed.

The Freebase Hydrate Form C solid-state form of Compound 1 was formulated into 30 mg extended-release tablets according to the formulations set forth in Table 7A. The tablets were prepared using a wet granulation process, as described in Examples 14-19.

Dissolution media of 0.01 N HCl (pH 2) and 113 mM sodium phosphate buffer (pH 6.8) was prepared at 37° C. One tablet was added to 500 mL of 0.01 N HCl media and stirred at 75 rpm at 37° C. for one hour in a Vankel VK 7010 dissolution bath. Then 400 mL of sodium phosphate buffer was added. The solution was stirred an additional three hours. The tablet was removed, rinsed with water and dried using laboratory tissues. The gel that formed on the tablet was separated from the dry core for pH measurement. This procedure was repeated three times for each formulation. The pH of the gel formed on the tablets is set forth in Table 7B.

TABLE 7A

| | Formulation 1 mg/tab | Formulation 2 mg/tab | Formulation 3 mg/tab | Formulation 4 mg/tab | Formulation 5 mg/tab |
|---|---|---|---|---|---|
| Component | \multicolumn{5}{c}{Formulations} | | | | |
| | \multicolumn{5}{c}{Intragranular} | | | | |
| Freebase Hydrate Form C | 30.71 | 30.71 | 30.71 | 30.71 | 30.71 |
| HPMC (Methocel ® K4M) | 3.920 | 3.920 | 3.920 | 3.920 | 3.920 |
| Microcrystalline cellulose (Avicel ® PH102) | 30.71 | 30.71 | 30.71 | 30.71 | 30.71 |
| | \multicolumn{5}{c}{extragranular} | | | | |
| Microcrystalline cellulose (Avicel ® PH102) | 116.4 | 164.4 | 188.4 | 212.4 | 260.4 |
| Tartaric Acid (milled) | 144.0 | 96.00 | 72.00 | 48.00 | 0.00 |
| Mannitol (Pearlitol ® 100SD) | 52.62 | 52.62 | 52.62 | 52.62 | 52.62 |
| HPMC (Methocel ® K4M) | 92.08 | 92.08 | 92.08 | 92.08 | 92.08 |

TABLE 7A-continued

| | Formulations | | | | |
|---|---|---|---|---|---|
| Component | Formulation 1 mg/tab | Formulation 2 mg/tab | Formulation 3 mg/tab | Formulation 4 mg/tab | Formulation 5 mg/tab |
| Colloidal silicon dioxide | 2.400 | 2.400 | 2.400 | 2.400 | 2.400 |
| Magnesium Stearate | 7.200 | 7.200 | 7.200 | 7.200 | 7.200 |
| Total | 480.04 | 480.04 | 480.04 | 480.04 | 480.04 |

TABLE 7B

| | pH Results | | | | |
|---|---|---|---|---|---|
| Formulation | % Tartaric Acid | $1^{st}$ tablet | $2^{nd}$ tablet | $3^{rd}$ tablet | Average |
| 1 | 30 | 2.63 | 2.68 | 2.81 | 2.71 |
| 2 | 20 | 3.17 | 3.09 | 3.23 | 3.16 |
| 3 | 15 | 3.42 | 3.94 | 3.65 | 3.67 |
| 4 | 10 | 3.88 | 3.67 | 3.77 | 3.77 |
| 5 | 0 | 6.26 | 6.21 | 6.55 | 6.34 |

Example 22: Evaluation of the In Vivo Pharmacokinetic Profile of 15 mg Extended-Release Tablets (Fasting)

The pharmacokinetic profile of the 15 mg once-daily extended-release (ER) tablets prepared in Example 5 was evaluated and compared to that of a 12 mg immediate-release (IR) capsule comprising Tartrate Hydrate as the active.

Healthy human subjects (n=11) were administered a single dose of the 12 mg IR capsule (Regimen A) and the 15 mg ER (once-daily) tablet from Example 5 (Regimen B) under fasting conditions in a randomized, two-period, cross-over study design. Subjects were administered Regimen A in the first study period and Regimen B in the second study period or administered Regimen B in the first study period and Regimen A in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 8A.

TABLE 8A

Mean (% CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $C_{max}$ | ng/mL | 64.6 (16) | 26.0 (37) |
| $T_{max}$[a] | hours | 1.0 (0.5-1.5) | 3.0 (1.0-4.0) |
| $t_{1/2}$[b] | hours | 9.2 (119) | 12.5 (90) |

TABLE 8A-continued

Mean (% CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $AUC_t$ | ng · h/mL | 231 (15) | 227 (26) |
| $AUC_{inf}$ | ng · h/mL | 234 (15) | 242 (26) |

[a]Median (minimum, maximum)
[b]Harmonic mean (pseudo-% CV)
[c]Data in parentheses is coefficient of variance of the PK parameter (% CV), unless otherwise indicated.

As can be seen from this data, the 15 mg ER tablet provided a lower Cmax and comparable AUC to the 12 mg IR capsule under fasting conditions.

The relative bioavailability for a single dose of the once-daily (ER) tablet formulation (Regimen B) relative to the IR capsule formulation (Regimen A) was also determined based on analysis of the natural logarithms of $C_{max}$ and AUC. The results are summarized in Table 8B below.

TABLE 8B

Relative Bioavailability and 90% Confidence Intervals for Bioequivalence Assessment

| PK Parameter | Relative Bioavailability | |
|---|---|---|
| | Point Estimate | 90% Confidence Interval |
| $C_{max}$ | 0.373 | 0.312-0.446 |
| $AUC_t$ | 0.939 | 0.869-1.013 |
| $AUC_{inf}$ | 0.992 | 0.909-1.082 |

For Regimen B versus Regimen A, the point estimates for the ratios of $AUC_t$ and $AUC_{inf}$ were near unity, and the 90% confidence intervals were within the 0.86-1.09 range.

Example 23: Evaluation of the In Vivo Pharmacokinetic Profile of 30 mg Extended-Release Tablets (Fasting)

The pharmacokinetic profile of the 30 mg once daily extended-release (ER) tablets prepared in Example 8 was evaluated and compared to that of a 24 mg dose of an immediate release (IR) capsule comprising Tartrate Hydrate as the active.

Healthy human subjects (n=12) were administered a single 24 mg dose (two 12 mg IR capsules) (Regimen C) and the 30 mg ER (once daily) tablet from Example 8 (Regimen D) under fasting conditions in a randomized, two-period, cross-over study design. Half the subjects were administered Regimen C in the first study period and Regimen D in the second study period, while the other half were administered Regimen D in the first study period and Regimen C in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 9A.

TABLE 9A

Mean (% CV)[c] Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
|---|---|---|---|
| $C_{max}$ | ng/mL | 176 (37) | 63.7 (33) |
| $T_{max}$[a] | hours | 0.5 (0.5-1.5) | 2.0 (1.5-4.0) |
| $t_{1/2}$[b] | hours | 9.9 (52) | 10.8 (67) |
| $AUC_t$ | ng · h/mL | 520 (25) | 477 (27) |
| $AUC_{inf}$ | ng · h/mL | 524 (25) | 491 (27) |

[a]Median (minimum-maximum)
[b]Harmonic mean (pseudo % CV)
[c]Data in parentheses is the coefficient of variance of the PK parameter (% CV), unless otherwise indicated.

As can be seen from this data, the 30 mg ER tablet provided a lower Cmax and comparable AUC to the 24 mg dose IR capsule (2×12 mg) under fasting conditions.

The relative bioavailability for a single dose of the once-daily (ER) tablet formulation (Regimen D) relative to the IR capsule formulations (Regimen C) was also determined based on analysis of the natural logarithms of $C_{max}$ and AUC. The results are summarized in Table 9B below.

TABLE 9B

Relative Bioavailability and 90% Confidence Intervals for Bioequivalence Assessment

| PK Paramenter | PK Value Regimen D | Regimen C (reference) | Relative Bioavailability Point Estimate | 90% Confidence Interval |
|---|---|---|---|---|
| $C_{max}$ | 63.7 | 176 | 0.368 | 0.326-0.415 |
| $AUC_t$ | 477 | 520 | 0.912 | 0.828-1.004 |
| $AUC_{inf}$ | 491 | 524 | 0.933 | 0.845-1.029 |

For Regimen D versus Regimen C, the point estimates for the ratios of $AUC_t$ and $AUC_{inf}$ were near unity, and the 90% confidence intervals were within the 0.82-1.03 range.

Example 24: Comparison of the In Vivo Pharmacokinetic Profile of 30 mg Extended-Release Tablets Under Fasting Versus Fed Conditions The pharmacokinetic profile of the 30 mg extended-release tablets prepared in Example 8 after a high-fat meal was evaluated, and compared to the pharmacokinetic profile of the 30 mg extended-release tablets under fasting conditions (see Example 23).

Following completion of the Example 23 study, the healthy human subjects (n=12) were administered single doses of the 30 mg ER (once daily) tablet from Example 8 after a high-fat meal (Regimen E). Serial blood samples were collected from each subject prior to dosing and for 72 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter, and compared to the pharmacokinetic parameters for the 30 mg tablets administered under fasting conditions (see Example 23, Regimen D). The results are summarized in Table 10A.

TABLE 10A

Mean (% CV)[c] Pharmacokinetic Parameters for Compound 1 Following Administration of 30 mg ER Tablet Under Fasting Conditions or After a High-Fat Meal

| PK Parameter | Units | Regimen D (Fasting) | Regimen E (After High-Fat Meal) |
|---|---|---|---|
| $C_{max}$ | ng/mL | 63.7 (33) | 76.8 (39) |
| $T_{max}$[a] | hours | 2.0 (1.5-4.0) | 4.0 (1.5-8.0) |
| $t_{1/2}$[b] | hours | 10.8 (67) | 11.9 (51) |
| $AUC_t$ | ng · h/mL | 477 (27) | 564 (26) |
| $AUC_{inf}$ | ng · h/mL | 491 (27) | 577 (27) |

[a]Median (minimum-maximum)
[b]Harmonic mean (pseudo-CV %)
[c]Data in parentheses is coefficient of variance of the PK parameter (% CV), unless otherwise indicated.

The relative bioavailability for a single dose of the once-daily (ER) 30 mg tablet formulation after a high-fat meal (Regimen E) relative to the bioavailability of the ER 30 mg tablet under fasting conditions (Regimen D) was also determined based on analysis of the natural logarithms of $C_{max}$ and AUC. The results are summarized in Table 10B below.

TABLE 10B

Relative Bioavailability and 90% Confidence Intervals for Bioequivalence Assessment

| PK Parameter | PK Value Regimen E (after high-fat meal) | Regimen D (fasting) | Relative Bioavailability Point Estimate | 90% Confidence Interval |
|---|---|---|---|---|
| $C_{max}$ | 76.8 | 63.7 | 1.197 | 1.027-1.395 |
| $AUC_t$ | 564 | 477 | 1.184 | 1.042-1.344 |
| $AUC_{inf}$ | 577 | 491 | 1.171 | 1.035-1.326 |

As can be seen from Tables 14A and 14B, there is no clinically meaningful food effect for the 30 mg ER tablets. Administration following a high-fat meal increased the Compound 1 mean AUC and $C_{max}$ by 17% and 20%, respectively.

Example 25: Observed Steady State Exposures for 15 mg and 30 mg Extended-Release Tablets Under Non-Fasting Conditions The steady state pharmacokinetic profile of the 15 mg once daily extended-release (ER) tablets (prepared in Example 5) and the 30 mg once daily ER tablets (prepared in Example 8) was evaluated.

Healthy human subjects (n=24) were assigned to one of two regimens. Subjects in Regimen F (n=12) were administered the 15 mg ER tablet from Example 5 once daily for seven days under non-fasting conditions. Subjects in Regimen G (n=12) were administered the 30 mg ER tablet from Example 8 once daily for seven days under non-fasting conditions. On days one and seven, serial blood samples were collected from each subject prior to the daily dosing and up to 24 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 11A.

Example 26: Observed Steady State Exposures for 15 mg Extended-Release Tablets and 6 mg Immediate Release Capsules Under Fasting Conditions The steady state pharmacokinetic profile of the 15 mg once daily extended-release (ER) tablets (prepared in Example 5) under fasting conditions was evaluated and compared to that of a 6 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=12) were administered the 15 mg ER tablet from Example 5 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma

TABLE 11A

Mean (% CV)[e] Pharmacokinetic Parameters for Compound 1 Following Administration of 15 mg ER Tablet or 30 mg ER Tablet QD for Seven Days (Non-Fasting)

| PK Parameter | Units | Regimen F (15 mg ER Tablet) | | Regimen G (30 mg ER Tablet) | |
| --- | --- | --- | --- | --- | --- |
| | | Day 1 | Day 7 | Day 1 | Day 7 |
| $C_{max}$ | ng/mL | 36.8 (26) | 36.0 (24) | 74.3 (32) | 79.5 (40) |
| $T_{max}$[a] | hours | 4.0 (3.0-6.0) | 4.0 (2.0-6.0) | 4.0 (2.0-6.0) | 4.0 (1.5-6.0) |
| $AUC_{24}$ | ng · h/mL | 305 (24) | 317 (21) | 517 (30) | 582 (30) |
| $C_{24}$ | ng/mL | 2.42 (45) | 3.22 (46) | 4.27 (48) | 5.25 (44) |
| $C_{trough}$ | ng/mL | — | 2.96 (35) | — | 5.02 (42) |
| $C_{min, ss}$ | ng/mL | — | 2.80 (41) | — | 4.62 (38) |
| Fluctuation Index | % | 291 (14) | 251 (14) | 345 (14) | 306 (17) |
| $t_{1/2}$[b] | hours | — | 9.43 (76) | — | 10.4 (44) |
| $C_{max}$ to $C_{24}$ ratio | | 17 (7.8-44) | 13 (5.6-35) | 17 (9.9-38) | 14 (7.0-30) |
| $C_{max}$/Dose | (ng/mL)/mg | 2.46 (26) | 2.40 (24) | 2.48 (32) | 2.65 (40) |
| $C_{trough}$/Dose | (ng/mL)/mg | 0.16 (45) | 0.21 (46) | 0.14 (48) | 0.18 (44) |
| $AUC_{24}$/Dose | (ng · h/mL)/mg | 20.3 (24) | 21.2 (21) | 17.2 (30) | 19.4 (30) |
| $R_{AUC}$[c] | | — | 1.02 (0.91-1.40) | — | 1.16 (0.92-1.31) |
| $R_{Cmax}$[d] | | — | 1.00 (0.84-1.26) | — | 1.02 (0.82-1.40) |

[a]Median (minimum-maximum)

[b]Harmonic mean (pseudo-% CV)

[c]$R_{AUC}$ = $AUC_{24}$ Day 7/$AUC_{24}$ Day 1; median (range)

[d]$R_{Cmax}$ = $C_{max}$ Day 7/$C_{max}$ Day 1; median (range)

[e]Data in parentheses is the coefficient of variance of the PK parameter (% CV), unless otherwise indicated As can be seen from this data, the observed steady state $C_{max}$ and $AUC_{24}$ following 15 mg QD and 30 mg QD administration are generally consistent with the single dose and food-effect results obtained in Examples 22-24. The bioavailability of the 15 mg and 30 mg ER tablets is 70% to 80% relative to the same dose of IR capsules.

samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 12A.

TABLE 12A

Mean (% CV)$^e$ Pharmacokinetic Parameters for Compound 1 Following Administration of 6
mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
|---|---|---|---|---|---|
| | | Day 1 | Day 7 | Day 1 | Day 7 |
| $C_{max}$ | ng/mL | 36.5 (25) | 33.9 (26) | 31.7 (40) | 31.9 (35) |
| $T_{max}{}^a$ | hours | 1.0 (1.0-13) | 1.0 (0.5-14) | 3.0 (1.5-6.0) | 2.5 (1.5-4.0) |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/mL | 3.2 (36) | 3.6 (23) | 1.9 (42) | 3.1 (37) |
| $C_{min}$ | ng/mL | — | 2.7 (26) | — | 3.1 (37) |
| Fluctuation Index | % | 303 (13) | 259 (13) | 299 (22) | 246 (21) |
| $t_{1/2}{}^b$ | hours | — | 14.7 (77) | — | 10.3 (76) |
| $C_{max}$ to $C_{24}$ ratio$^a$ | — | 12 (7.7-19) | 8.8 (7.4-13) | 22 (5.8-43) | 12 (4.2-20) |
| $C_{max}$ to $C_{min}$ ratio$^a$ | — | — | 13 (8.3-18) | — | 12 (4.2-20) |
| $AUC_{24}$/Dose | (ng · h/mL)/ mg | 24.8 (23) | 24.0 (22) | 16.6 (29) | 18.6 (26) |
| $R_{AUC}{}^C$ | — | — | 1.02 (0.88-1.09) | — | 1.11 (0.87-1.99) |
| $R_{Cmax}{}^d$ | — | — | 0.97 (0.68-1.17) | — | 1.01 (0.65-3.01) |

$^a$Median (minimum-maximum)

$^b$Harmonic mean (pseudo-% CV)

$^c$$R_{AUC}$ = $AUC_{24}$ Day 7/$AUC_{24}$ Day 1; median (range)

$^d$$R_{Cmax}$ = $C_{max}$ Day 7/$C_{max}$ Day 1; median (range)

$^e$Data in parentheses is the coefficient of variance of the PK parameter (% CV), unless otherwise indicated The relative bioavailability for the once-daily (ER) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{24}$. The results are summarized in Table 12B below.

TABLE 12B

Relative Bioavailability Estimates and 90% Confidence
Intervals for 15 mg QD Tablets Relative to 6 mg BID
Capsules at Steady State under Fasting Conditions

| PK Paramenter | Relative Bioavailability | |
|---|---|---|
| | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state Cmin was approximately 1 for the 15 mg QD tablet relative to the 6 mg BID capsules.

The pre-morning dose trough concentration (Ctrough) for the 6 mg BID capsules and 15 mg QD tablets was determined prior to the morning dose on Days 2-8. At steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 27: Observed Steady State Exposures for
30 mg Extended-Release Tablets and 12 mg
Immediate Release Capsules Under Fasting
Conditions The steady state pharmacokinetic profile of the 30 mg once daily extended-release (ER) tablets (prepared in Example 8) under fasting conditions was evaluated and compared to that of a 12 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg ER tablet from Example 8 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 13A. The mean plasma concentration of Compound 1 at each time point measured for each of the two regimens is set forth in FIG. 22.

TABLE 13A

| | | Regimen M (12 mg IR Capsules (BID)) | | Regimen N (30 mg ER Tablet (QD)) | |
|---|---|---|---|---|---|
| PK Parameter | Units | Day 1 | Day 7 | Day 1 | Day 7 |
| $C_{max}$ | ng/mL | 80.8 (23) | 73.9 (19) | 65.7 (22) | 68.2 (30) |
| $T_{max}{}^a$ | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/mL | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/mL | — | 3.8 (58) | — | 3.8 (43) |
| Fluctuation Index | % | 388 (15) | 317 (14) | 349 (12) | 291 (17) |
| $t_{1/2}{}^b$ | hours | — | 7.3 (60) | — | 14.4 (64) |
| $C_{max}$ to $C_{24}$ ratio$^a$ | — | 15 (5.4-20) | 12 (5.9-16) | 29 (13-38) | 17 (4.1-33) |
| $C_{max}$ to $C_{min}$ ratio$^a$ | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}{}^c$ | — | — | 1.08 (0.97-1.18) | — | 1.11 (0.79-1.67) |
| $R_{Cmax}{}^d$ | — | — | 0.98 (0.65-1.18) | — | 1.03 (0.40-1.82) |

$^a$Median (minimum-maximum)

$^b$Harmonic mean (pseudo-% CV)

$^c$$R_{AUC}$ = $AUC_{24}$ Day 7/$AUC_{24}$ Day 1; median (range)

$^d$$R_{Cmax}$ = $C_{max}$ Day 7/$C_{max}$ Day 1; median (range)

$^e$Data in parentheses is the coefficient of variance of the PK parameter (% CV), unless otherwise indicated The relative bioavailability for a single dose of the once-daily (ER) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 13B below.

TABLE 13B

Relative Bioavailability Estimates and 90% Confidence Intervals for 30 mg QD Tablets Relative to 12 mg BID Capsules at Steady State under Fasting Conditions

| | Relative Bioavailability | |
|---|---|---|
| PK Paramenter | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

The ratio of steady-state AUC for the 30 mg QD tablets relative to the 12 mg BID capsules was approximately 1, with the 90% confidence intervals within the equivalence boundaries. The steady-state Cmin for the 30 mg QD tablet was approximately 13% lower than for the 12 mg BID capsules. Outliers with high Cmin in the 12 mg BID dose may have contributed to this difference.

The pre-morning dose trough concentration (Ctrough) for the 12 mg BID capsules and 30 mg QD tablets was determined prior to the morning dose on Days 2-8. The results show that, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 28: Comparison of AM Vs. PM Pharmacokinetic Profile Following Administration of 6 Mg or 12 mg Immediate Release Capsules Under Fasting Conditions The pharmacokinetic profile of the 6 mg immediate release (IR) twice daily (BID) capsules and the 12 mg IR twice daily capsules was determined on Day 7 of Regimen K (Example 26) and Regimen M (Example 27), respectively, after administration of the morning (AM dose) and evening (PM dose).

The results are summarized in Table 14.

TABLE 14

Mean (% CV)$^b$ Pharmacokinetic Parameters for Compound 1 Following Administration of AM and PM Doses of 6 mg and 12 mg Immediate Release Capsules on Day 7 (Fasting Conditions)

| | | Regimen K (6 mg IR Capsules) | | Regimen M (12 mg IR Capsules) | |
|---|---|---|---|---|---|
| PK Parameter | Units | AM Dose | PM Dose$^c$ | AM Dose | PM Dose$^c$ |
| $C_{max}$ | ng/mL | 33.6 (28) | 24.4 (22) | 73.9 (19) | 46.0 (26) |
| $T_{max}{}^a$ | hours | 1 (0.5-1.5) | 2 (1.0-3.0) | 1 (0.5-1.5) | 3 (1.0-4.0) |
| $AUC_{12}$ | ng · h/mL | 152 (26) | 153 (19) | 290 (19) | 244 (19) |

TABLE 14-continued

Mean (% CV)$^b$ Pharmacokinetic Parameters for Compound 1 Following Administration of AM
and PM Doses of 6 mg and 12 mg Immediate Release Capsules on Day 7 (Fasting Conditions)

| PK | | Regimen K (6 mg IR Capsules) | | Regimen M (12 mg IR Capsules) | |
|---|---|---|---|---|---|
| Parameter | Units | AM Dose | PM Dose$^c$ | AM Dose | PM Dose$^c$ |
| $C_{12}$ | ng/mL | 2.76 (24) | 3.63 (23) | 4.1 (55) | 6.94 (37) |
| $C_{max}/C_{12}$ | — | 12.3 (23) | 6.9 (22) | 18.0 (30) | 7.4 (39) |

$^a$Median (Minimum-Maximum)
$^b$Data in parentheses is the coefficient of variance of the PK parameter (% CV), unless otherwise indicated
$^c$The PM dose was administered 3 hours after starting dinner and 4 hours before a snack.

Example 29: Evaluation of the In Vivo Pharmacokinetic Profile of 30 mg Extended-Release Tablets The pharmacokinetic profiles of the 30 mg once-daily extended-release (ER) tablets that were prepared in Examples 14 (ER10, 30% tartaric acid), 15 (ER11, 20% tartaric acid), and 16 (ER12, 10% tartaric acid) using wet granulation were evaluated, and compared to that of the 30 mg ER tablet that was prepared in Example 8 (ER8, 30% tartaric acid) using direct compression (no wet granulation). The effect of a high-fat meal on the Example 14, 15, and 16 formulations was also evaluated.

Healthy human subjects (n=36) were administered a single dose of the 30 mg ER (once daily) tablet from Example 8 (ER8), Example 14 (ER10), Example 15 (ER11), and Example 16 (ER12) under fasting conditions or after a high-fat meal (non-fasting), in an open-label, randomized, four-period, incomplete crossover study. Doses in the four periods were separated by at least four days. Dosing regimens were as set forth below in Table 15A.

TABLE 15A-continued

| | Dosing Regimens | | |
|---|---|---|---|
| Regimen | Dose | Formulation | Fasting/Non-Fasting |
| C | Single 30 mg | Example 14 (ER10) | Non-Fasting |
| D | Single 30 mg | Example 15 (ER11) | Fasting |
| E | Single 30 mg | Example 15 (ER11) | Non-Fasting |
| F | Single 30 mg | Example 16 (ER12) | Fasting |
| G | Single 30 mg | Example 16 (ER12) | Non-Fasting |

Serial blood samples were collected from each subject prior to dosing and for 72 hours after dosing in each study period. Upon collection, the samples were promptly placed in an ice bath, and within 1 hour after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Bioavailability Under Fasting Conditions

The results for administration under fasting conditions are summarized in Table 15B.

TABLE 15B

Mean (% CV)$^c$ Pharmacokinetic Parameters for Compound 1 Following Administration of
a Single 30 mg Dose of Various Compound 1 Once-Daily Formulations Prepared Using
Wet Granulation Compared to Administration of a Single 30 mg Dose of a Compound
1 Once-Daily Formulation Prepared Via Direct Compression Under Fasting Conditions

| PK Parameter | Units | Regimen A (ER8) (n = 36) | Regimen B (ER10) (n = 24) | Regimen D (ER11) (n = 24) | Regimen F (ER12) (n = 24) |
|---|---|---|---|---|---|
| $C_{max}$ | ng/mL | 57.0 (33) | 55.8 (27) | 61.0 (25) | 58.6 (34) |
| $T_{max}$$^a$ | hours | 2.5 (1.0-4.0) | 3.0 (1.0-4.0) | 2.0 (1.0-4.0) | 2.0 (1.0-4.0) |
| $AUC_t$ | ng · h/mL | 495 (24) | 473 (24) | 487 (22) | 481 (23) |
| $AUC_{inf}$ | ng · h/mL | 513 (26) | 484 (24) | 499 (22) | 495 (23) |
| $t_{1/2}$$^b$ | hours | 9.2 (61) | 10.1 (50) | 9.0 (61) | 9.3 (63) |

$^a$Median (minimum-maximum)
$^b$Harmonic mean (pseudo-% CV)
$^c$Data in parentheses is coefficient of variance of the PK parameter (% CV), unless otherwise indicated.

TABLE 15A

| | Dosing Regimens | | |
|---|---|---|---|
| Regimen | Dose | Formulation | Fasting/Non-Fasting |
| A | Single 30 mg | Example 8 (ER8) | Fasting |
| B | Single 30 mg | Example 14 (ER10) | Fasting |

The relative bioavailability for a single dose of the three once-daily (ER) tablet formulations prepared using wet granulation (Regimens B, D, and F) relative to the ER tablet prepared via direct compression (no wet granulation) (Regimen A) was also determined based on analysis of the natural logarithms of $C_{max}$, $AUC_t$, and $AUC_{inf}$. The results are summarized in Table 15C below.

TABLE 15C

Bioavailability for Three Compound 1 Once-Daily Formulations Prepared Using Wet Granulation (30 mg; ER10, ER11, ER12) Relative to a Formulation Prepared Via Direct Compression (30 mg, ER8) under Fasting Conditions

| | | Relative Bioavailability | |
| Regimens | PK Parameter | Point Estimate | 90% Confidence Interval |
| --- | --- | --- | --- |
| Regimen B (ER10) | $C_{max}$ | 1.024 | 0.917-1.143 |
| vs. | $AUC_t$ | 0.990 | 0.933-1.049 |
| Regimen A (ER8) | $AUC_{inf}$ | 0.976 | 0.918-1.037 |
| Regimen D (ER11) | $C_{max}$ | 1.063 | 0.952-1.187 |
| vs. | $AUC_t$ | 0.985 | 0.929-1.044 |
| Regimen A (ER8) | $AUC_{inf}$ | 0.977 | 0.919-1.038 |
| Regimen F (ER12) | $C_{max}$ | 1.034 | 0.926-1.154 |
| vs. | $AUC_t$ | 0.958 | 0.904-1.016 |
| Regimen A (ER8) | $AUC_{inf}$ | 0.958 | 0.901-1.018 |

As can be seen from this data, all three of the 30 mg tablets prepared using wet granulation (ER10, ER11, and ER12) were bioequivalent under fasting conditions to the tablet prepared via direct compression (no wet granulation). Effect of a High-Fat Meal on Example 37 Formulation (ER10)

The effect of a high-fat meal on the pharmacokinetic parameters of the Example 14 (ER10, 30 mg active, 30% tartaric acid) formulation is summarized in Table 15D.

TABLE 15D

Mean (% CV)[c] Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
| --- | --- | --- | --- |
| $C_{max}$ | ng/mL | 55.8 (27) | 76.3 (30) |
| $T_{max}$[a] | hours | 3.0 (1.0-4.0) | 4.0 (1.5-8.0) |
| $AUC_t$ | ng · h/mL | 473 (24) | 605 (23) |
| $AUC_{inf}$ | ng · h/mL | 484 (24) | 609 (23) |
| $t_{1/2}$[b] | hours | 10.1 (50) | 9.1 (35) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 14 formulation (ER10) administered after a high-fat meal relative to administration under fasting conditions was also determined based on analysis of the natural logarithms of $C_{max}$, $AUC_t$, and $AUC_{inf}$. The results are summarized in Table 15E below.

TABLE 15E

Bioavailability of Single Dose of the 30 mg Once-Daily Tablet ER10 Administered after High-Fat Meal Relative to under Fasting Conditions

| | | Relative Bioavailability | |
| | PK Parameter | Point Estimate | 90% Confidence Interval |
| --- | --- | --- | --- |
| Regimen C (ER10, high-fat meal) vs. Regimen B (ER10, fasting | $C_{max}$ | 1.322 | 1.134-1.541 |
| | $AUC_t$ | 1.296 | 1.194-1.405 |
| | $AUC_{inf}$ | 1.278 | 1.174-1.392 |

As can be seen from this data, a high-fat meal increased the Cmax and AUCinf for the ER10 formulation (30 mg active, 30% tartaric acid) by about 32% and 28%, respectively.

Effect of a High-Fat Meal on Example 15 Formulation (ER11)

The effect of a high-fat meal on the pharmacokinetic parameters of the Example 15 (ER11, 30 mg, 20% tartaric acid) formulation is summarized in Table 15F.

TABLE 15F

Mean (% CV)[c] Pharmacokinetic Parameters for Compound 1 Following Administration of Single 30 mg Dose of the Once-Daily Tablet Formulation ER11 under Fasting Conditions and After High-Fat Meal

| PK Parameter | Units | Regimen D (ER11, fasting) (n = 24) | Regimen E (ER11, high fat meal) (n = 12) |
| --- | --- | --- | --- |
| $C_{max}$ | ng/mL | 61.0 (25) | 82.2 (33) |
| $T_{max}$[a] | hours | 2.0 (1.0-4.0) | 4.0 (3.0-8.0) |
| $AUC_t$ | ng · h/mL | 487 (22) | 648 (24) |
| $AUC_{inf}$ | ng · h/mL | 499 (22) | 657 (24) |
| $t_{1/2}$[b] | hours | 9.0 (61) | 9.7 (53) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 15 formulation (ER11) administered after a high-fat meal relative to administration under fasting conditions was also determined based on analysis of the natural logarithms of $C_{max}$, $AUC_t$, and $AUC_{inf}$. The results are summarized in Table 15G below.

TABLE 15G

Bioavailability of Single Dose of the 30 mg Once-Daily Tablet ER11 Administered after High-Fat Meal Relative to under Fasting Conditions

| | | Relative Bioavailability | |
| | PK Parameter | Point Estimate | 90% Confidence Interval |
| --- | --- | --- | --- |
| Regimen E (ER11, high-fat meal) vs. Regimen D (ER11, fasting) | $C_{max}$ | 1.343 | 1.153-1.563 |
| | $AUC_t$ | 1.305 | 1.204-1.415 |
| | $AUC_{inf}$ | 1.285 | 1.181-1.398 |

As can be seen from this data, a high-fat meal increased the Cmax and AUCinf for the ER11 formulation (30 mg active, 20% tartaric acid) by about 34% and 29%, respectively, which was a similar food effect as that observed for the Example 14 (ER10) tablet.

Effect of a High-Fat Meal on Example 16 Formulation (ER12)

The effect of a high-fat meal on the pharmacokinetic parameters of the Example 16 (ER12, 30 mg active, 10% tartaric acid) formulation is summarized in Table 15H.

TABLE 15H

Mean (% CV)[c] Pharmacokinetic Parameters for Compound
1 Following Administration of Single 30 mg Dose
of the Once-Daily Tablet Formulation ER12 under
Fasting Conditions and After High-Fat Meal

| PK Parameter | Units | Regimen E (ER12, fasting) (n = 24) | Regimen G (ER12, high fat meal) (n = 12) |
|---|---|---|---|
| $C_{max}$ | ng/mL | 58.6 (34) | 84.2 (33) |
| $T_{max}$[a] | hours | 2.0 (1.0-4.0) | 4.0 (4.0-6.0) |
| $AUC_t$ | ng · h/mL | 481 (23) | 615 (24) |
| $AUC_{inf}$ | ng · h/mL | 495 (23) | 622 (23) |
| $t_{1/2}$[b] | hours | 9.3 (63) | 11.7 (91) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 16 formulation (ER12) administered after a high-fat meal relative to administration under fasting conditions was also determined based on analysis of the natural logarithms of $C_{max}$, $AUC_t$, and $AUC_{inf}$. The results are summarized in Table 15I below.

TABLE 15I

Bioavailability of Single Dose of the 30 mg Once-
Daily Tablet ER12 Administered after High-Fat
Meal Relative to under Fasting Conditions

| | PK Paramenter | Relative Bioavailability | |
| | | Point Estimate | 90% Confidence Interval |
|---|---|---|---|
| Regimen G (ER12, high-fat meal) vs. Regimen F (ER12, fasting) | $C_{max}$ | 1.527 | 1.314-1.774 |
| | $AUC_t$ | 1.295 | 1.196-1.402 |
| | $AUC_{inf}$ | 1.272 | 1.171-1.381 |

As can be seen from this data, a high-fat meal increased the $C_{max}$ and $AUC_{inf}$ for the ER12 formulation (30 mg active, 10% tartaric acid) by about 53% and 27%, respectively.

Example 30: Predicted Pharmacokinetic Parameters
for 15 mg Extended-Release Tablets The mean pharmacokinetic parameters under fasting conditions for the once daily (QD) 15 mg extended-release tablets prepared in Examples 17 (ER13), 18 (ER14), and 19 (ER15) using wet granulation were extrapolated from the single dose data obtained in Example 29 for the Examples 14 (ER10), 15 (ER11), and 16 (ER12) formulations, respectively, under fasting conditions. The results are set forth in Table 16A.

TABLE 16A

Predicted Mean Pharmacokinetic Parameters under Fasting
Conditions for Compound 1 Following Administration of
Single 15 mg Once-Daily Formulations (Extrapolated from
Single-Dose Profiles in Example 52 for 30 mg Doses)

| PK Parameters | Units | Single 15 mg Dose (ER 13) | Single 15 mg dose (ER14) | Single 15 mg dose (ER15) |
|---|---|---|---|---|
| $C_{max}$ | ng/mL | 27.9 | 30.5 | 29.3 |
| $T_{max}$[a] | h | 3.0 | 2.0 | 2.0 |
| $AUC_{inf}$ | ng · h/mL | 242 | 250 | 248 |

[a]Median (minimum-maximum)

Example 31: Preliminary Data from Phase 1 Study
in Healthy Volunteers and Patients with
Rheumatoid Arthritis Compound 1 has been studied in 2 Phase 1 studies, first in human single ascending dose study (Study MI3-401, described in WO 2015/061665, and referred to herein as Study 1), and then in a multiple ascending dose study (Study MI3-845, also generally referred to in WO 2015/061665, and referred to herein as Study 2).

In Study 1, a total of 42 healthy volunteers received a single dose of Compound 1. In Study 2, a total of 32 healthy volunteers received multiple doses of Compound 1 for 14 days (Study 2, Part 1). In addition, 14 patients with RA were enrolled and completed the double-blind Part 2 of Study 2. The study was designed as a multiple dose, randomized, multicenter trial, with the primary objective as assessing the safety, tolerability, and PK of multiple ascending doses of Compound 1 in healthy adult volunteers and to assess the safety, tolerability, and PK of multiple doses of Compound 1 in patients with RA who are on a stable methotrexate regimen.

Details of Study 1 and Study 2 and results obtained therefrom are provided below.

Study 1—Single-Dose Escalation in Healthy Subjects

Study 1 was a single-dose escalation evaluation of Compound 1. Study 1 was designed as a single-site, randomized, double-blind, placebo-controlled study. Fifty-six subjects in general good health were randomized to receive single doses of Compound 1 immediate release capsules comprising Tartrate Hydrate (1, 3, 6, 12, 24, 36, and 48 mg) or placebo in a 3:1 ratio with 8 subjects in each dose level. Study drug was administered following at least 10 hours of fasting. The study was conducted at PPD Development (Austin, TX). Subjects were confined to the study site and supervised for approximately 8 consecutive days. Study protocol and informed consent were approved by RCRC institutional review board (IRB) (Austin, TX).

Study 2—Multiple-Dose Escalation

In Study 2, multiple twice-daily (BID) doses of immediate release capsules comprising Tartrate Hydrate were administered to healthy subjects (Part 1) or to subjects with rheumatoid arthritis (RA) receiving stable doses of methotrexate (Part 2). Both evaluations followed randomized, double-blind, placebo-controlled designs. Part 1 was conducted at PPD Development (Austin, TX) and Part 2 was conducted at two sites: Aspen Clinical Research (Orem, UT) and Altoona Center for Clinical Research (Duncansville, PA). Study protocol and informed consents were approved by RCRC IRB (Austin, TX) and Quorum Review IRB (Seattle, WA).

Study 2—Part 1-Multiple-Dose Escalation in Healthy Subjects

The objective of Part 1 of the multiple-dose study was to characterize the pharmacokinetics, safety, and tolerability of multiple oral doses of Compound 1 immediate release capsules comprising Tartrate Hydrate in healthy subjects. Four escalating dosing regimens (3, 6, 12, and 24 mg Compound 1 or matching placebo twice daily for 13 consecutive days and once in the morning on Day 14) were evaluated. Study drug was administered approximately 30 minutes after a standard breakfast (in the morning) or a snack (in the evening). Forty-four healthy subjects participated in this part of the study with 11 subjects per dose group (8:3 Compound 1: placebo ratio). Subjects were confined to the study site and supervised for approximately 18 days.

Study 2—Part 2-Multiple-Dose Evaluation in Subjects with RA

The objective of Part 2 of the multiple dose study was to assess the pharmacokinetics, safety, and tolerability of multiple oral doses of Compound 1 immediate release capsules comprising Tartrate Hydrate in subjects with mild to moderate RA who were on stable methotrexate treatment. This evaluation was designed to enroll approximately 32 subjects randomized in a 1:1:1:1 ratio to one of four parallel twice-daily regimens (6, 12, and 24 mg Compound 1 and placebo). Subjects received study drug for 26 consecutive days (Study Days 3 through 28) and a single morning dose of study drug on Study Day 29. Compound 1 was administered following breakfast for the morning dose and dinner or snack for the evening dose. Subjects were on methotrexate therapy for at least 3 months and on a stable dose of 10 to 25 mg/week of methotrexate for at least 4 weeks prior to the first dose of study drug administered on Study Day 3 and continued their weekly stable dose of methotrexate on Study Days 1, 8, 15, 22 and 29. Subjects were confined to the study site for a total of 10 days—from Day 1 to Day 4 and from Day 27 to Day 31.

Study Participants

Subjects underwent screening procedures within 30 days prior to the initial administration of study drug. Subjects signed a written informed consent prior to the initiation of any screening or study-specific procedures. Subjects were eligible for study participation if they were men or women between 18 and 55 years of age (Study 1 and Study 2—Part 1) or 18 to 75 years of age (Study 2—Part 2); judged to be in good general health based upon the results of medical history, laboratory profile, physical examination, chest x-ray, and 12-lead electrocardiogram (ECG); and their body mass index (BMI) was within 19 to 29 $kg/m^2$ (Study 1 and Study 2—Part 1) or within 19 to 39 $kg/m^2$ (Study 2—Part 2) at screening. Subjects were considered eligible to participate in Study 2—Part 2 if they had diagnosis of RA based on the 2010 American College of Rheumatology/European League against Rheumatism criteria ≥6 months, have been on methotrexate therapy ≥3 months (and folate or equivalent for at least 2 weeks prior to Study Day 1), on a stable methotrexate dose of 10 to 25 mg/week for at least 4 weeks prior to the first dose of study drug administered on Study Day 3.

In both studies, subjects were excluded if they had any clinically significant abnormalities, infection, major febrile illness, hospitalization, or had any clinically relevant surgical procedure within 30 days prior to the first dose of study drug; had positive test result for hepatitis A virus immunoglobulin M, hepatitis B surface antigen, or hepatitis C virus antibody, or HIV antibodies at Screening; had history or evidence of active or latent tuberculosis; had history of diabetes or lymphoproliferative disease or evidence of immunosuppression (except for use of methotrexate in Study 2—Part 2); or had clinically significant findings at Screening as determined by the principal investigator. Additionally, subjects in Study 2—Part 2 were excluded if they had a history of acute inflammatory joint disease of different origin other than RA or had current or expected need for oral intake of >10 mg prednisone/day or equivalent corticosteroid therapy.

Pharmacokinetic Sampling

In healthy subjects, serial blood samples were collected over 72 hours after single dosing (Study 1) or over 12 hours after the first dose (Study Day 1) and over 72 hours after the last dose (Study Day 14) of study drug (Study 2—Part 1). In subjects with RA, serial blood samples were collected over 48 hours on Study Day 1 for methotrexate assay, over 12 hours following the first Study drug dose on Study Day 3 for Compound 1 assay, over 12 hours following the morning Study drug dose on Study Day 28 for Compound 1 assay, and over 48 hours following the last Study drug dose on Study Day 29 for Compound 1 and methotrexate assays. Pre-dose trough samples were collected prior to the morning dose on Study Days 5, 6, 7, 13, and 14 in Study 2—Part 1 to assess attainment of steady state.

Urine for Compound 1 assay was collected over a 12-hour interval after the last dose was administered on Study Day 14 in Study 2—Part 1 and on Study Days 28 and 29 in Study 2—Part 2. Urine for methotrexate assay was collected for 48 hours on Study Day 1 and Study Day 29.

Plasma and urine concentrations of Compound 1 and methotrexate were determined using validated liquid chromatography method with mass spectrometric detection methods. The lower limits of quantitation (LLOQ) for Compound 1 and methotrexate in plasma were established at 0.0503 ng/mL and 1.00 ng/mL, respectively. The LLOQ for Compound 1 and methotrexate in urine were established at 1.01 ng/ml and 0.0500 µg/mL, respectively. Samples quantified below the LLOQ were reported as zero. For Compound 1 assays, inter-run variability (measured as % coefficient of variation [% CV]) was ≤ 9.5% for plasma ≤8.4% for urine and the mean absolute bias was ≤6.7% for plasma and ≤5.9% for urine. For methotrexate assay, inter-run variability (% CV) was ≤3.9% for plasma and ≤5.2% for urine and the mean absolute bias was ≤5.4% in plasma and ≤13.1% in urine.

Pharmacokinetic Analyses

Compound 1 and methotrexate pharmacokinetic parameters were determined using non-compartmental analyses with Phoenix software (Version 6.3, Certara, Princeton, NJ, USA). Calculated pharmacokinetic parameters included the maximum observed plasma concentration ($C_{max}$), time to $C_{max}$ ($T_{max}$), trough plasma concentration ($C_{trough}$), the apparent terminal phase elimination rate constant (B), the terminal phase elimination half-life ($t_{1/2}$), the area under the plasma concentration-time curve (AUC) [from time 0 to time of the last measurable concentration ($AUC_t$), from time 0 to infinity ($AUC_\infty$) for single dosing, and over a 12-hour dosing interval ($AUC_{0-12}$, or $AUC_{12,ss}$) for multiple dosing and the apparent oral clearance (CL/F). Compound 1 functional half-life ($t_{1/2}F$) following multiple dosing was calculated as $\ln(2)/(\ln[C_{max}/C_{trough}]/\tau)$ at steady state, where t is the 12-hour dosing interval (Dutta et al., *Clin. Drug Investig.*, 2006, Vol. 26 (12), pp. 681-690). The accumulation ratio ($R_{ac}$) was calculated as the ratio of Compound 1 $AUC_{0-12}$ on Day 14 to Day 1 (Study 2—Part 1) or Day 28 to Day 3 (Study 2—Part 2). The percentage of Compound 1 dose recovered unchanged in urine ($f_e$ %) at steady state was calculated as the amount of Compound 1 recovered in urine over the 0 to 12-hour interval (Au, 0-12), divided by the administered dose and multiplied by 100. Renal clearance (CLr) was calculated as Au, $_{0-12}/AUC_{0-12}$ at steady state. Methotrexate $f_e$ % was calculated as the amount of methotrexate recovered in urine over the 0 to 48-hour interval (Au, 0-48), divided by the administered dose and multiplied by 100. CLr of methotrexate was calculated as Au, $_{0-48}/AUC_{0-48}$. The effect of co-administration of methotrexate on Compound 1 exposure was assessed from the ratios of Compound 1 $AUC_{0-12}$ and $C_{max}$ on Study Day 29 to Study Day 28. The effect of Compound 1 on methotrexate exposure was assessed from the ratios of methotrexate $AUC_\infty$ and $C_{max}$ on Study Day 29 to Study Day 1.

Safety and Tolerability Assessment

Safety was evaluated based on assessments of adverse events, vital signs, physical examination, laboratory metrics, and 12-lead electrocardiogram (ECG). All subjects who received at least one dose of study drug were included in the 2) was discontinued early due to slow recruitment rate and 14 subjects with RA were actually enrolled and completed this evaluation. No early withdrawals occurred in any of the three evaluations. A summary of demographic data is presented in Table 17A.

TABLE 17A

| Baseline Demographics of Study Participants | | | | | |
|---|---|---|---|---|---|
| | Study 1 | | Study 2-Part 1 | | Study 2-Part 2 | |
| | Compound 1 N = 42 | Placebo N = 14 | Compound 1 N = 32 | Placebo N = 12 | Compound 1 N = 11 | Placebo N = 3 |
| Mean Age, years ± SD | 31.0 ± 9.8 | 32.4 ± 8.6 | 33.3 ± 9.9 | 30.7 ± 5.0 | 59.3 ± 8.3 | 58.7 ± 14.3 |
| Mean Weight, kg ± SD | 74.7 ± 10.1 | 74.3 ± 8.8 | 74.1 ± 9.9 | 78.4 ± 13.6 | 78.5 ± 14.9 | 62.5 ± 6.9 |
| Mean Height, cm ± SD | 171 ± 8.9 | 171 ± 10.2 | 172 ± 7.9 | 177 ± 6.2 | 171 ± 7.3 | 165 ± 9.9 |
| Sex, number (%) | 35 males (83.3%), 7 females (16.7%) | 11 males (79%), 3 females (21%) | 29 males (91%), 3 females (9%) | 12 males (100%) | 6 males (54.5%), 5 females (45.5%) | 3 females (100%) |
| Race, number (%) | 30 White (71%), 10 Black (24%), 1 Asian (2%), 1 Other (2%) | 11 White (79%), 3 Black (21%) | 23 White (72%), 9 Black (28%) | 9 White (75%), 2 Black (17%), 1 Asian (8%) | 10 White (91%), 1 Black (9%) | 2 White (67%), 1 Asian (33%) | safety analyses. Subjects who were administered placebo were pooled into a single group within each study or study part. Laboratory test values and vital signs measurements that were above or below the reference range were identified. Subjects were followed-up for a total of 7 days in Study 1, 35 days in Study 2—Part 1, and 57 days in Study 2—Part 2. In healthy subjects, clinical adverse events were graded as described in the Guidance for Industry Toxicity Grading Scale for Healthy Adult and Adolescent Volunteers Enrolled in Preventive Vaccine Clinical Trials (September 2007). In subjects with RA, the severity of adverse events was rated by the investigator as mild (transient and easily tolerated by the subject), moderate (causes subject discomfort and interrupts the subject's usual activities), or severe (causes considerable interference with the subject's usual activities and may be incapacitating or life-threatening). One subject in Study 2—Part 2 was randomized to the placebo arm but received Compound 1 in error on Study Days 10 to 16. Therefore, this subject was included with the Compound 1 cohort for safety assessments.

Statistical Analyses

Dose proportionality for Compound 1 in healthy subjects was tested using the natural logarithms of dose-normalized Cmax and AUC following single dosing (Study 1) or for steady-state dose-normalized $C_{max}$, $C_{trough}$, and AUC following multiple dosing (Study 2—Part 1) assessments. Attainment of steady-state following multiple doses in healthy volunteers was assessed by testing the logarithmic transformation of Compound 1 morning pre-dose concentrations for Study Days 5, 6, 7, 13, and 14 by repeated measures analysis. Statistical analyses were performed using SAS software (Version 9.3; SAS institute Inc., Cary, NC, USA).

Results

Demographics and Subject Disposition

A total of 56 healthy subjects were enrolled in and completed the single-dose evaluation (Study 1) and 44 healthy subjects were enrolled in and completed the multiple-dose evaluation (Study 2—Part 1). Enrollment in the multiple-dose evaluation in subjects with RA (Study 2—Part Compound 1 Single- and Multiple-Dose Pharmacokinetics in Healthy Volunteers Compound 1 plasma concentrations reached peak levels at approximately 1 to 2 hours after oral dosing of the immediate release capsule formulation. Compound 1 plasma concentrations declined bi-exponentially afterwards with a terminal elimination tin of approximately 6 to 15 hours after single dosing (Table 17B) and of 8 to 16 hours after multiple twice-daily dosing (Table 17C). Compound 1 functional half-life, estimated from $C_{max}$ to $C_{trough}$ ratio at steady-state, was approximately 3 hours. After multiple dosing, there was a small but statistically significant (p<0.05) difference between Compound 1 pre-dose concentrations on Study Day 13 (13% lower) compared with Study Day 5. There was no statistically significant difference in Compound 1 pre-dose concentration on Study Day 13 and Study Day 14, indicating that steady-state was achieved by Study Day 13. At steady-state, the median accumulation ratios for Compound 1 $AUC_{0-12}$ were approximately 1.0 over the evaluated dose range (Table 17C).

In the single dose evaluation, 1 mg dose group was excluded from the statistical analyses for $AUC_{\infty}$ as the majority of samples collected at the terminal phase were below the limit of quantitation for all subjects. There was no statistically significant difference in dose-normalized $C_{max}$ between the highest (48 mg) and the lowest (1 mg) dose of Compound 1, and there was no statistically significant trend for change in the dose-normalized $C_{max}$ values with dose. There was no trend for change in Compound 1 dose-normalized $AUC_{\infty}$ with doses over the 3 to 36 mg dose range (P>0.05); however, the dose-normalized $AUC_{\infty}$ following single 48 mg dose was 40% lower than that following 3 mg dose (p<0.05).

Following multiple dosing in healthy subjects, there was no statistically significant difference (p >0.05) in Compound 1 dose-normalized steady-state Cmax, Ctrough, or AUC for the 24 mg twice-daily regimen compared to the 3, 6, or 12 mg twice-daily regimens.

Overall, Compound 1 exposures appeared to be dose proportional particularly over the single dose range of 3 to 36 mg and the multiple dose range of 3 mg to 24 mg BID.

TABLE 17B

| Pharmacokinetic Parameters (Units) | 1 mg Cpd. 1 (N = 6) | 3 mg Cpd. 1 (N = 6) | 6 mg Cpd. 1 (N = 6) | 12 mg Cpd. 1 (N = 6) | 24 mg Cpd. 1 (N = 6) | 36 mg Cpd. 1 (N = 6) | 48 mg Cpd. 1 (N = 6) |
|---|---|---|---|---|---|---|---|
| $C_{max}$ (ng/mL) | 7.72 ± 2.36 | 25.0 ± 6.88 | 38.9 ± 9.96 | 82.9 ± 12.1 | 158 ± 18.4 | 277 ± 44.5 | 314 ± 81.9 |
| $T_{max}$ (h) [a] | 1.3 (1.0-2.0) | 1.0 (1.0-1.5) | 1.0 (1.0-1.5) | 1.3 (0.5-1.5) | 1.3 (1.0-1.5) | 0.8 (0.5-1.0) | 1.0 (0.5-1.0) |
| $t_{1/2}$ (h)[b] | — | 5.9 ± 2.4 | 11.0 ± 3.4 | 12.1 ± 7.4 | 14.5 ± 9.0 | 6.4 ± 4.0 | 12.2 ± 3.5 |
| $AUC_t$ (ng · h/mL) | 29.8 ± 5.78 | 102 ± 27.5 | 159 ± 37.5 | 329 ± 48.9 | 612 ± 78.6 | 909 ± 201 | 1030 ± 174 |
| $AUC_\infty$ (ng · h/mL) | — | 103 ± 27.6 | 160 ± 37.6 | 331 ± 49.8 | 615 ± 78.1 | 911 ± 202 | 1040 ± 174 |
| CL/F (L/h) | — | 31.3 ± 10.4 | 39.1 ± 9.06 | 37.0 ± 6.32 | 39.5 ± 4.92 | 41.1 ± 8.35 | 47.6 ± 8.97 |

Pharmacokinetic parameters (mean ± standard deviation) of Compound 1 after administration of single doses of the immediate release formulation to healthy subjects

[a] Median (range)
[b] Terminal elimination half-life, presented as harmonic mean ± pseudo-standard deviation

TABLE 17C

| PK Parameters (Units) | 3 mg BID (N = 8) | 6 mg BID (N = 8) | 12 mg BID (N = 8) | 24 mg BID (N = 8) |
|---|---|---|---|---|
| $C_{max}$ (ng/mL) | 18.5 ± 5.41 | 28.8 ± 3.67 | 57.6 ± 11.0 | 119 ± 16.9 |
| $T_{max}$ (h) | 1.5 (0.5-3.0) | 2.0 (1.5-3.0) | 2.3 (1.5-3.0) | 1.8 (1.5-2.0) |
| $AUC_{0-12}$ (ng · h/mL) | 78.3 ± 20.3 | 138 ± 16.7 | 271 ± 52.7 | 529 ± 62.6 |
| $C_{trough}$ (ng/mL) | 1.46 ± 0.50 | 2.29 ± 0.41 | 4.54 ± 1.55 | 9.50 ± 2.57 |
| $t_{1/2}$ (h)[a] | 15.7 ± 10.6 | 13.6 ± 8.5 | 7.6 ± 4.8 | 8.0 ± 4.2 |
| $t_{1/2}$F (h)[b] | 3.2 ± 0.4 | 3.3 ± 0.3 | 3.2 ± 0.5 | 3.3 ± 0.4 |
| CL/F (L/h) | 40.7 ± 10.6 | 43.9 ± 5.4 | 45.5 ± 8.04 | 46.1 ± 6.44 |
| $CL_r$ (L/h) | 7.5 ± 2.34 | 8.1 ± 1.8 | 9.7 ± 2.3 | 8.6 ± 2.8 |
| $f_e$ (%) | 19 ± 5 | 19 ± 6 | 21 ± 4 | 19 ± 6 |
| $R_{ac}$ $AUC_{0-12}$[c] | 1.1 (0.9-1.2) | 1.0 (0.9-1.2) | 1.0 (0.9-1.1) | 1.0 (0.8-1.3) |

Steady-State (Day 14) Pharmacokinetic parameters (mean ± standard deviation) of Compound 1 following administration of multiple twice-daily oral doses of the immediate release formulation to healthy subjects

[a] Terminal elimination half-life.
[b] Functional half-life calculated from $C_{max}$ to $C_{trough}$ ratio at steady state.
[c] Accumulation ratio for $AUC_{0-12}$.
Harmonic mean ± pseudo-standard deviation are presented for $t_{1/2}$ and $t_{1/2}$F. Median and range (minimum to maximum) are presented for $T_{max}$ and $R_{ac}$ $AUC_{0-12}$. BID: twice-daily.

Compound 1 Multiple-Dose Pharmacokinetics in Subjects with RA

In subjects with RA who were on stable doses of methotrexate, Compound 1 plasma concentrations reached peak levels at 1 to 2 hours after dosing (Table 17D). The mean terminal elimination half-life of Compound 1 ranged from approximately 10 to 14 hours, and the functional half-life was approximately 4 hours. The median accumulation ratio of Compound 1 after 26 days of twice-daily dosing ranged from 0.8 to 1.4. The median ratio of Compound 1 $C_{max}$ and $AUC_{0-12}$ when administered with methotrexate (on Study Day 29) to those when administered without methotrexate (Study Day 28) ranged from 0.9 to 1.2, indicating a lack of significant effect of methotrexate co-administration on Compound 1 pharmacokinetics. The ratio of Compound 1 exposure in subjects with rheumatoid arthritis to Compound 1 exposure in healthy subjects ranged from 1.1 (24 mg twice-daily dose) to 1.6 (6 mg twice-daily dose) for $AUC_{0-12}$ and from 1.2 (24 mg twice-daily dose) to 1.7 (6 mg twice-daily dose) for $C_{max}$.

TABLE 17D

| PK Parameters (Units) | Compound 1 6 mg BID (N = 4) | | Compound 1 12 mg BID (N = 3) | | Compound 1 24 mg BID (N = 3) | |
|---|---|---|---|---|---|---|
| Study Day | Day 28 | Day 29 | Day 28 | Day 29 | Day 28 | Day 29 |
| $C_{max}$ (ng/mL) | 47.1 ± 7.47 | 42.4 ± 8.85 | 71.1 ± 14.8 | 60.8 ± 4.01 | 129 ± 39.0 | 154 ± 39.5 |
| $T_{max}$ (h) | 1.5 (1.0-2.0) | 2.0 (1.5-3.0) | 2.0 (1.5-2.0) | 2.0 (1.5-3.0) | 1.5 (1.5-4.0) | 1.0 (0.5-1.5) |
| $AUC_{0-12}$ (ng · h/mL) | 231 ± 48.5 | 215 ± 49.2 | 334 ± 49.4 | 338 ± 14.5 | 637 ± 143 | 665 ± 89.8 |
| $C_{trough}$ (ng/mL) | 5.81 ± 3.06 | 4.63 ± 3.48 | 5.41 ± 0.98 | 6.44 ± 1.09 | 15.3 ± 1.86 | 14.9 ± 4.37 |
| $t_{1/2}$ (h)[a] | — | 9.5 ± 3.6 | — | 14.4 ± 5.3 | — | 11.5 ± 7.6 |
| $t_{1/2}$F (h)[b] | — | 3.5 ± 0.9 | — | 3.7 ± 0.2 | — | 3.6 ± 0.1 |

Pharmacokinetic parameters (mean ± standard deviation) of Compound 1 following administration of multiple twice-daily oral doses to subjects with mild to moderate rheumatoid arthritis on stable doses of methotrexate TABLE 17D-continued Pharmacokinetic parameters (mean ± standard deviation) of Compound
1 following administration of multiple twice-daily oral doses to subjects
with mild to moderate rheumatoid arthritis on stable doses of methotrexate

| PK Parameters (Units) | Compound 1 6 mg BID (N = 4) | | Compound 1 12 mg BID (N = 3) | | Compound 1 24 mg BID (N = 3) | |
|---|---|---|---|---|---|---|
| Study Day | Day 28 | Day 29 | Day 28 | Day 29 | Day 28 | Day 29 |
| CL/F (L/h) | 26.7 ± 4.96 | 29.0 ± 5.92 | 36.4 ± 5.44 | 35.6 ± 1.56 | 39.1 ± 9.79 | 36.5 ± 4.70 |
| $CL_r$ (L/h) | 6.94 ± 4.04 | 4.93 ± 2.41 | 6.27 ± 2.79 | 4.96 ± 3.34 | 6.31 ± 0.96 | 8.60 ± 1.30 |
| $f_e$ (%) | 25 ± 14 | 16 ± 5 | 17 ± 8 | 14 ± 10 | 17 ± 5 | 24 ± 2 |
| $R_{ac}$ $AUC_{0-12}$[d] | 1.4 (1.0-1.8) | | 1.2 (0.9-1.4) | | 1.3 (1.2-1.4) | |
| Day 29/Day 28 $AUC_{0-12}$ Ratio[e] | | 0.9 (0.9-1.0) | | 1.0 (0.9-1.1) | | 1.0 (0.9-1.2) |

[a]Terminal elimination half-life.
[b]Functional half-life calculated from Cmax to Ctrough ratio at steady state.
[c]Accumulation ratio for $AUC_{0-12}$.
Harmonic mean ± pseudo-standard deviation are presented for $t_{1/2}$ and $t_{1/2}F$.
Median and range (minimum to maximum) are presented for $T_{max}$, accumulation ratios, and Day 29/Day 28 ratios.
BID: twice-daily

Effect of Compound 1 Co-Administration on Methotrexate Exposure

Pharmacokinetic parameters of methotrexate when administered before (Study Day 1) and after administration of multiple doses of Compound 1 (Day 29) are summarized in Table 17E. Since methotrexate was administered weekly and has a short plasma half-life, no plasma accumulation was expected with repeated dosing and $AUC_\infty$ was calculated for both Days 1 and 29. The median ratio for methotrexate $AUC_\infty$ and $C_{max}$ when administered after multiple doses of Compound 1 (on Study Day 29) to that when administered without Compound 1 (on Study Day 1) ranged from 0.9 to 1.1 and from 0.8 to 1.2, respectively. There was no observed change in methotrexate dose-normalized $AUC_\infty$ when administered with or without Compound 1.

TABLE 17E

Pharmacokinetic parameters (mean ± standard deviation) of methotrexate following
administration to subjects with RA alone (Day 1) or concomitant with Compound 1 (Day 29)

| | Compound 1 6 mg BID Group (N = 4) | | Compound 1 12 mg BID Group (N = 3) | | Compound 1 24 mg BID Group (N = 3) | | Placebo (N = 4) | |
|---|---|---|---|---|---|---|---|---|
| Methotrexate Dose (mg) | 16.3 ± 6.6 | | 14.2 ± 5.2 | | 14.2 ± 1.4 | | 17.5 ± 5.0 | |
| PK Parameters (Units) | Day 1 | Day 29 | Day 1 | Day 29 | Day 1 | Day 29 | Day 1 | Day 29 |
| $C_{max}$ (ng/mL) | 245 ± 63.6 | 228 ± 23.0 | 278 ± 44.0 | 255 ± 99.9 | 196 ± 58.6 | 256 ± 29.3 | 318 ± 138 | 354 ± 182 |
| $T_{max}$ (h) | 2.5 (1.5-6.0) | 1.8 (1.0-2.0) | 3.0 (2.0-3.0) | 2.5 (2.5-3.0) | 3.0 (0-3.0) | 2.5 (2.0-3.0) | 1.8 (1.5-3.0) | 1.8 (1.0-4.0) |
| $AUC_\infty$ (ng · h/mL) | 1470 ± 494 | 1490 ± 424 | 1670 ± 393 | 1780 ± 791 | 966 ± 365 | 1370 ± 324 | 1640 ± 470 | 1590 ± 458 |
| $t_{1/2}$ (h)[a] | 4.0 ± 2.6 | 4.7 ± 1.3 | 4.0 ± 0.3 | 4.2 ± 0.6 | 3.0 ± 1.1 | 3.1 ± 1.3 | 3.9 ± 0.5 | 3.8 ± 0.3 |
| CL/F (L/h) | 11.8 ± 6.43 | 10.9 ± 3.43 | 8.36 ± 1.28 | 8.14 ± 1.03 | 16.9 ± 8.89 | 10.6 ± 1.61 | 11.2 ± 3.81 | 11.3 ± 2.66 |
| $CL_r$ (L/h) | 6.63 ± 3.79 | 5.43 ± 2.02 | 6.13 ± 1.93 | 4.78 ± 2.28 | 7.46 ± 0.70 | 6.43 ± 0.75 | 4.32 ± 1.12 | 5.80 ± 1.08 |
| $f_e$ (%) | 58 ± 29 | 51 ± 20 | 74 ± 19 | 59 ± 26 | 54 ± 25 | 63 ± 4 | 45 ± 25 | 57 ± 26 |
| $AUC_\infty$ Ratio[b] | — | 1.0 (0.8-1.4) | — | 0.9 (0.9-1.3) | — | 1.1 (1.0-3.1) | — | 0.9 (0.8-1.2) |

[a]Terminal elimination half-life presented as harmonic mean ± pseudo-standard deviation.

[b]Ratio of methotrexate exposure ($AUC_\infty$) on Study Day 29 to that on Study Day 1; median and range (minimum to maximum) are presented.

Safety and Tolerability

Across all three evaluations, a total of 74 healthy subjects and 11 subjects with RA received Compound 1 and a total of 26 healthy subjects and 3 subjects with RA received placebo. There were no dose-limiting toxicities or safety concerns with Compound 1 from the single doses up to 48 mg or multiple doses up to 24 mg twice daily. Notably, the safety and tolerability profile of Compound 1 was comparable between subjects who received Compound 1 or placebo, and between healthy subjects and subjects with RA on background treatment of methotrexate, though the number of subjects with RA was limited. There was no evidence of a dose or time dependency for the incidence of adverse events in either healthy subjects or subjects with RA. There were no study discontinuations due to adverse events, no serious adverse events and no clinically significant changes in ECG parameters, or laboratory metrics in any of the subjects or treatment groups. The maximum tolerated dose of Compound 1 was not reached in the single or multiple dose studies. Adverse events that were reported by at least two subjects in Compound 1 or placebo groups in Study 1 or Study 2—Part 1 are presented in Table 17F.

In healthy subjects who were administered single doses of either Compound 1 (1, 3, 6, 12, 24, 36, and 48 mg) or placebo in Study 1, 14.3% (6/42) and 21.4% (3/14) of subjects, respectively, reported to have one or more treatment-emergent adverse events (TEAEs). All TEAEs were assessed as mild in severity. The adverse events reported by more than one subject who received Compound 1 were headache and presyncope (1 subject in 6 mg and 1 subject in 24 mg dose group) in association with venipuncture (see Table 17F).

In healthy subjects who were administered multiple doses of Compound 1 (3, 6, 12, and 24 mg BID) or placebo for 14 consecutive days in Study 2—Part 1, 34% (11/32) and 58% (7/12) of subjects, respectively, reported one or more TEAEs. The overall incidences of TEAEs were numerically higher at higher doses of Compound 1; 2 (25.0%), 2 (25.0%), 3 (37.5%) and 4 (50%) subjects in the 3 mg, 6 mg, 12 mg and 24 mg dose groups, respectively; however, these rates were lower than that was observed in the placebo group (58%). All TEAEs were reported as mild in severity. Four events occurred in at least two subjects who received Compound 1: headache, abdominal pain, diarrhea, and naso-

TABLE 17F

Treatment-emergent adverse events reported by two or more healthy subjects administered Compound 1 or placebo in the single and multiple ascending dose evaluations

| System Organ Class MedDRA Preferred Term | Single doses (Study 1) | | | | | | | | |
|---|---|---|---|---|---|---|---|---|---|
| | Placebo (N = 14) | 1 mg Cmpd. 1 (N = 6) | 3 mg Cmpd. 1 (N = 6) | 6 mg Cmpd. 1 (N = 6) | 12 mg Cmpd. 1 (N = 6) | 24 mg Cmpd. 1 (N = 6) | 36 mg Cmpd. 1 (N = 6) | 48 mg Cmpd. 1 (N = 6) | Total Cmpd. 1 (N = 42) |
| Any Adverse Event | 3 (21.4%) | 0 | 0 | 1 (16.7%) | 0 | 1 (16.7%) | 2 (33.3%) | 2 (33.3%) | 6 (14.3%) |
| Nervous System Disorders | | | | | | | | 0 | |
| Headache | 0 | 0 | 0 | 0 | 0 | 0 | 0 | 2 (33.3%) | 2 (4.8%) |
| Presyncope* | 0 | 0 | 0 | 1 (16.7%) | 0 | 1 (16.7%) | 0 | 0 | 2 (4.8%) |

| System Organ Class MedDRA Preferred Term | Multiple twice-daily doses (Study 2-Part 1) | | | | | |
|---|---|---|---|---|---|---|
| | Placebo (N = 12) | 3 mg Cmpd. 1 (N = 8) | 6 mg Cmpd. 1 (N = 8) | 12 mg Cmpd. 1 (N = 8) | 24 mg Cmpd. 1 (N = 8) | Total Compound 1 (n = 32) |
| Any Adverse Event Gastrointestinal Disorders | 7 (58.3%) | 2 (25.0 %) | 2 (25.0%) | 3 (37.5%) | 4 (50.0%) | 11 (34.4%) |
| Abdominal Discomfort | 3 (25.0%) | 0 | 0 | 0 | 0 | 0 |
| Abdominal Pain | 0 | 0 | 1 (12.5%) | 0 | 1 (12.5%) | 2 (6.3%) |
| Diarrhoea | 1 (8.3%) | 0 | 1 (12.5%) | 1 (12.5%) | 0 | 2 (6.3%) |
| Infections and Infestations | | | | | | |
| Nasopharyngitis | 2 (16.7%) | 1 (12.5%) | 1 (12.5%) | 0 | 0 | 2 (6.3%) |
| Nervous System Disorders | | | | | | |
| Headache | 2 (16.7%) | 0 | 2 (25.0%) | 2 (25.0%) | 1 (12.5%) | 5 (15.6%) |

*The two cases of presyncope were associated with venipuncture.

pharyngitis; three of these events also occurred in subjects who received placebo: headache, diarrhea and nasopharyngitis (Table 17F).

There were no clinically significant changes in any hematologic parameters after multiple-dose administration in healthy subjects for 14 days. With increasing doses of Compound 1, there were statistically significant downward trends in mean levels of hemoglobin, RBCs, WBCs and neutrophils; however, even at the 24 mg dose, the mean levels were within the normal reference range. The mean changes in reticulocyte counts with increasing dose of Compound 1 compared to placebo were not statistically significant, suggesting no evidence of a dose related effect on reticulocyte counts after 14 days of Compound 1 treatment. Total cholesterol, HDL-cholesterol, and LDL-cholesterol showed a statistically significant upward trend with increasing Compound 1 dose compared with placebo; however, the final mean values for these lipid parameters in the Compound 1 dose groups remained within the normal reference range.

Subjects with mild to moderate RA on stable background doses of methotrexate, in Study 2—Part 2, were administered multiple doses of Compound 1 (a total of 11 subjects) or placebo (a total of 3 subjects). Five subjects in the Compound 1 dose groups and two subjects in the placebo group experienced at least one TEAE. In the Compound 1 dose groups, 7 TEAEs were reported: nausea, vomiting, viral gastroenteritis, upper respiratory tract infection, post-traumatic neck syndrome, back pain, and insomnia. All TEAEs were reported by the investigators as mild or moderate in severity, and no adverse event was reported in more than one subject in any treatment group. There was no evidence of a dose relationship with any of these events. Notably, as these subjects with RA received a stable background dose of methotrexate, there were no changes in hepatobiliary metrics for those receiving Compound 1. There was also no evidence of a Compound 1 dose-related effect on renal function in these subjects with RA, as evaluated by serum creatinine and blood urea nitrogen values.

Discussion

Compound 1 was well-tolerated after single doses up to 48 mg and multiple twice daily doses up to 24 mg of Compound 1 immediate-release formulation. All adverse events occurred after single- or multiple-dose administrations were mild to moderate in nature with comparable frequency between subjects who received Compound 1 or placebo. No anemia, serious infections, or clinically significant changes in hematology, hepatobiliary or renal laboratory metrics was observed with 14 days of repeated Compound 1 dosing in healthy volunteers or 27 days of dosing in RA patients.

Compound 1 displayed multi-exponential plasma disposition with a functional half-life of 3 to 4 hours across the dose range of 3 to 24 mg twice daily of the immediate-release formulation in healthy volunteers and subjects with RA. The terminal elimination half-life of Compound 1 ranged from 6 to 16 hours across the different dose levels. However, given the multi-exponential disposition of Compound 1, the longer terminal half-life is less relevant clinically than the functional half-life (Dutta et al., Clin. Drug Investig., 2006, Vol. 26 (12), pp. 681-690; Sahin, Pharm. Res., 2008, Vol. 25 (12), pp. 2869-77). Consistent with a shorter functional half-life, there was no accumulation across the evaluated 3 to 24 mg twice-daily dose range. While there are no solid clinical data to suggest that extended exposure is needed for efficacy of JAK inhibitor (i.e., to determine whether efficacy is concentration driven or AUC driven), the pharmacokinetic profile of the immediate-release formulation of Compound 1 appears to be generally more suited for twice-daily dosing than for once-daily dosing.

Compound 1 displayed dose-proportional pharmacokinetics particularly over the 3 to 36 mg dose range, which encompasses the dose ranges evaluated in Phase 2b clinical trials in RA (3 to 18 mg BID and 24 mg QD), or that is currently being evaluated in Crohn's disease (3 to 24 mg BID).

It has been reported previously that the JAK inhibitors tofacitinib and filgotinib have higher exposures in subjects with RA than those in healthy volunteers (see FDA, "Clinical Pharmacology and Biopharmaceutics Review(s)-Tofacitinib", Application Number 203214Orig1s000, Center for Drug Evaluation and Research, 2011; Namour et al., Clin. Pharmacokinet., 2015, Vol. 54, pp. 859-874). Compound 1's apparent oral clearance was 23% lower in subjects with RA (leading to approximately 30% higher exposure), on average across all dose groups, compared to healthy subjects. In general, older subjects are expected to have lower renal and metabolic capacity compared to younger subjects (Mangoni, Br. J Clin. Pharmacol., 2004, Vol. 57 (1), pp. 6-14). RA subjects who received multiple doses of Compound 1 were 26 years older, on average, than the healthy subjects evaluated in Study 2 (Table 21A); therefore, age cannot be excluded as potential contributor to the apparently 30% higher exposure of Compound 1 in RA subjects than in healthy subjects.

Methotrexate remains the first line therapy for treatment of RA and is often used with biologic DMARDs or in combination with other csDMARDs (see Ma, et al., Rheumatology (Oxford), 2010, Vol. 49 (1), pp. 91-8; Singh, et al., Arthritis Care Res. (Hoboken), 2012, Vol. 64 (5), pp. 625-39; Smolen, et al., Ann. Rheum. Dis., 2014, Vol. 73 (3), pp. 492-509). Therefore, at least in a subset of the RA patients, it is expected that Compound 1 will be added to the first line therapy, methotrexate; thus, it was important to confirm a lack of any potential interaction between Compound 1 and methotrexate. The ratios of Compound 1 AUC and Cmax values when administered with methotrexate to those when administered alone indicate lack of significant effect of methotrexate on Compound 1 (Table 21D). Similarly, Compound 1 did not have any significant effect on methotrexate exposures (Table 21E). This was consistent with the observed safety and tolerability profiles in these two populations.

In summary, Compound 1 displayed favorable safety and tolerability profiles over single doses up to 48 mg and multiple doses up to 24 mg twice daily for 14 days in healthy subjects and for 27 days in subjects with RA. Compound 1 demonstrated a pharmacokinetic profile suitable for twice-daily dosing with the immediate release formulation. There was no pharmacokinetic interaction between methotrexate and Compound 1 and there was no accumulation of Compound 1 with repeated administration.

Example 32: Treatment of Moderately to Severely Active Rheumatoid Arthritis in Patients Who have Inadequately Responded to or are Intolerant to Anti-TNF Therapy The following example briefly describes the results of a Phase 2b, 12-week, randomized, double-blind, parallel-group, placebo-controlled study in which adult subjects with moderately to severely active rheumatoid arthritis (RA) who have inadequately responded to or who are intolerant to an anti-tumor necrosis factor (TNF) therapy were treated with Compound 1.

The study was conducted in accordance with the International Conference on Harmonisation guidelines, applicable regulations, and the principles of the Declaration of Helsinki. The study protocol was approved by an independent ethics committee or institutional review board. All patients provided written informed consent before participating in any study-related procedures.

Participants

Adult men and women aged 18 years or older, who had been diagnosed with RA and fulfilled either the 1987 revised American College of Rheumatology (ACR) classification criteria (Arnett et al, Arthritis Rheum., 1988, Vol. 31 (3), pp. 315-324) or the 2010 ACR/European League Against Rheumatism (EULAR) criteria (Smolen et al, Ann. Rheum. Dis., 2010, Vol. 69 (6), pp. 964-975) were enrolled in the study. Active RA was defined as subjects having ≥6 swollen joints (based on a 66-joint count); ≥6 tender joints (based on a 68-joint count); and high-sensitivity C-reactive protein (hsCRP)>upper limit of normal (ULN=5 mg/L) or seropositivity for both rheumatoid factor (RF) and anti-cyclic citrullinated peptide (CCP). Eligible subjects must have been treated with ≥1 anti-TNF biologic agent for ≥3 months but continued to experience active RA or discontinued anti-TNF biologic therapy because of intolerance or toxicity. In addition, subjects with prior exposure to non-anti-TNF biologic therapy were allowed to enroll, as long as they had failed ≥1 anti-TNF biologic. All biologic therapies had to be washed out prior to randomization: ≥4 weeks for etanercept, ≥8 weeks for adalimumab, infliximab, certolizumab, and golimumab, >8 weeks for abatacept, >12 weeks for tocilizumab, and >1 year for rituximab. A stable dose of methotrexate (7.5-25 mg/week) was required throughout the study. Key exclusion criteria were prior exposure to a JAK inhibitor, or a need for any immunosuppressant other than methotrexate. Subjects with serum aspartate transaminase (AST) or alanine transaminase (ALT)>1.5×ULN or absolute neutrophil count (ANC)<1,200/µL or absolute lymphocytes count <750/µL at screening were excluded.

Study Design and Treatment

The study was a phase 2b, 12-week, randomized, double-blind, parallel-group, placebo-controlled study conducted at 123 sites, enrolling patients in the United States (176 patients, 64%) and Puerto Rico (11 patients, 4%); Australia and New Zealand (6 patients, 2%); Western Europe including Belgium, Spain and Great Britain (29 patients, 11%); Eastern Europe including Czech Republic, Hungary, Poland (54 patients, 20%).

Subjects were equally randomized to receive oral immediate-release doses of Compound 1 (immediate release capsules comprising Tartrate Hydrate) at 3 mg BID, 6 mg BID, 12 mg BID or 18 mg BID, or matching placebo BID, for 12 weeks. Randomization was performed centrally, according to a blocked randomization schedule, by investigators enrolling via an interactive voice response system. Subjects, caregivers, investigators, joint assessors, and the study team were blinded to the treatment administered. Placebo and Compound 1 capsules were identical in appearance. Subjects should have been taking an oral supplement of folic acid (or equivalent) from four weeks prior to baseline and throughout the study. Subjects were allowed to continue stable doses of methotrexate and non-steroidal anti-inflammatory drugs (NSAIDS), acetaminophen, or oral corticosteroids (equivalent to prednisone≤10 mg).

Assessments

The primary efficacy endpoint was the proportion of subjects achieving an ACR20 response at Week 12. Secondary endpoints included the proportions of subjects achieving an ACR50/ACR70 response and the proportion of subjects achieving 28-joint count disease activity score based on C-reactive protein (DAS28 (CRP))≤3.2, or <2.6, at Week 12. Among the other endpoints were the proportion of subjects achieving low disease activity (LDA) or clinical remission (CR) based on Clinical Disease Activity Index (CDAI) criteria (LDA, CDAI≤10; CR, ≤2.8); change in DAS28 (CRP), and change in the Health Assessment Questionnaire-Disability Index (HAQ-DI) (Anderson et al, Arthritis Care Res. (Hoboken), 2012, Vol. 64 (5), pp. 640-647), including the proportion of subjects achieving minimal clinically important difference (MCID) of −0.22 (Strand et al, Rheumatology (Oxford), 2006, Vol. 45 (12), pp. 1505-1513). A post hoc analysis was performed to determine the proportion of subjects who had a sustained ACR20 response, defined as achievement of the ACR20 criteria at every visit (at Weeks 2, 4, 6, 8 and 12).

Safety was evaluated at each scheduled visit during treatment and for 30 days after the last dose of study drug on the basis of AEs, serious AEs, vital signs, and laboratory tests (hematology, blood chemistry, and urinalysis). Adverse events were coded according to the Medical Dictionary for Regulatory Activities (MedDRA, version 17.1). Descriptions of AE severity and post-baseline laboratory changes were based on the Rheumatology Common Toxicity Criteria v.2.0, developed by the OMERACT Drug Safety Working Group (Woodworth et al., 2007, J. Rheumatol., Vol. 34 (6), ppl. 1401-14).

Statistical Methods

All efficacy analyses were conducted in modified intent-to-treat population, which consisted of all randomized patients who received ≥1 dose of study drug. For ACR response rates, the last observation carried forward (LOCF) was the primary missing data imputation method and non-responder imputation (NRI) was also used to assess the robustness of the results. For continuous endpoints including DAS28 (CRP), LOCF missing data imputation was implemented; NRI is reported for binary endpoints. Binary endpoints including ACR response rates were analyzed using chi-square test with normal approximation when comparing each Compound 1 treatment group to placebo group. Continuous endpoints were analyzed using an Analysis of Covariance (ANCOVA) model with treatment group as a factor and baseline measurement as the covariate. The Multiple Comparison Procedure and Modeling (MCPMod) method was implemented to detect any non-flat dose-response relationship by evaluating several non-linear dose-response models at the same time. P-values were not corrected for multiple comparisons.

Assuming ACR20 response rates of 25% in the placebo group and 55% in any Compound 1 group, a sample size of 50 subjects per group (250 patients total) was estimated to provide at least 80% power to detect a 30% difference in response rates between the placebo group and a Compound 1 group when using a 1-sided test with an alpha level of 0.05.

Results

Subject Disposition and Baseline Characteristics

Figures 2A, 2B:
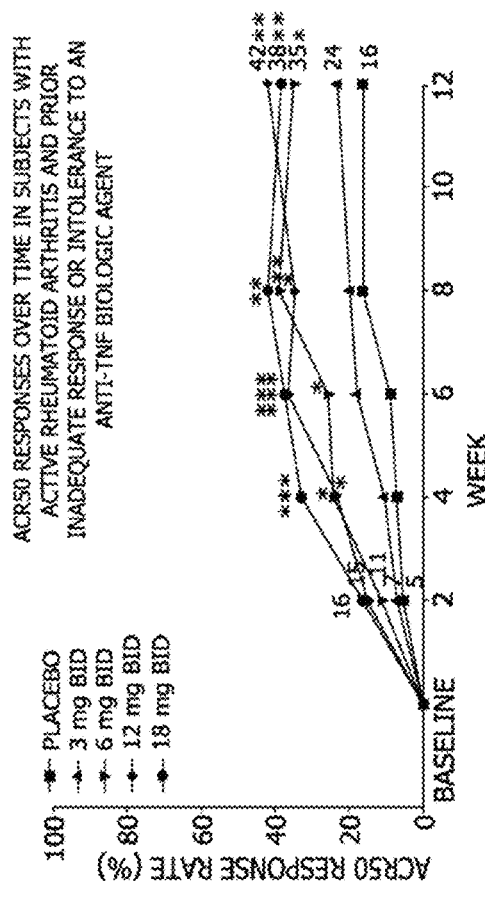
FIGS. 2A-2D show the ACR20 (FIG. 2A), ACR50 (FIG. 2B), and ACR70 (FIG. 2C) responses or DAS28 (CRP) mean change from baseline (FIG. 2D) over time following administration of placebo or various doses of Compound 1 to subjects with active rheumatoid arthritis and prior inadequate response or intolerance to an anti-TNF biologic agent (*P<0.05;  P<0.01; * P<0.001 relative to placebo; modified intent-to-treat population (NRI)).
Figure 2D:
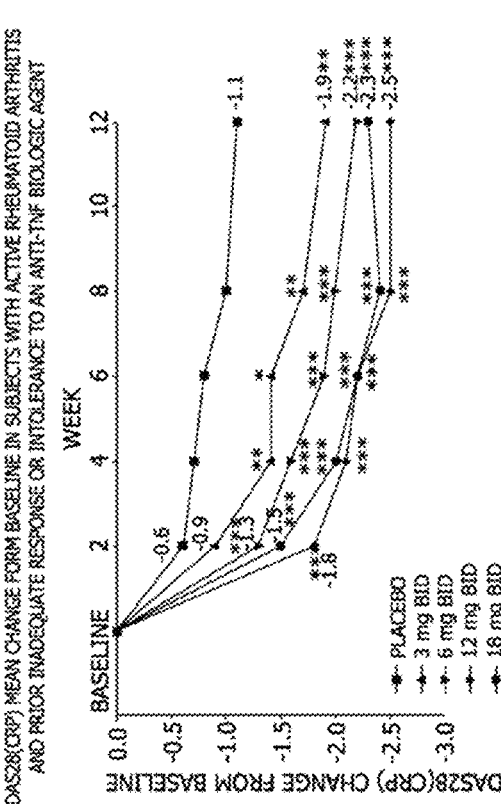
Figure 2C:
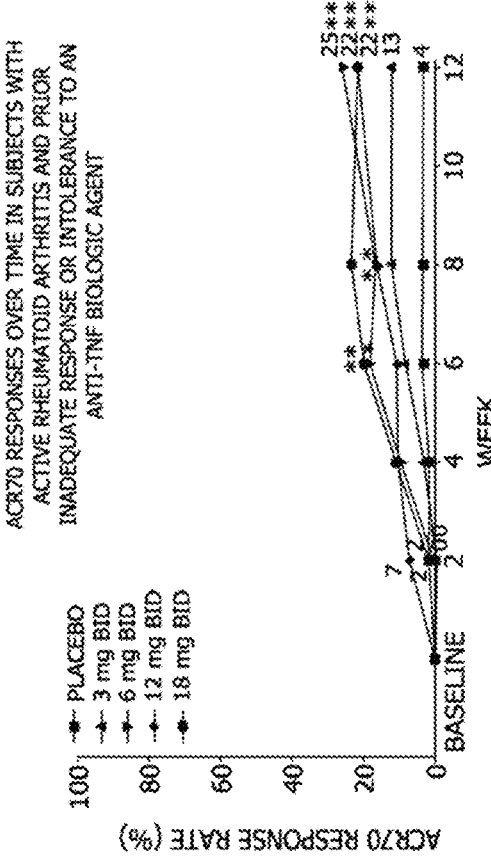
Figure 4:
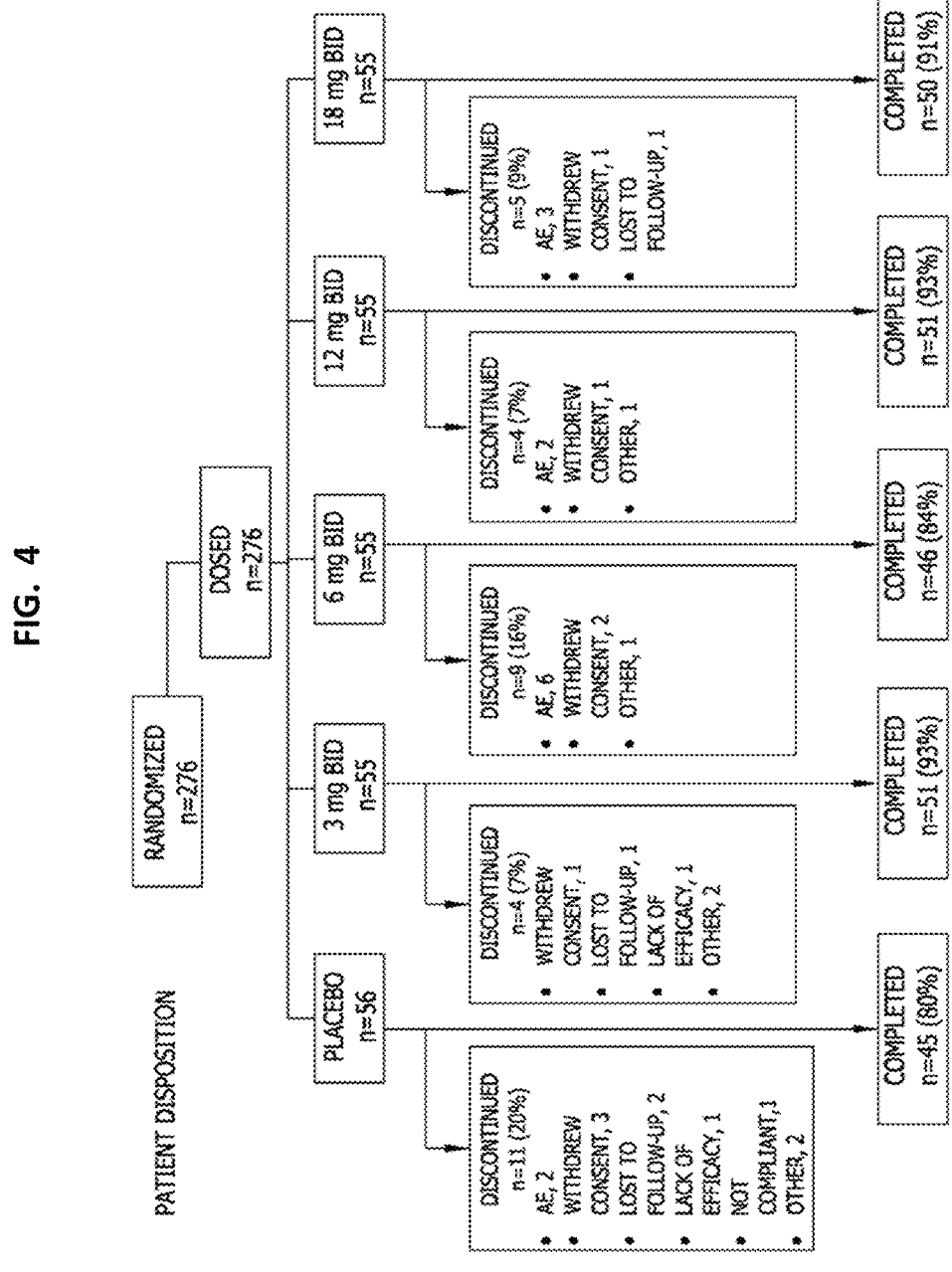
FIG. 4 shows the subject disposition for the study described in Example 32.

In total, 276 subjects were randomized; all received their intended treatment. The overall study completion rate was 88% (FIG. 4). Baseline subject characteristics and disease activity were generally similar among treatment groups (see Table 18A). The mean duration since RA diagnosis was 12 years. Seventy-two percent of subjects had prior exposure to only one anti-TNF, 28% to ≥2 anti-TNFs, and 20% of subjects were also exposed to non-anti-TNF biologics. At baseline, subjects had mean swollen and tender joint counts of 18 (out of 66 joints) and 28 (out of 68 joints), respectively; 60% subjects had an elevated hsCRP and mean DAS28 (CRP) was 5.8.

response rate (42%) was observed with the 18 mg BID dose by week 8 and plateaued thereafter (FIG. 2B). Improvements in ACR70 response rates better than placebo were observed starting at Week 6, with peak response of up to 25% at Week 12 (FIG. 2C). A sustained ACR20 response (at

TABLE 18A

| | | Compound 1 | | | |
|---|---|---|---|---|---|
| Characteristic | Placebo (n = 56) | 3 mg BID (n = 55) | 6 mg BID (n = 55) | 12 mg BID (n = 55) | 18 mg BID (n = 55) |
| Baseline Patient Characteristics and Disease Activity | | | | | |
| Female, number (%) | 48 (86) | 43 (78) | 43 (78) | 44 (80) | 42 (76) |
| Age, years, mean (SD) | 58 (12) | 57 (13) | 56 (12) | 59 (11) | 57 (12) |
| Duration since RA diagnosis, years, mean (SD) | 12.1 (9.0) | 11.8 (9.4) | 12.3 (10.6) | 12.2 (10.2) | 10.9 (7.7) |
| RF positive, number (%) | 49 (88) | 43 (78) | 45 (82) | 45 (82) | 48 (87) |
| Anti-CCP positive, number (%) | 48 (86) | 45 (82) | 45 (82) | 45 (82) | 47 (86) |
| Used ≥1 prior anti-TNF agent, number (%) | 42 (76) | 39 (71) | 38 (70) | 38 (72) | 38 (69) |
| Used ≥2 prior anti-TNF agents, number (%) | 13 (24) | 16 (29) | 16 (30) | 15 (28) | 17 (31) |
| Used prior non-anti-TNF agents, number (%)* | 9 (16) | 10 (18) | 14 (26) | 14 (26) | 7 (13) |
| Disease activity | | | | | |
| TJC68, mean (SD) | 28 (15) | 28 (15) | 30 (16) | 26 (16) | 26 (15) |
| SJC66, mean (SD) | 19 (12) | 17 (10) | 17 (10) | 17 (10) | 18 (10) |
| HAQ-DI, mean (SD) | 1.6 (0.7) | 1.5 (0.7) | 1.6 (0.7) | 1.6 (0.6) | 1.5 (0.6) |
| DAS28(CRP), mean (SD) | 5.8 (0.9) | 5.7 (0.9) | 5.9 (0.9) | 5.7 (0.9) | 5.8 (1.0) |
| CDAI, mean (SD) | 41 (12) | 40 (13) | 42 (12) | 40 (12) | 41 (14) |
| hsCRP, mg/L, mean (SD)[‡] | 10.1 (13.2) | 11.4 (11.8) | 18.6 (27.4) | 14.4 (23.0) | 14.0 (15.1) |
| hsCRP > ULN,[†] n (%)[‡] | 28 (50) | 35 (64) | 34 (62) | 33 (60) | 35 (64) |

Abbreviations: BID—twice daily; CDAI—Clinical Disease Activity Index; DAS28(CRP)—Disease Activity Score-28 joints using C-reactive protein; HAQ-DI—Health Assessment Questionnaire-Disability Index; hsCRP—high-sensitivity C-reactive protein; RA—rheumatoid arthritis; SJC66—swollen joint count using 66 joints; TJC68—tender joint count using 68 joints; TNF—tumor necrosis factor; ULN—upper limit of normal.
*Non-TNF biologic agents.
[†]ULN = 5 mg/L.
[‡]Subjects with normal hsCRP could be enrolled as long as they were positive for rheumatoid factor and anti-cyclic citrullinated peptide.
Modified intent-to-treat population.
Percentages were calculated using non-missing values Efficacy The primary analysis based on LOCF revealed that an ACR20 response was achieved by 55.6% (P=0.033), 63.5% (P=0.004), 72.7% (P<0.001), and 70.9% (P<0.001) in subjects treated with Compound 1 at 3, 6, 12, and 18 mg BID, respectively, compared with 35.2% in subjects who received placebo. Analysis based on NRI also demonstrated a statistically significant improvement in ACR20 response rate in subjects who received any dose of Compound 1 compared with those who received placebo (FIG. 1A). A significant dose-response relationship was observed for all doses of Compound 1 (P<0.01). The ACR20 response rates (NRI) at Week 12 were similar among patients who had received 1 versus ≥2 prior anti-TNFs (FIG. 1B). ACR50 and ACR70 response rates were significantly higher at Compound 1 doses of ≥6 mg BID versus placebo (FIG. 1A).

Significant differences in ACR20 response rates (NRI) were observed at the first post-baseline assessment (Week 2) in subjects treated with Compound 1 12 mg BID and 18 mg BID versus placebo (P≤0.007; FIG. 2A); the maximum response rate (71%) was observed with the 12 mg BID dose by Week 8 and plateaued thereafter. Starting at Week 4, there were significantly greater ACR50 response rates with Compound 1 doses ≥6 mg BID versus placebo; the maximum every visit between Week 2 through 12, NRI) was achieved by 13%, 22%, 40% and 27% of subjects in the Compound 1 3 mg, 6 mg, 12 mg and 18 mg BID groups respectively, versus 4% in the placebo group. Significant improvements in DAS28 (CRP) (LOCF) occurred at the Week 2 assessment with Compound 1 at ≥6 mg BID versus placebo (P<0.001; FIG. 2D).

Figure 2E:
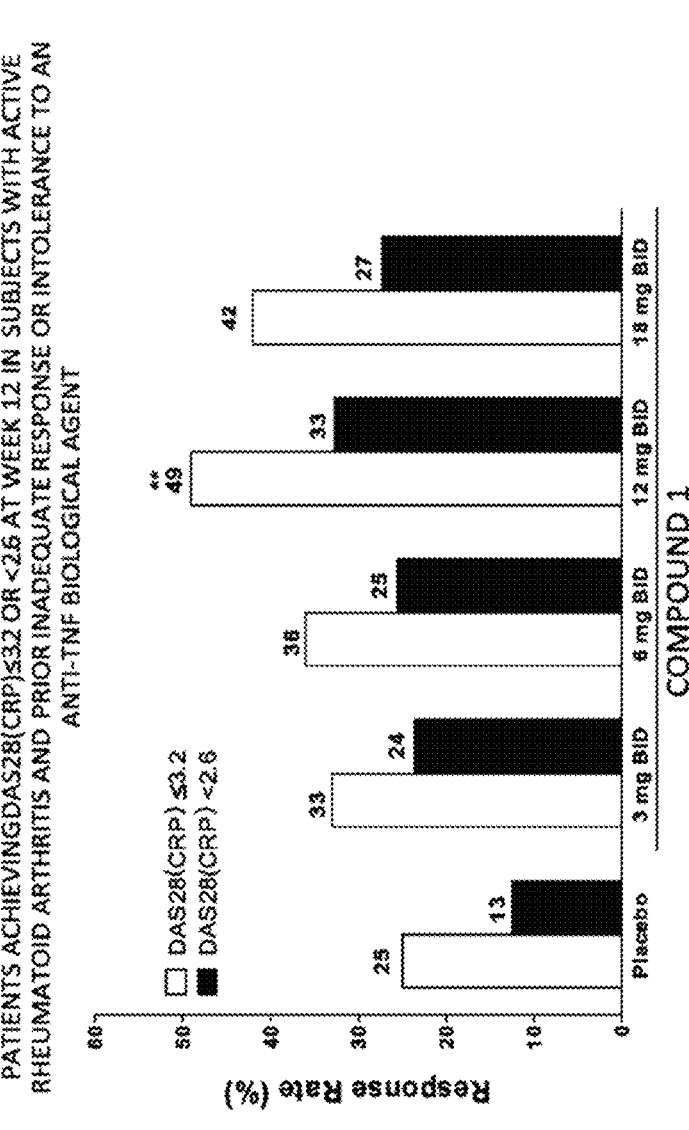
FIG. 2E shows the subjects achieving a DAS28 (CRP) score of ≤3.2 or <2.6 at week 12 in the same population.
Figure 2F:
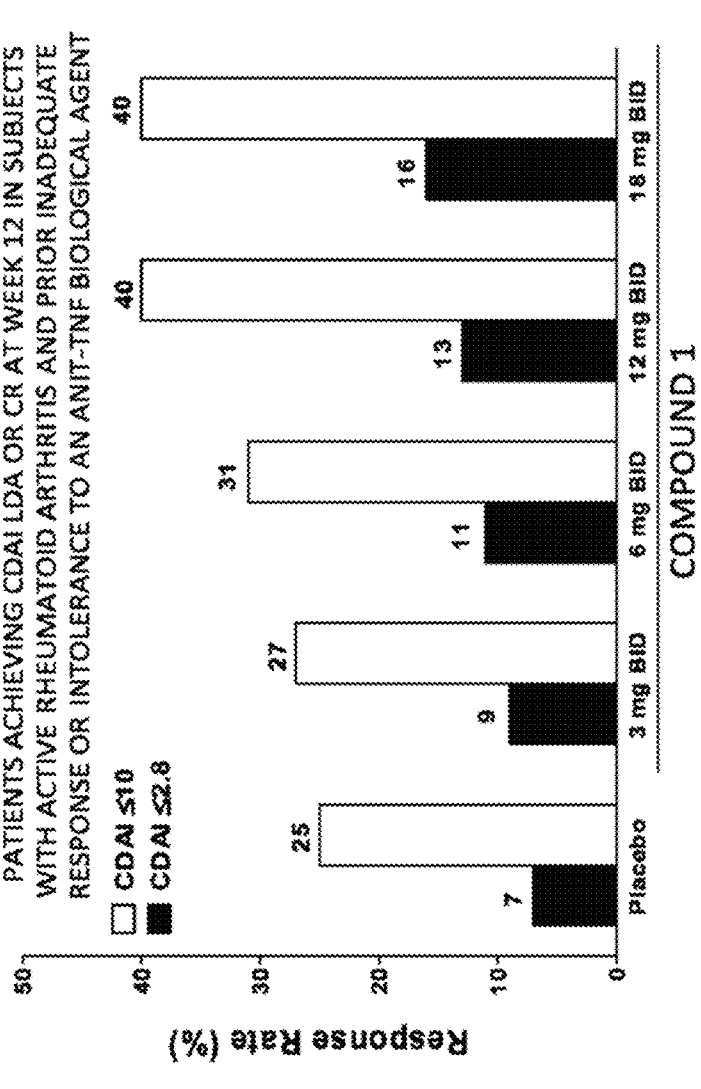
FIG. 2F shows the subjects achieving low disease activity (LDA) or clinical remission (CR) based on clinical disease activity index (CDAI) criteria (LDA is CDAI≤10; CR is CDAI≤2.8) at week 12 in the same population.

A higher percentage of subjects receiving Compound 1 (any dose) achieved DAS28 (CRP)≤3.2 or <2.6, versus placebo at Week 12 (NRI, FIGS. 2E and 2F) with the difference being statistically significantly for the Compound 1 12 mg BID group (DAS28 (CRP)≤3.2, 49%; DAS28 (CRP)<2.6, 33%, P<0.01) compared with placebo (25% and 13%, respectively). Similarly, a higher percentage of patients treated with any dose of Compound 1 achieved CDAI LDA or CR criteria versus placebo at Week 12 (NRI, FIG. 2F). At Week 12, treatment with Compound 1 at 12 mg BID also resulted in statistically significant mean changes from baseline in individual components of the ACR score compared with placebo (Table 18B). In addition, a significantly greater proportion of patients achieved the MCID for HAQ-DI with Compound 1 ≥6 mg BID (58%-64%) as compared with placebo (44%).

TABLE 18B

| | | Mean Changes From Baseline in ACR Components at Week 12 | | | |

| | | Compound 1 | | | |
| ACR Component | Placebo (n = 55) | 3 mg BID (n = 54) | 6 mg BID (n = 53) | 12 mg BID (n = 55) | 18 mg BID (n = 55) |
|---|---|---|---|---|---|
| TJC68 | −9.3 (−12.5, −6.1) | −13.4 (−16.6, −10.1) | −15.7** (−19.0, −12.5) | −16.8** (−20.1, −13.6) | −15.1* (−18.3, −11.9) |
| SJC66 | −6.4 (−8.7, −4.2) | −9.5 (−11.8, −7.2) | −9.2 (−11.4, −6.9) | −10.0* (−12.3, −7.8) | −9.2 (−11.5, −7.0) |
| Patient's assessment of pain | −16.5 (−23.5, −9.5) | −24.7 (−31.8, −17.6) | −31.4**,† (−38.6, −24.2) | −36.3*** (−43.3, −29.3) | −35.0*** (−42.0, −27.9) |
| PhGA | −29.6‡ (−35.3, −23.8) | −33.8 (−39.4, −28.1) | −37.5 (−43.2, −31.7) | −43.5*** (−49.1, −37.9) | −42.4** (−48.0, −36.8) |
| PtGA | −20.0 (−27.0, −13.0) | −24.2 (−31.3, −17.1) | −29.9† (−37.1, −22.6) | −37.4*** (−44.4, −30.4) | −33.5***,† (−40.6, −26.5) |
| HAQ-DI | −0.2 (−0.4, −0.1) | −0.3 (−0.4, −0.1) | −0.5**,† (−0.6, −0.3) | −0.5* (−0.6, −0.3) | −0.5**,† (−0.7, −0.4) |
| HAQ-DI ≤ MCID, n (%), 95% CI | 24 (44), 31-57 | 27 (50), 37-63 | 30 (58), 44-71† | 35 (64), 51-76 | 34 (63), 50-76† |
| hsCRP, mg/L | −0.4 (−4.6, 3.9) | −7.9* (−12.2, −3.6) | −9.7** (−14.1, −5.4) | −6.8* (−11.1, −2.6) | −6.9* (−11.1, −2.6) |

Data are mean (95% CI), unless otherwise noted.
Abbreviations: ACR—American College of Rheumatology; BID—twice daily; HAQ-DI—Health Assessment Questionnaire-Disability Index; hsCRP—high-sensitivity C-reactive protein; LOCF—last observation carried forward; MCID—minimal clinically important difference; PhGA—physician's global assessment of disease activity; PtGA—patient global assessment of disease activity; RA—rheumatoid arthritis; SJC66—swollen joint count using 66 joints; TJC68—tender joint count using 68 joints.
*P < 0.05;
**P < 0.01;
***P < 0.001 relative to placebo.
†1 patient with missing data.
‡2 patients with missing data.
§MCID = −0.22.
Modified intent-to-treat population (LOCF).

Safety

The percentage of subjects with any treatment-emergent AEs was numerically higher in a dose-dependent manner for the Compound 1 6, 12 and 18 mg BID treatment groups compared with placebo (Table 18C). Most reported AEs were considered mild to moderate in severity. The most commonly observed AEs were headache, nausea, upper respiratory tract infection, and urinary tract infection. The incidences of serious AEs and severe AEs were low, without an apparent dose-response relationship (Table 18C). Five subjects in the Compound 1 dose groups reported seven serious AEs (3 mg BID; one subject each with pancreatitis and pulmonary embolism, 6 mg BID; one subject with pulmonary embolism and deep vein thrombosis, one patient with TIA and benign prostate hyperplasia, 18 mg BID dose; one subject acute respiratory failure). One subject on placebo experienced a serious AE of bronchiectasis. The overall infection rates were similar for the Compound 1 3- and 6 mg BID dose groups and placebo (20%, 22%, and 23%, respectively), but were higher in the Compound 1 12- and 18 mg BID dose groups (40% and 38%). No serious infections were reported in any of the Compound 1 treatment groups. Herpes zoster occurred in two subjects in the placebo group (4%) and three subjects who received Compound 1 (1%, one case each in the 3-, 12- and 18 mg BID groups; all were isolated to a single dermatome). The two reported events of hepatic disorders in the 18 mg BID dose group and one event in the placebo group were attributed to increased transaminases; none were serious. There was an adjudicated case of transient ischemic attack (left ventricular hypertrophy, classified as mild) in one subject in the Compound 1 6 mg BID group. One patient in the 6 mg BID group had one event each of basal cell carcinoma and squamous cell carcinoma. There were no opportunistic infections or deaths during the study period.

Dose-dependent increases in low-density lipoprotein cholesterol (LDL-C) and high-density lipoprotein cholesterol (HDL-C) were observed; however, the ratios of LDL-C/HDL-C remained the same through Week 12. Of the subjects with normal AST or ALT at baseline, 6-18% of patients on Compound 1 had elevated AST at least twice, and 4-11% had elevated ALT at least twice, versus 2% and 6% on placebo, respectively. The number of these subjects was higher in the higher dose groups. Most of the elevations were Grade 1 (for AST and ALT, ≥1.2-<1.6×ULN) and Grade 2 (1.6-3.0×ULN). One subject each (2%) in the Compound 1 3 mg BID and placebo group (2%) had a Grade 3 ALT elevation (3.0-8.0× ULN). Of the subjects with normal creatinine at baseline, 4-14% subjects on Compound 1 had elevated creatinine at least twice versus none in the placebo group. One subject in the 18 mg BID group had a Grade 3 elevation (≥1.9-≤3.0×ULN). The elevations did not result in discontinuation of any subject from the study.

Figure 3B:
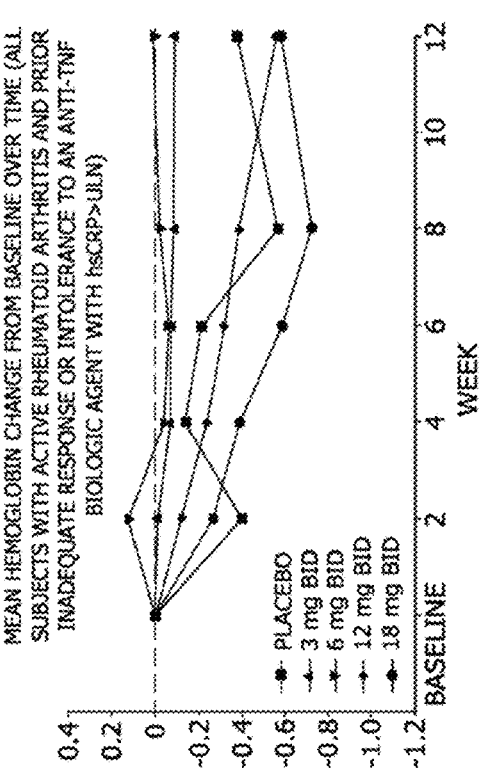
FIG. 3B shows the mean hemoglobin change from base-line over time in subjects with high-sensitivity C-reactive protein (hsCRP) greater than the upper limit of normal (ULN) (normal ranges for hemoglobin: 11.5-15.5 g/dL in females and 13.2-17.0 g/dL in males; ULN for hsCRP=5 mg/L).
Figure 3A:
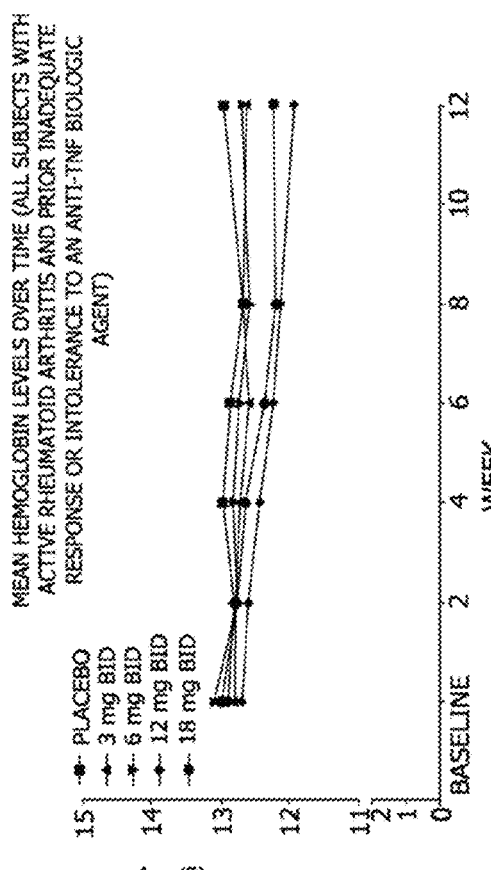
FIG. 3A shows the mean hemoglobin levels over time for all subjects following administration of placebo or various doses of Compound 1 to subjects with active rheumatoid arthritis and prior inadequate response or intolerance to an anti-TNF biologic agent (safety population with observed data (no imputation of missing values)).

Decreases from baseline in mean hemoglobin levels were observed in a dose-dependent manner with Compound 1, although mean hemoglobin levels remained within the normal range across all dose groups during the study (FIG. 3A). Twenty-six out of 219 subjects (11.9%) in the Compound 1 groups had a Grade 2 decrease in hemoglobin (from 15-20 g/L); 14/219 subjects (6.4%) had a Grade 3 decrease (from 21-29 g/L); 8/219 subjects (3.7%) had a Grade 4 decrease (≥30 g/L). The majority (79%) of these decreases were transient (only one occurrence) and one subject discontinued the study due to reported AE of low hemoglobin. However, in subjects with underlying systemic inflammation, as measured by elevated baseline hsCRP, treatment with Compound 1 at 3- or 6 mg BID resulted in mean increases from baseline in hemoglobin levels compared with placebo (FIG. 3B).

Decreases in mean circulating leukocytes, neutrophils (Table 18D) and natural killer (NK) cells were also observed, and one subject discontinued study drug due to leukopenia. Only NK cell reductions appeared to be dose related. The mean percentage change in NK cells was +16.5±46.6 in the placebo group; a dose-dependent decrease was seen in subjects treated with Compound 1 (−15.8±25.3 in the 3 mg BID group, −18.3±47.4 in the 6 mg BID group, −28.0±37.3 in the 12 mg BID group, and −42.6±31.7 in the 18 mg BID group). At all doses of Compound 1, there was a transient mean increase in total lymphocytes, which returned to baseline level by Week 12, except in the 18 mg dose group. There were two subjects in the 18 mg dose group with Grade 4 lymphocyte reduction; one subject was reported to have vaginal and urinary tract infection, and the other herpes zoster. One subject had a Grade 4 neutrophil reduction, which was not associated with a serious infection.

TABLE 18C

Adverse Events Summary

| AE, n (%) | Placebo (n = 56) | Compound 1 | | | |
|---|---|---|---|---|---|
| | | 3 mg BID (n = 55) | 6 mg BID (n = 55) | 12 mg BID (n = 55) | 18 mg BID (n = 55) |
| Any AE | 25 (45) | 26 (47) | 31 (56) | 37 (67) | 39 (71) |
| Any serious AE | 1 (2) | 2 (4) | 2 (4) | 0 | 1 (2) |
| Any severe AE | 2 (4) | 1 (2) | 2 (4) | 2 (4) | 1 (2) |
| Any AE leading to discontinuation | 2 (4) | 0 | 6 (11) | 2 (4) | 3 (5) |
| Any death | 0 | 0 | 0 | 0 | 0 |
| AEs of special interest | | | | | |
| Infection | 13 (23) | 11 (20) | 12 (22) | 22 (40) | 21 (38) |
| Serious infection | 1 (2) | 0 | 0 | 0 | 0 |
| Cardiovascular event | 0 | 0 | 1 (2)[†] | 0 | 0 |
| Herpes zoster | 2 (4) | 1 (2) | 0 | 1 (2) | 1 (2) |
| Hepatic disorder* | 1 (2) | 0 | 0 | 0 | 2 (4) |
| Malignancy | 0 | 0 | 1 (2)[‡] | 0 | 0 |

Abbreviations: AE—adverse event; BID—twice daily.
*AEs as reported by the investigator.
[†]The cardiovascular event was adjudicated as a transient ischemic attack.
[‡]One patient with basal cell and squamous cell carcinoma.
Safety population

TABLE 18D

Mean Change Over Time in Select Hematology Parameters
and Incidence of Patients With Abnormalities

| Abnormality, number (%) | Placebo (n = 56)* | Compound 1 | | | |
|---|---|---|---|---|---|
| | | 3 mg BID (n = 55)* | 6 mg BID (n = 55)* | 12 mg BID (n = 55) | 18 mg BID (n = 55) |
| Neutrophils × $10^9$/L | | | | | |
| Grade 2 (1.0-1.4) | 1 (2) | 0 | 3 (6) | 4 (7) | 7 (13) |
| Grade 3 (0.5-0.9) | 0 | 0 | 0 | 2 (4) | 1 (2) |
| Grade 4 (<0.5) | 0 | 0 | 0 | 1 (2) | 0 |
| Lymphocytes × $10^9$/L | | | | | |
| Grade 2 (1.0-1.4) | 18 (33) | 14 (26) | 19 (35) | 14 (25) | 26 (47) |
| Grade 3 (0.5-0.9) | 9 (16) | 8 (15) | 8 (15) | 11 (20) | 9 (16) |
| Grade 4 (<0.5) | 0 | 1 (2) | 1 (2) | 0 | 2 (4) |

BID—twice daily.
*1 subject with missing data.
Safety population.
Grading based on OMERACT Rheumatology Common Toxicity Criteria v.2.0

Discussion

In this study, a broad dose range of Compound 1 (dosed up to 18 mg BID) was tested to assess efficacy and safety in subjects with an inadequate response or intolerance to anti-TNF biologic therapies. At all doses, Compound 1 demonstrated rapid and robust efficacy as shown by significantly greater improvements in clinical and functional outcomes compared to placebo. The onset of improvement with Compound 1 treatment was rapid with up to 58% of subjects achieving an ACR20 response as early as 2 weeks after treatment. The proportion of ACR20 responders reached a maximum at 8 weeks and plateaued at 71% through Week 12. Improvements in ACR50 (up to 42%) and ACR70 (up to 25%) response rates in the Compound 1 groups also reached a maximum before Week 12. The speed of the response is in contrast to the 3-6 months observed for many biologic therapies (Bathon, et al., *The New England Journal of Medicine,* 2000, Vol. 343 (22), pp. 1586-93; Keystone, et al., *Arthritis and Rheumatism,* 2008, Vol. 58 (11), pp. 3319-29; Keystone, et al., *Arthritis and Rheumatism,* 2004, Vol. 50 (5), pp. 1400-11) and comparable with that observed for other JAK inhibitors, baricitinib and tofacitinib in TNF-IR patients. (Burmester, et al., *Lancet* (London, England), 2013, Vol. 381 (9865), pp. 451-60; Genovese, et al., *European League Against Rheumatism,* 2015; 2015). In addition, the ACR20 response rate was comparable between subjects with two or more prior anti TNF therapies and those with only one prior anti-TNF. In general, the maximum efficacy was observed at the 12 mg BID dose.

Despite producing significant clinical improvement in different spectra of RA patients, there are safety concerns with JAK inhibitors, predominantly around impairing the body's ability to fight infections, viral reactivation, as well as altering hematopoietic homeostasis that could link to anemia. The most commonly reported adverse events with JAK inhibitors are infections, herpes zoster, pulmonary tuberculosis, cryptococcal pneumonia and pneumocystis pneumonitis (Fleischmann, et al., Arthritis Rheumatol., 2015, Vol. 67 (2), pp. 334-43; Genovese, et al., Arthritis Rheumatol., 2016, Vol. 68 (1), pp. 46-55). In addition, increases in total cholesterol, elevation of transaminase and serum creatinine, decreases in neutrophil counts and anemia are also observed. (Burmester, et al., Lancet (London, England), 2013, Vol. 381 (9865), pp. 451-60; Genovese, et al., Arthritis Rheumatol., 2016, Vol. 68 (1), pp. 46-55; Keystone, et al., Annals of the Rheumatic Diseases, 2015, Vol. 1 74 (2), pp. 333-40).

In the current study, a broad range of doses of Compound 1 were tested to assess the selectivity of Compound 1 in vivo. Overall, Compound 1 demonstrated an acceptable safety and tolerability profile at all doses in this refractory RA population. There was no serious infection, although the proportion of overall infection rates was higher at the two highest doses of Compound 1 (12 mg and 18 mg BID). The most commonly observed infections with Compound 1 were bronchitis, upper respiratory, and urinary tract infections. The incidence of herpes zoster was similar in the placebo group (two subjects, 4%) and the Compound 1 treatment groups (three subjects, 1%), and all were non-disseminated.

At the 12 mg BID and 18 mg BID doses, there was a modest decrease in mean hemoglobin levels by Week 12, although the mean hemoglobin levels remained within the normal range. Notably, in subjects with elevated hsCRP at baseline, who were receiving 3 or 6 mg BID Compound 1, mean hemoglobin levels increased compared to placebo treatment, possibly due to a reduction of systemic inflammation while minimizing inhibitory effects on JAK2.

Circulating NK cells, which function as the critical mediator of host immunity against malignancy and infections, were measured as a pharmacodynamic readout of IL-15 inhibition. With increasing doses of Compound 1 there was a greater decrease in mean circulating NK cell counts. At the maximally efficacious dose, 12 mg BID, NK cells decreased by 28% from baseline, with proportionally smaller decreases in NK cells observed at lower doses. Given the fact that IL-15 signaling involves a heterodimer of JAK1 and JAK3, this was to be expected at higher doses of Compound 1. It is unclear how much each of the heterodimeric components (JAK1 and JAK3) contributes to the overall IL-15 signaling. However, it is possible that at higher exposure of Compound 1, the threshold for in-vivo selectivity for JAK1 compared to JAK3 is lowered in the context of the JAK1/JAK3 heterodimer. Of note, for tofacitinib at 5 mg BID, the reported median decrease in NK cells at week 24 was ~35%, with greater reduction at 10 mg BID or higher doses of tofacitinib (van Vollenhoven et al., Annals of the Rheumatic Diseases, 2015, pp. 258-9; Addendum to Primary Clinical Review, NDA 203,214, Center for Drug Evaluation and Research). However, it is important to note that the significance of NK cell reduction, especially what is considered clinically meaningful reduction in NK cells in terms of predicting clinical events (i.e. onset of viral reactivation) is lacking. A significant association with the changes in nadir NK cells and treated infection rates with tofacitinib treatment was observed (van Vollenhoven et al., Annals of the Rheumatic Diseases, 2015, pp. 258-9). No association of the reduced NK cells with clinical events was observed in the current study.

As reported with other JAK inhibitors, a dose-dependent elevation of low-density lipoprotein cholesterol and high density lipoprotein cholesterol levels was observed with Compound 1, however, the ratio of LDL-C/HDL-C remained unchanged. For the other laboratory parameters of interest, i.e, serum transaminases, WBC, neutrophil, or lymphocytes, the mean changes were unremarkable and lacked apparent dose relationship, with only one subject discontinuing the study early due to leukopenia.

In summary, the results of the current study demonstrated safety and efficacy of a selective JAK1 inhibitor, Compound 1, in a difficult-to-treat population of RA patients who had an inadequate response or intolerance to anti-TNF biologic therapies.

Example 33: Treatment of Moderately to Severely Active Rheumatoid Arthritis in Patients Who have Inadequately Responded to Methotrexate The following example briefly describes the results of a Phase 2b, 12-week, randomized, double-blind, parallel-group, placebo-controlled study in which adult subjects with moderately to severely active rheumatoid arthritis (RA) who have inadequately responded to stable methotrexate therapy were treated with Compound 1.

Patients

Men and women aged ≥18 years with active RA and inadequate response to methotrexate were included in the study. Diagnosis of RA was based on the 1987 revised American College of Rheumatology (ACR) classification criteria (Arnett et al, Arthritis Rheum., 1988, Vol. 31 (3), pp. 315-324) or the 2010 ACR/European League Against Rheumatism (EULAR) criteria (Smolen et al, Ann. Rheum. Dis., 2010, Vol. 69 (6), pp. 964-975). Active RA was defined by minimum disease activity criteria of ≥6 swollen joints (based on 66 joint counts) at screening and baseline; ≥6 tender joints (based on 68 joint counts) at screening and baseline; and high-sensitivity C-reactive protein (hsCRP) greater than the upper limit of normal (ULN) or positive test results for both rheumatoid factor and anti-cyclic citrullinated peptide (CCP) at screening. Eligible patients had been receiving methotrexate for ≥3 months, with a stable prescription (7.5-25 mg/week) for ≥4 weeks before baseline. Stable doses of methotrexate were continued throughout the study. In addition, all patients were requested to take a dietary supplement of oral folic acid (or equivalent) from 4 weeks prior to baseline and throughout study participation. All other oral disease-modifying antirheumatic drugs (DMARDs) were discontinued before baseline for ≥5 times the mean terminal elimination half-life of the specific DMARD to ensure washout. High-potency opiates (e.g., oxycodone, methadone, morphine) were discontinued ≥4 weeks before baseline. All patients had a negative tuberculosis screening assessment or, if there was evidence of a latent tuberculosis infection, completed ≥2 weeks of tuberculosis prophylaxis or had documented completion of a full course of tuberculosis prophylaxis before baseline. Patients were allowed to receive nonsteroidal anti-inflammatory drugs, acetaminophen, oral/inhaled corticosteroids, and low-potency opiates. Patients were excluded if they had received JAK inhibitor therapy or any other investigational or approved biologic RA therapy.

Treatment

Patients were randomized in a 1:1:1:1:1:1 ratio in a double-blind manner to oral doses of Compound 1 (immediate release capsules comprising Tartrate Hydrate) 3 mg BID, 6 mg BID, 12 mg BID, 18 mg BID, or 24 mg QD (two 12 mg tablets administered at the same time), or placebo BID for 12 weeks. Patients were randomized using an interactive voice/web response system according to a blocked randomization schedule. Investigators, patients, and other study personnel were blinded to the treatment assignments throughout the study. To maintain blinding, the placebo and active treatments had an identical appearance. Patients were instructed to take their doses (6 capsules total, split into 2 batches of 3) at approximately the same times each day.

Assessments

The primary efficacy endpoint was a ≥20% improvement in ACR criteria (ACR20) at week 12. Other endpoints included ACR50 and ACR70 response rates; change in 28-joint Disease Activity Score using C-reactive protein (DAS28 (CRP)); change in Clinical Disease Activity Index (CDAI); the proportion of patients achieving low disease activity (LDA) or clinical remission based on DAS28 (CRP) and CDAI criteria; and change in the Health Assessment Questionnaire Disability Index (HAQ-DI). The minimal clinically important difference (MCID) on the HAQ-DI, which is a decrease of ≥0.22, (Strand et al, 2006) was also evaluated.

Safety was evaluated during treatment and for 30 days after the last dose of study drug on the basis of adverse events (AEs), vital signs, physical examinations, and laboratory tests. AEs were coded using the Medical Dictionary for Regulatory Activities (MeDRA), version 17.1.

Statistical Analyses

The per-protocol primary efficacy analysis was conducted in a modified intent-to-treat population, including all randomized patients who take at least 1 dose of study drug, with last observation carried forward (LOCF) imputation; data were also analyzed with nonresponder imputation (NRI). Statistical tests were 1-sided with a significance level of 0.05 for efficacy analyses and 2-sided with a significance level of 0.05 for all other analyses. A sample of 270 patients (45 per randomized treatment group) was targeted give 80% power to establish a real difference of 30% in the primary efficacy endpoint (ACR20 response rate at week 12), assuming the response rate would be 30% in the placebo group and 60% in at least 1 of the Compound 1 dose groups.

Results

Patients

Figure 5A:
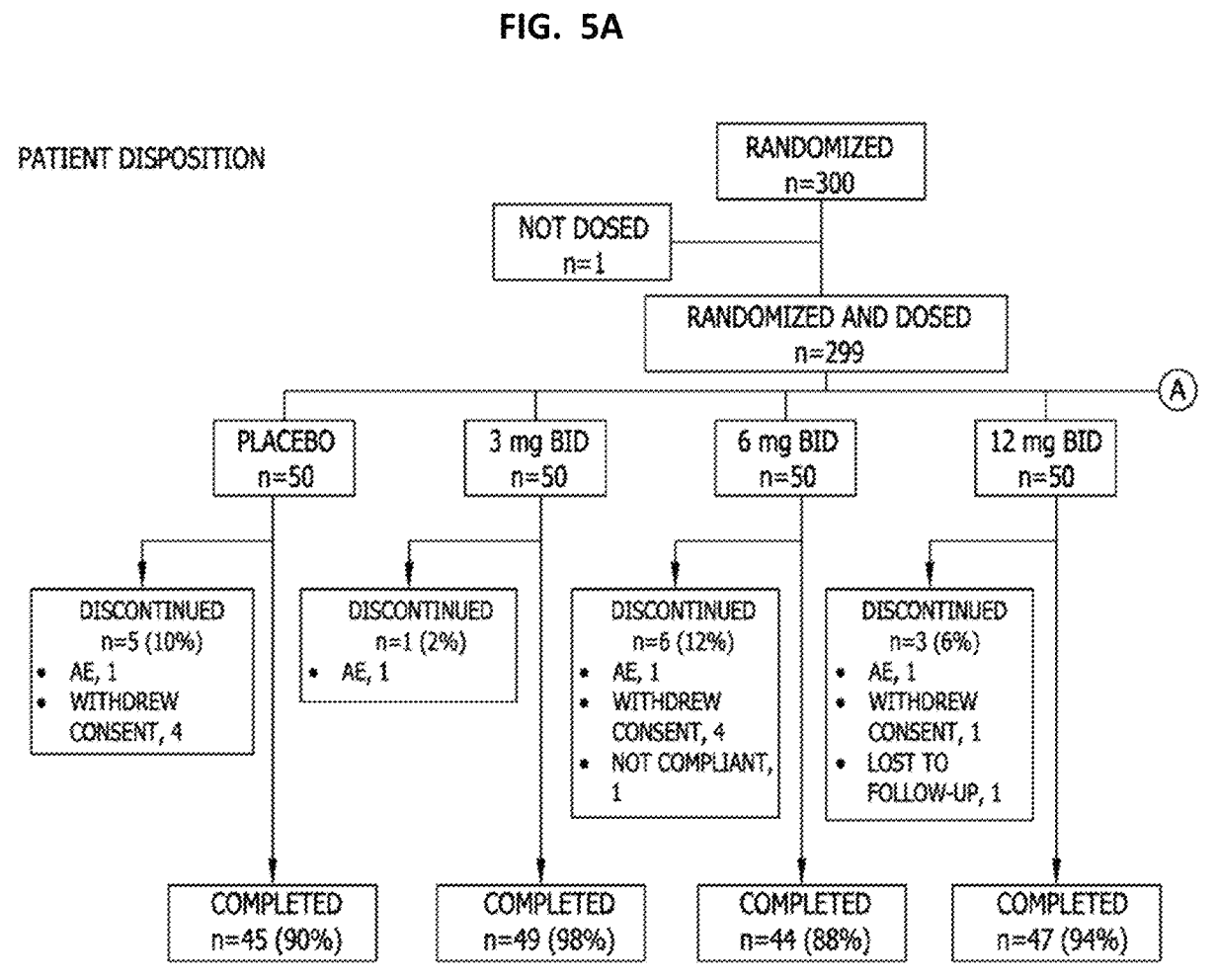
Figure 5B:
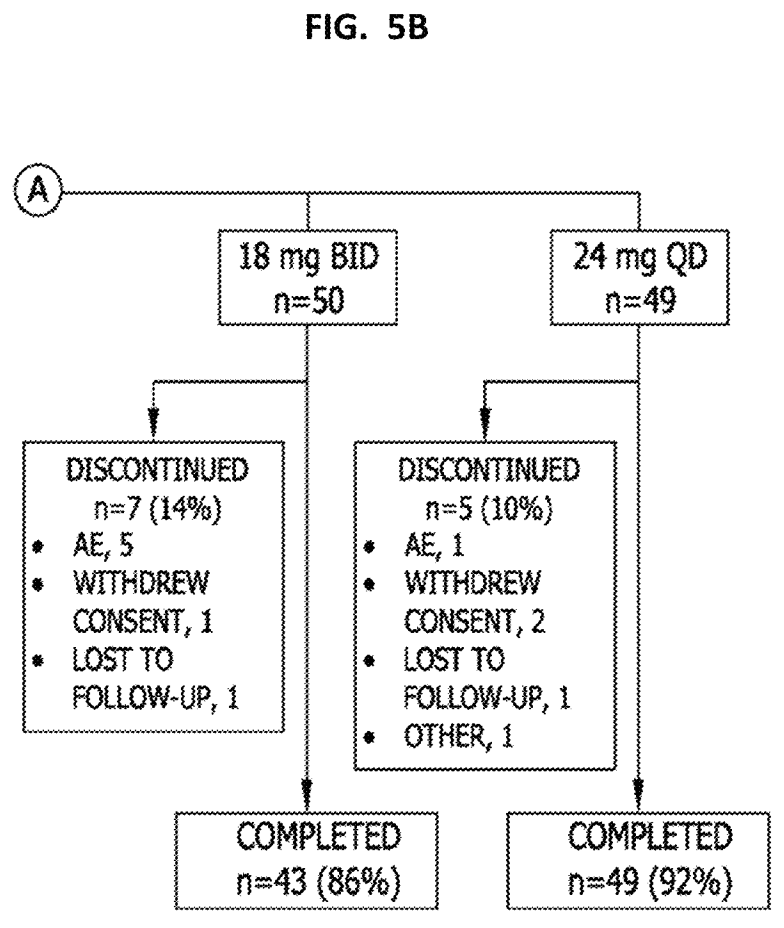

A total of 300 patients were randomized, and 299 received placebo (n=50) or Compound 1 3 mg BID (n=50), 6 mg BID (n=50), 12 mg BID (n=50), 18 mg BID (n=50), or 24 mg QD (n=49). Overall, 91% of patients completed the study, with similar discontinuation rates across treatment groups and no apparent relationship between Compound 1 dose and discontinuation (FIGS. 5A and 5B). Demographic and clinical characteristics at baseline were balanced among treatment groups (Table 19A). Patients were from Eastern Europe (61%), Central/South America (18%), the United States (10%), Western Europe (8%), or other regions (4%). Patients had a mean disease duration of 6.9 years and 17.7% had used ≥1 prior non-methotrexate DMARD. Of note, patients with normal hsCRP could be enrolled if they were positive for rheumatoid factor and anti-CCP antibody. Approximately 43% of patients had hsCRP values ≤ULN at baseline.

TABLE 19A

Baseline Characteristics and Disease Activity in
Patients with Inadequate Response to Methotrexate

| | | Compound 1 | | | | |
|---|---|---|---|---|---|---|
| Characteristic | Placebo (n = 50) | 3 mg BID (n = 50) | 6 mg BID (n = 50) | 12 mg BID (n = 50) | 18 mg BID (n = 50) | 24 mg QD (n = 49) |
| Female, number (%) | 38 (76) | 40 (80) | 34 (68) | 41 (82) | 42 (84) | 42 (86) |
| Age, years, mean (SD) | 55 (12) | 53 (12) | 55 (12) | 56 (12) | 55 (14) | 56 (12) |
| Years since RA diagnosis, mean (SD) | 5.9 (5.3) | 3.9 (3.8) | 7.0 (5.5) | 9.3 (8.6) | 7.3 (7.9) | 8.3 (7.1) |
| RF positive, number (%) | 41 (82) | 45 (90) | 46 (92) | 44 (88) | 41 (82) | 44 (90) |
| Anti-CCP positive, number (%) | 39 (78) | 40 (80) | 45 (90) | 43 (86) | 40 (80) | 45 (92) |
| Methotrexate dose, mg, mean (SD) | 16 (4) | 16 (4) | 16 (4) | 14 (4) | 15 (5) | 15 (4) |

TABLE 19A-continued

| | Baseline Characteristics and Disease Activity in Patients with Inadequate Response to Methotrexate | | | | | |
|---|---|---|---|---|---|---|
| | | | Compound 1 | | | |
| Characteristic | Placebo (n = 50) | 3 mg BID (n = 50) | 6 mg BID (n = 50) | 12 mg BID (n = 50) | 18 mg BID (n = 50) | 24 mg QD (n = 49) |
| Prednisolone dose, mg, mean (SD) | 0 | | | 0 | 0 | 0 |
| ≥1 prior non-MTX DMARD, number (%) | 7 (14) | 6 (12) | 12 (24) | 11 (22) | 5 (10) | 12 (24) |
| 1 | 6 (12) | 4 (8) | 10 (20) | 9 (18) | 2 (4) | 8 (16) |
| 2 | 1 (2) | 2 (4) | 1 (2) | 1 (2) | 1 (2) | 3 (6) |
| ≥3 | 0 | 0 | 1 (2) | 1 (2) | 2 (4) | 1 (2) |
| | | | Disease Activity | | | |
| TJC68, mean (SD) | 29 (16) | 27 (15) | 28 (16) | 28 (13) | 27 (15) | 28 (16) |
| SJC66, mean (SD) | 19 (12) | 15 (8) | 19 (12) | 17 (11) | 17 (12) | 18 (13) |
| HAQ-DI, mean (SD) | 1.4 (0.7) | 1.3 (0.7) | 1.6 (0.7) | 1.5 (0.6) | 1.6 (0.6) | 1.5 (0.7) |
| DAS28(CRP), mean (SD) | 5.6 (1.1) | 5.5 (1.1) | 5.8 (1.0) | 5.6 (0.9) | 5.7 (0.8) | 5.7 (1.0) |
| CDAI, mean (SD) | 40 (14) | 38 (13) | 43 (14) | 39 (12) | 40 (13) | 41 (13) |
| hsCRP, mg/L, mean (SD) | 15 (26) | 11 (15) | 17 (20) | 11 (15) | 13 (15) | 14 (16) |
| hsCRP >ULN,* number (%) | 27 (54) | 25 (50) | 31 (62) | 26 (52) | 28 (56) | 33 (67) |

Efficacy

Figure 6:
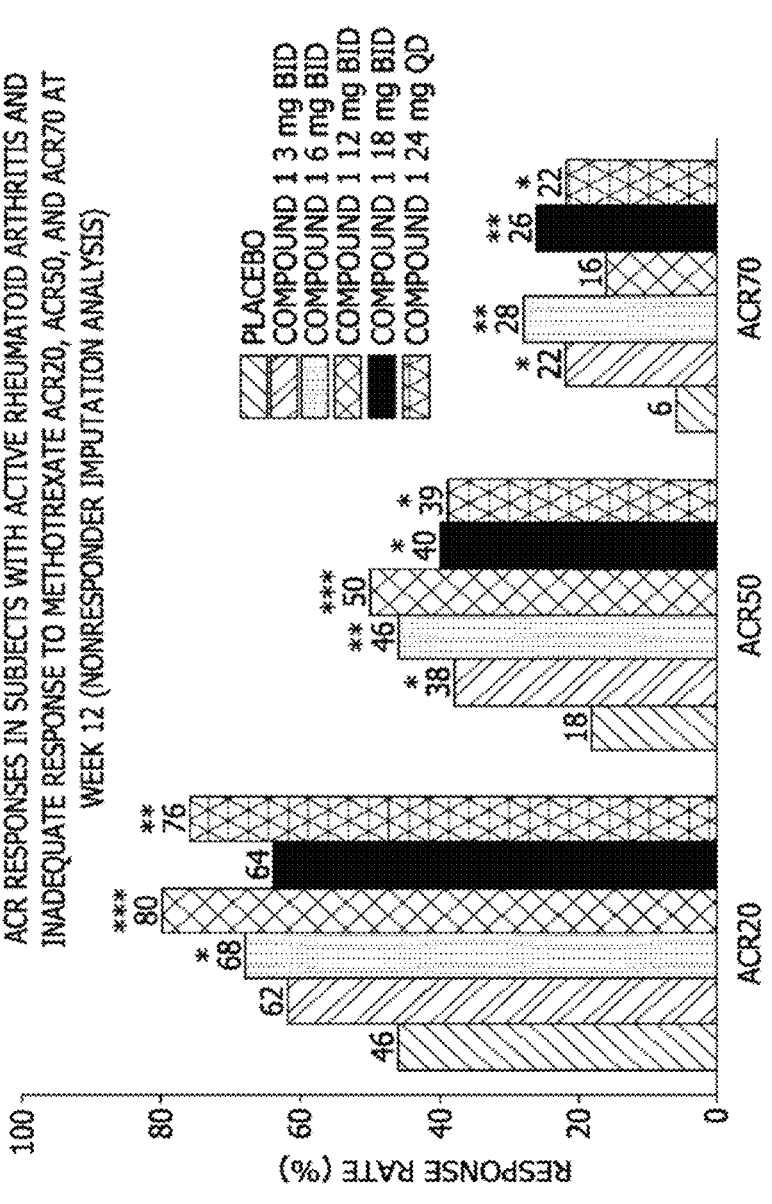
FIG. 6 shows the ACR20, ACR50, and ACR70 responses at week 12 following administration of placebo or various doses of Compound 1 to subjects with active rheumatoid arthritis and inadequate response to methotrexate (*P<0.05;  P<0.01; * P<0.001 relative to placebo; modified intent-to-treat population with NRI of missing values).
Figure 7A:
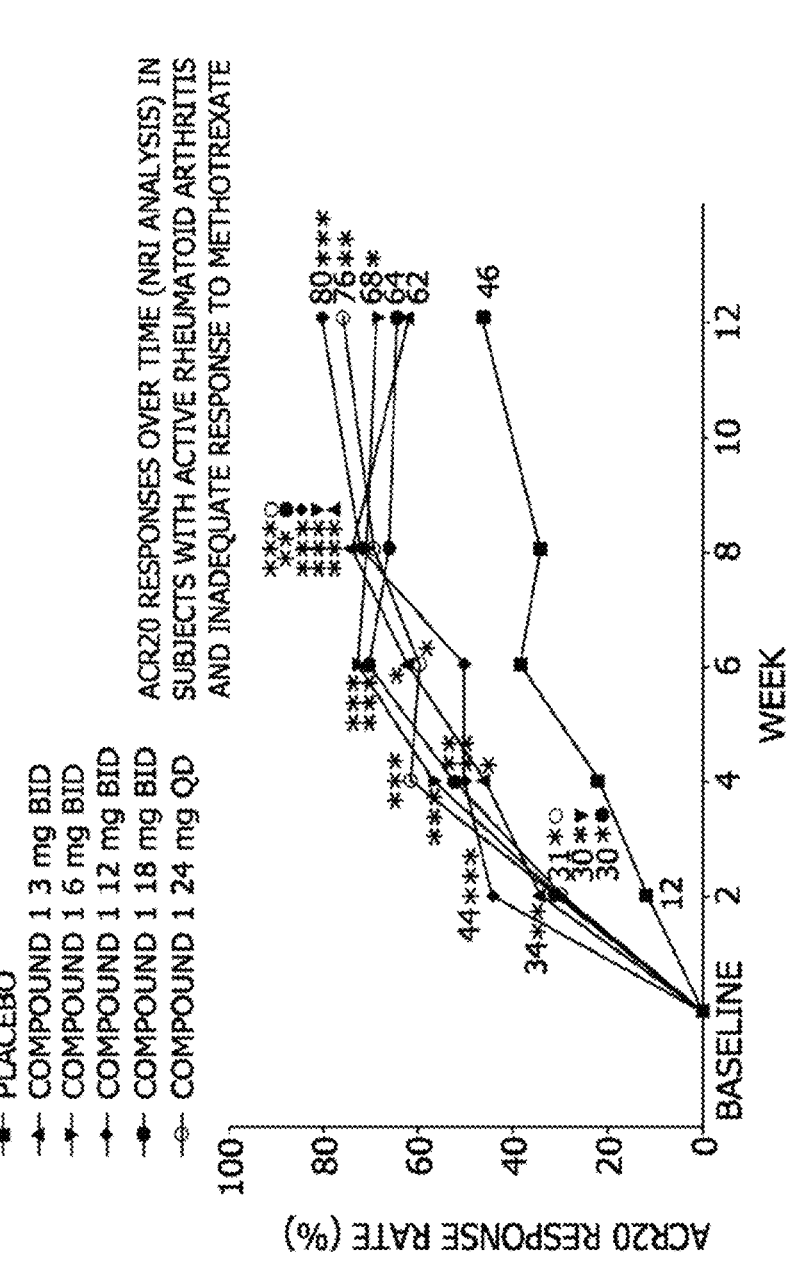
FIGS. 7A-7D show the ACR20 (FIG. 7A, NRI analysis), ACR50 (FIG. 7B, NRI analysis), and ACR70 (FIG. 7C, NRI analysis) responses or DAS28 (CRP) mean change from baseline (FIG. 7D, observed cases) over time following administration of placebo or various doses of Compound 1 to subjects with active rheumatoid arthritis and inadequate response to methotrexate (*P<0.05;  P<0.01; * P<0.001 relative to placebo; modified intent-to-treat population).
Figure 7B:
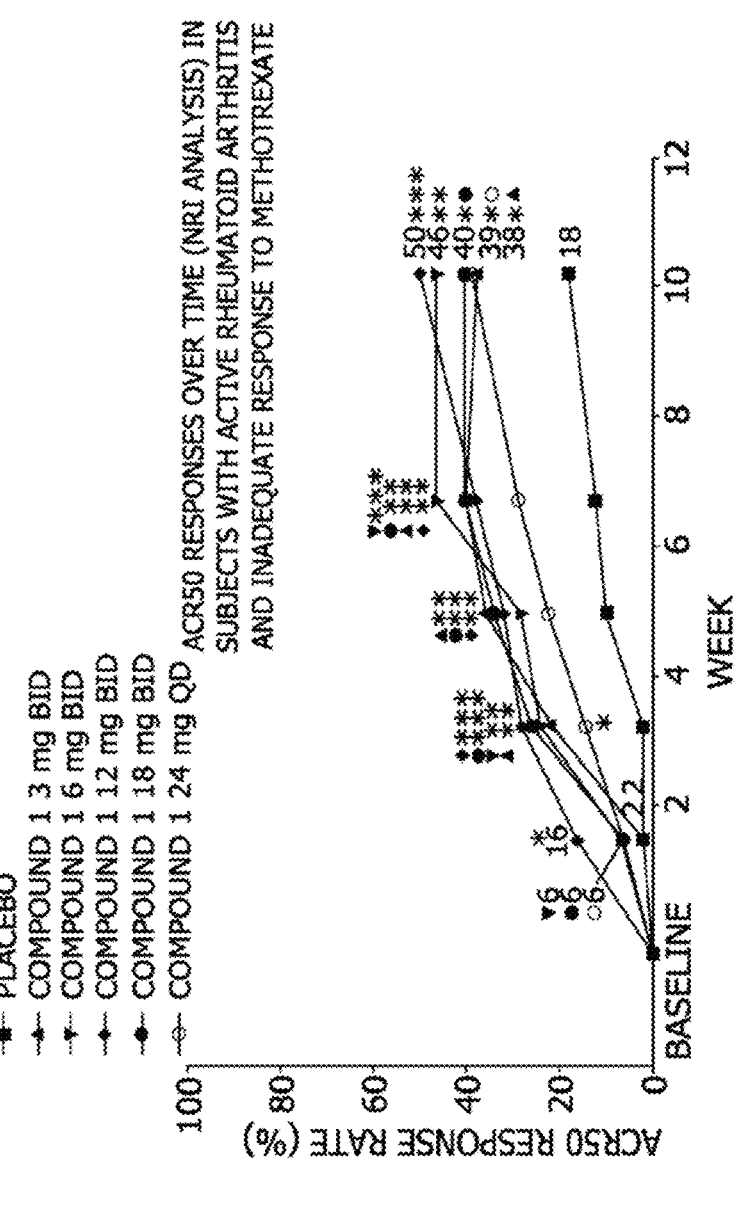
Figure 7C:
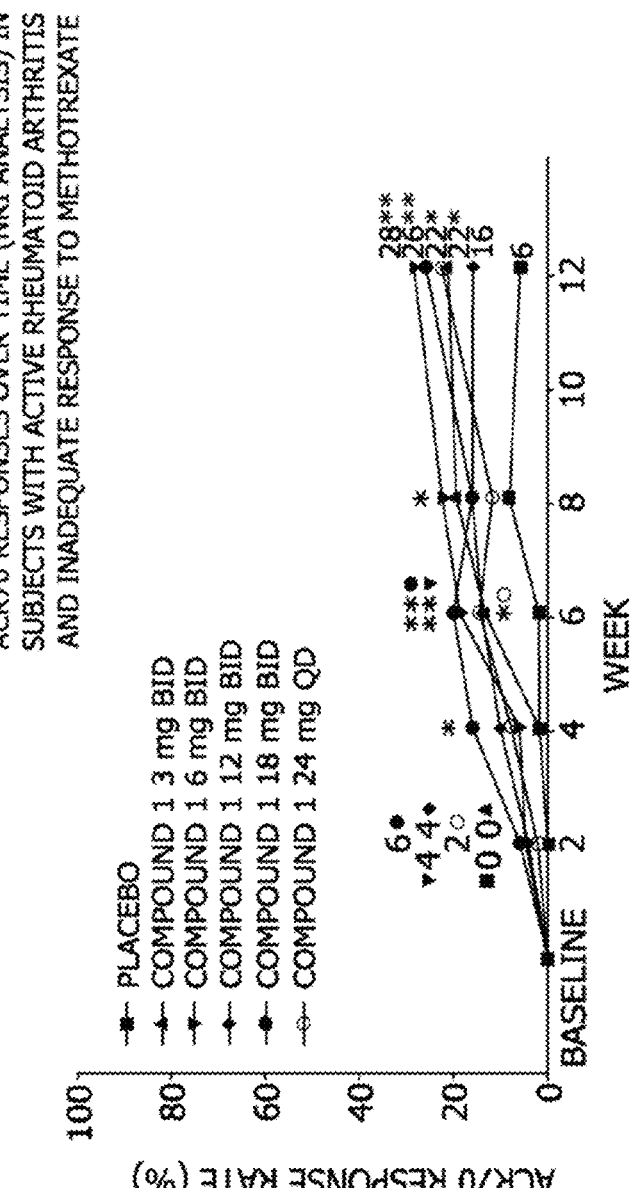
Figure 7D:
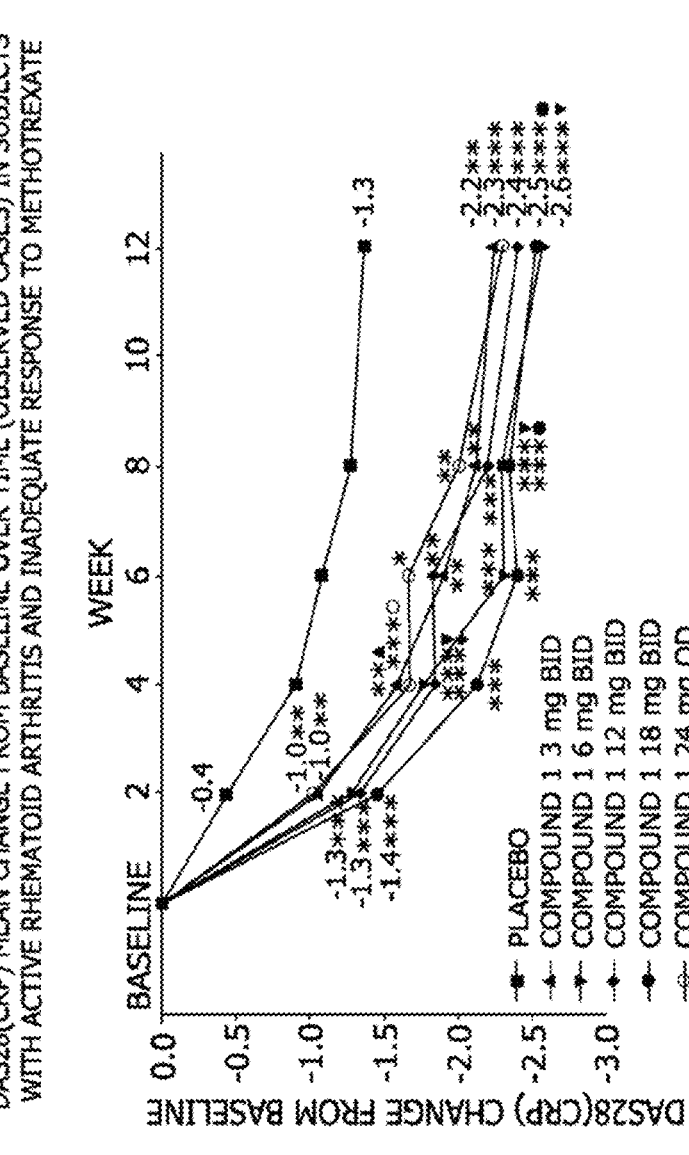

The primary per-protocol endpoint, ACR20 at week 12 (LOCF imputation), was met at every dose of Compound 1 except the lowest dose of 3 mg BID. The proportions of patients with ACR20 were 65% (P=0.153), 73% (P=0.18), 82% (P=0.001), 77% (P=0.008), and 82% (P=0.001) at 3 mg BID, 6 mg BID, 12 mg BID, 18 mg BID, and 24 mg QD, respectively, versus the placebo response rate (50%). ACR20 responses (NRI) were significantly higher with Compound 1 at 6 mg BID (68%), 12 mg BID (80%), and 24 mg QD (76%) versus placebo (46%; FIG. 6). Responses with more stringent criteria, i.e., ACR50 and ACR70, were achieved at week 12 by significantly higher percentages of patients who received Compound 1 versus placebo at all doses except 12 mg BID for ACR70 response (NRI; FIG. 6). ACR20 response rates increased over time with Compound 1 to reach mean maximum values at weeks 6 to 12 (FIG. 7A). ACR50 responses were significant from week 4 onward and plateaued at week 8 (FIG. 7B); ACR70 responses also appeared to plateau by week 8, with some further improvements up to week 12 (FIG. 7C). At the first assessment (week 2), ACR20 responses with Compound 1 ranged from 30% to 44% and were significantly higher at all doses in patients who received Compound 1 versus placebo (12%). Mean decreases in DAS28 (CRP) improved over time from baseline, ranging from −2.2 to −2.6 with Compound 1 at week 12, and were significantly lower compared with placebo (−1.3) at all Compound 1 doses and every time point (FIG. 7D).

Figure 8A:
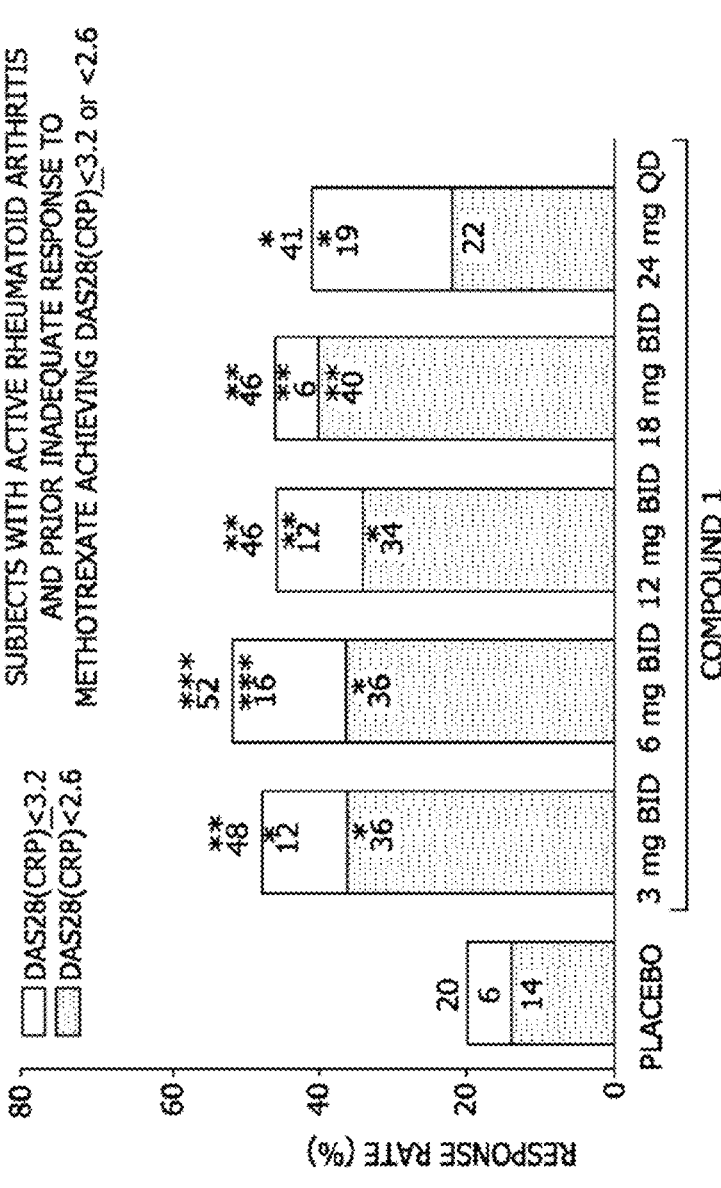
FIGS. 8A and 8B show subjects achieving a DAS28 (CRP) score of ≤3.2 or <2.6 (FIG. 8A) or CDAI of ≤10 or ≤2.8) at week 12 following administration of placebo or various doses of Compound 1 to subjects with active rheu-matoid arthritis and inadequate response to methotrexate (*P<0.05;  P<0.01; * P<0.001 relative to placebo; modified intent-to-treat population (NRI)). For FIGS. 8A and 8B, the bottom number indicates the percentage of subjects who achieved both cutoff values, the middle num-ber indicates the percentage of subjects who achieved the less stringent cutoff but not the more stringent cutoff value, and the top number indicates the percentage of patients who achieved either cutoff value.
Figure 8B:
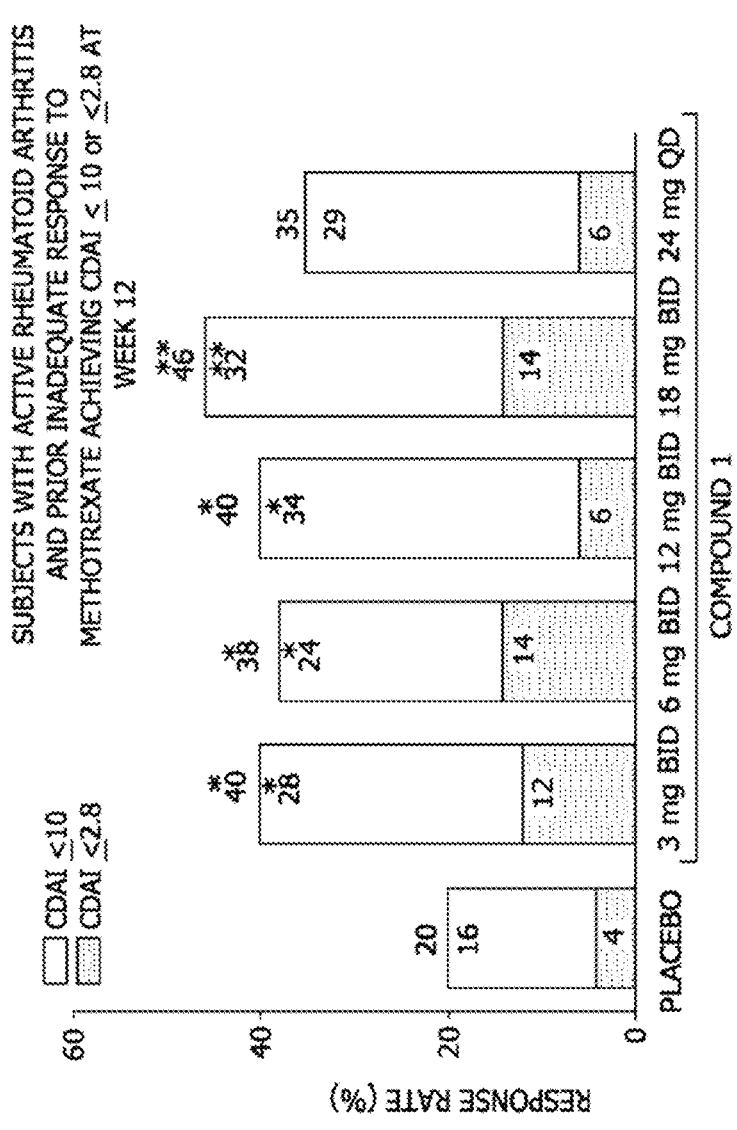

Higher percentages of patients who received Compound 1 achieved DAS28 (CRP)≤3.2 or <2.6 compared with placebo. The DAS28 (CRP)≤3.2 cutoff was achieved by a significantly higher percentage of patients (41%-52%) at all doses of Compound 1 compared with placebo (20%); the <2.6 cutoff was achieved by significantly higher proportions (34%-40%) with Compound 1 compared with placebo (14%) at all doses except 24 mg QD (22%; FIG. 8A). Similarly, CDAI≤10 was achieved by a significantly higher percentage of patients (40%-46%) compared with placebo (20%) with Compound 1 at all doses except 24 mg QD (35%; FIG. 8B).

Improvements from baseline in ACR component scores were larger with Compound 1 compared with placebo, reaching statistical significance for most comparisons at doses of 6 mg BID and greater (Table 19B). Changes from baseline on the HAQ-DI at week 12 with Compound 1 ranged from −0.6 to −0.8 and were significantly greater than that seen with placebo (−0.4) for all but the Compound 1 24 mg QD dose (−0.6). Numerically, more patients in the Compound 1 dose groups ≥6 mg BID (69%-88%) met the MCID at week 12 compared with placebo (67%); the study was not powered for this analysis, and the comparisons versus placebo mostly were not statistically significant.

TABLE 19B

| | Mean Changes from Baseline in ACR Components at Week 12 | | | | | |
|---|---|---|---|---|---|---|
| | | | Compound 1 | | | |
| ACR Component | Placebo (n = 50) | 3 mg BID (n = 50) | 6 mg BID (n = 50) | 12 mg BID (n = 50) | 18 mg BID (n = 50) | 24 mg QD (n = 49) |
| TJC68 | −14.4 | −15.9 | −19.2* | −19.2* | −17.4 | −18.9* |
| SJC66 | −9.9 | −12.1 | −11.9 | −12.7* | −13.2* | −13.1* |

TABLE 19B-continued

| | | | Compound 1 | | | |
|---|---|---|---|---|---|---|
| | | 3 mg | 6 mg | 12 mg | 18 mg | 24 mg |
| ACR | Placebo | BID | BID | BID | BID | QD |
| Component | (n = 50) | (n = 50) | (n = 50) | (n = 50) | (n = 50) | (n = 49) |

Mean Changes from Baseline in ACR Components at Week 12

| ACR Component | Placebo (n = 50) | 3 mg BID (n = 50) | 6 mg BID (n = 50) | 12 mg BID (n = 50) | 18 mg BID (n = 50) | 24 mg QD (n = 49) |
|---|---|---|---|---|---|---|
| Patient's assessment of pain | −19.9 | −25.3 | −33.8** | −33.4** | −34.9** | −29.8* |
| Physician's global assessment of disease activity | −28.0 | −34.7 | −43.0*** | −45.6** | −36.6* | −37.6* |
| Patient's global assessment of disease activity | −17.5 | −26.9 | −31.4** | −23.8 | −29.1* | −24.1 |
| HAQ-DI | −0.4 | −0.6* | −0.7** | −0.8*** | −0.6* | −0.6 |
| HAQ-DI ≤MCID,§ number (%), 95% CI | 30 (67), 53-80 | 33 (67), 54-81 | 34 (69), 57-82 | 44 (88), 79-97 | 35 (74), 62-87 | 38 (78), 66-89 |
| hsCRP | −0.4 | −10.5*** | −8.8*** | −8.9*** | −7.5** | −8.4*** |

Abbreviations: ACR—American College of Rheumatology; BID—twice daily; HAQ-DI—Health Assessment Questionnaire Disability Index; hsCRP—high-sensitivity C—reactive protein; LOCF—last observation carried forward; MCID—minimal clinically important difference; QD—once daily; RA—rheumatoid arthritis; SJC66—swollen joint count using 66 joints; TJC68—tender joint count using 68 joints.
*P < 0.05;
**P < 0.01;
***P < 0.001 relative to placebo.
§MCID = −0.22.
Modified intent-to-treat population with LOCF imputation of missing values.
95% CIs were calculated based on a normal approximation to the binomial distribution.

As can be seen from these results, Compound 1 had an early onset of action in subjects who have demonstrated a prior inadequate response to methotrexate. In particular, ACR20 response rates improved starting at week 2, with a maximum effect achieved as early as week 6, with continued improvement in some dose groups through week 12. ACR50 (maximum efficacy up to 50%) and ACR70 (maximum efficacy up to 28%) response rates also quickly plateaued by about week 8. Compound 1 showed a dose-dependent efficacy that seemed to reach a maximum at 12 mg BID.

Safety

The safety and tolerability profile of Compound 1 across doses was acceptable (Table 19C). Incidence of any AE was statistically significantly higher with Compound 1 overall versus placebo (45% vs 26%; P=0.012), with a trend of dose dependence. Among common AEs, those that occurred in ≥3% patients in any group were abdominal pain, abdominal pain upper, back pain, blood creatine phosphokinase increased, cough, diarrhea, dyslipidemia, dyspepsia, gastroenteritis, headache, herpes zoster, influenza, leukopenia, nasopharyngitis, upper respiratory tract infection, urinary tract infection, white blood cell count decreased, and wound. Most AEs in the Compound 1 treatment groups were mild or moderate in severity. Severe AEs occurred in 1 patient each with Compound 1 at 6 mg BID (lung cancer at posttreatment day 10 in a 79-year-old male patient with family and smoking histories; the patient died 3 months later), 12 mg BID (pyrexia), 18 mg BID (hyperbilirubinemia), and 24 mg QD (head injury). There were 2 serious AEs with Compound 1 that were considered possibly related to study drug: community-acquired pneumonia at 12 mg BID and syncope at 24 mg QD. Infections overall occurred in 20% of patients who received Compound 1 and 14% who received placebo, with no tendency towards higher rates at higher doses. Three herpes zoster infections, 1 with Compound 1 at 3 mg BID and 2 at 24 mg QD, involved 1 dermatome per patient. A patient in the Compound 1 6 mg BID group, aged 79 years and with a history of smoking, was diagnosed with lung cancer 10 days after stopping study treatment and died 3 months later.

At week 12, mean values for alanine aminotransferase (ALT) were significantly higher with Compound 1 18 mg BID than with placebo; mean values for aspartate aminotransferase (AST) were significantly higher than placebo with all Compound 1 doses >3 mg BID (Table 19D). However, grade 3/4 ALT or AST abnormalities during the study were sporadic, with no clear dose dependence (Table 23E). Creatinine and creatine phosphokinase levels were significantly higher in all Compound 1 dose groups compared with placebo. Compound 1 was associated with elevations in high-density and low-density lipoprotein cholesterol (HDL-C; LDL-C); HDL-C elevation was statistically significant at 6 mg BID, whereas LDL-C values were significantly higher than placebo for all Compound 1 doses; however, the ratios of LDL-C/HDL-C remained the same through week 12. There were no significant decreases in lymphocyte or neutrophil levels between placebo and Compound 1 dose groups by week 12. Grade 3 lymphocyte values occurred with placebo and all doses of Compound 1; grade 4 values occurred in 1 patient each with Compound 1 at 3 mg BID and 18 mg BID (Table 19E). Grade 3 neutrophil values occurred with Compound 1 at 12 mg BID (1 patient), 18 mg BID (3 patients), and 24 mg QD (1 patient). Natural killer (NK) cell percentages were significantly lower than placebo with Compound 1 doses ≥6 mg BID (Table 23D).

Figure 9B:
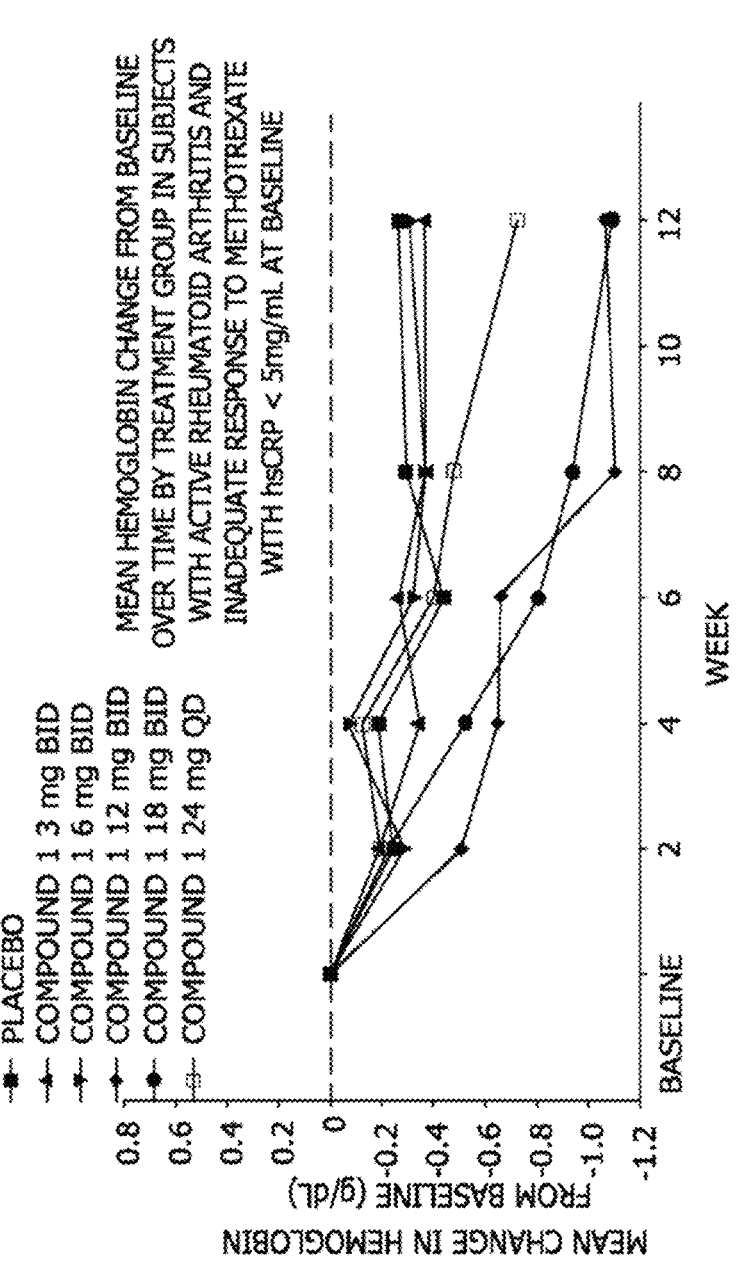
Figure 9C:
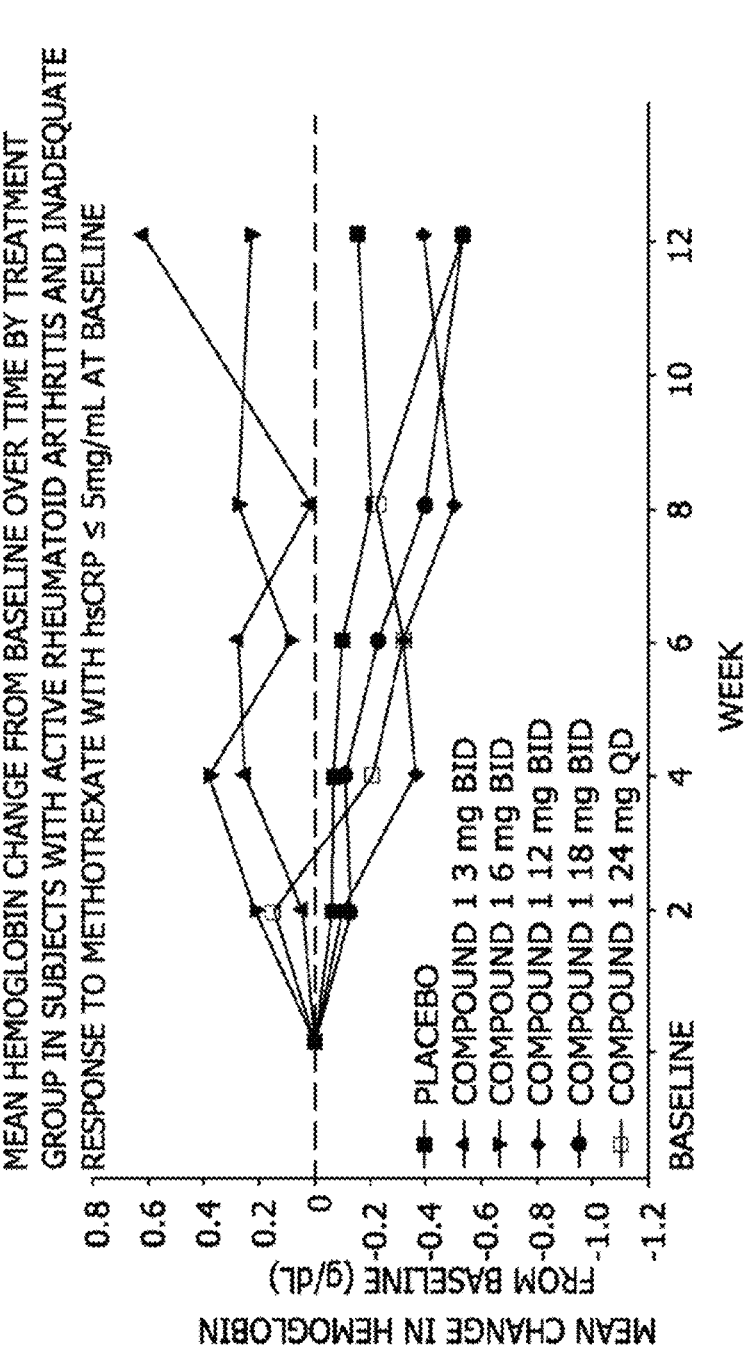

Mean changes in hemoglobin over time in all patients, patients with hsCRP values ≤5 mg/mL, and patients with hsCRP values >5 mg/mL are shown in FIGS. 9A-9C. Mean hemoglobin values remained stable or increased at lower doses, most notably in patients with elevated CRP at baseline. Dose-dependent decreases in hemoglobin were seen at higher doses without clinical impact.

TABLE 19C

| | | | Compound 1 | | | |
|---|---|---|---|---|---|---|
| AE, number (%) | Placebo (n = 50) | 3 mg BID (n = 50) | 6 mg BID (n = 50) | 12 mg BID (n = 50) | 18 mg BID (n = 50) | 24 mg QD (n = 49) |
| Adverse Events Summary | | | | | | |
| Overall AEs | | | | | | |
| Any AE | 13 (26) | 19 (38) | 23 (46) | 29 (58) | 25 (50) | 17 (35) |
| Any AE possibly drug related* | 6 (12) | 5 (10) | 6 (12) | 17 (34) | 11 (22) | 5 (10) |
| Any serious AE | 0 | 0 | 2 (4) | 1 (2) | 3 (6) | 2 (4) |
| Any serious AE possibly drug related* | 0 | 0 | 0 | 1 (2) | 0 | 1 (2) |
| Any severe AE | 0 | 0 | 1 (2) | 1 (2) | 1 (2) | 1 (2) |
| Any AE leading to discontinuation | 1 (2) | 1 (2) | 1 (2) | 1 (2) | 5 (10) | 1 (2) |
| Any AE leading to death | 0 | 0 | 0 | 0 | 0 | 0 |
| AEs ≥3% in any group | | | | | | |
| Abdominal pain | 0 | 1 (2) | 1 (2) | 2 (4) | 0 | 1 (2) |
| Abdominal pain upper | 0 | 0 | 0 | 2 (4) | 1 (2) | 1 (2) |
| Back pain | 0 | 1 (2) | 3 (6) | 1 (2) | 0 | 1 (2) |
| Blood creatine phosphokinase increased | 0 | 0 | 0 | 3 (6) | 2 (4) | 1 (2) |
| Cough | 0 | 1 (2) | 1 (2) | 3 (6) | 1 (2) | 0 |
| Diarrhea | 0 | 0 | 1 (2) | 3 (6) | 1 (2) | 1 (2) |
| Dyslipidemia | 0 | 1 (2) | 0 | 3 (6) | 0 | 0 |
| Dyspepsia | 1 (2) | 0 | 0 | 0 | 2 (4) | 0 |
| Gastroenteritis | 0 | 2 (4) | 0 | 0 | 0 | 1 (2) |
| Headache | 1 (2) | 2 (4) | 1 (2) | 3 (6) | 0 | 1 (2) |
| Herpes zoster | 0 | 1 (2) | 0 | 0 | 0 | 2 (4) |
| Influenza | 0 | 0 | 0 | 4 (8) | 1 (2) | 0 |
| Leukopenia | 0 | 0 | 0 | 3 (6) | 1 (2) | 0 |
| Nasopharyngitis | 1 (2) | 1 (2) | 2 (4) | 4 (8) | 2 (4) | 3 (6) |
| Upper respiratory tract infection | 0 | 0 | 1 (2) | 1 (2) | 2 (4) | 0 |
| Urinary tract infection | 2 (4) | 2 (4) | 2 (4) | 2 (4) | 0 | 2 (4) |
| White blood cell count decreased | 0 | 0 | 1 (2) | 0 | 2 (4) | 0 |
| Wound | 0 | 0 | 2 (4) | 0 | 0 | 0 |
| AEs of special interest | | | | | | |
| Infection | 7 (14) | 10 (20) | 7 (14) | 12 (24) | 11 (22) | 9 (18) |
| Serious infection | 0 | 0 | 0 | 1 (2) | 0 | 0 |
| Cardiovascular event | 0 | 0 | 0 | 0 | 0 | 1 (2)* |
| Herpes zoster† | 0 | 1 (2) | 0 | 0 | 0 | 2 (4) |
| Hepatic disorder | 0 | 0 | 0 | 0 | 2 (4) | 0 |
| Malignancy | 0 | 0 | 1 (2)‡ | 0 | 0 | 0 |

Abbreviations: AE—adverse event; BID—twice daily; QD—once daily.

*The cardiovascular event was a cerebrovascular accident and was adjudicated as an ischemic stroke.

†The events of herpes zoster involved 1 dermatome per patient.

‡Lung cancer at posttreatment day 10 in a 79-year-old male patient with family and smoking histories. The patient died 3 months later.

Safety analysis population.

TABLE 19D

| | | | Compound 1 | | | |
|---|---|---|---|---|---|---|
| Mean (SD) Value | Placebo (n = 50) | 3 mg BID (n = 50) | 6 mg BID (n = 50) | 12 mg BID (n = 50) | 18 mg BID (n = 50) | 24 mg QD (n = 49) |
| Mean Changes in Laboratory Values of Interest at Week 12 | | | | | | |
| ALT, U/L | −1.3 (15.4) | −1.1 (20.7) | 6.5 (10.0) | 7.0 (31.8) | 8.5 (18.5)* | 5.3 (20.7) |

TABLE 19D-continued

| | | | | | | |
|---|---|---|---|---|---|---|
| | | Compound 1 | | | | |
| Mean (SD) Value | Placebo (n = 50) | 3 mg BID (n = 50) | 6 mg BID (n = 50) | 12 mg BID (n = 50) | 18 mg BID (n = 50) | 24 mg QD (n = 49) |
| AST, U/L | −0.1 | 1.9 | 6.6 | 7.6 | 7.7 | 4.8 |
| | (8.4) | (11.9) | (5.5)** | (14.3)** | (11.3)** | (10.9)* |
| HDL-C, | 0.01 | 0.12 | 0.17 | 0.13 | 0.13 | 0.13 |
| mmol/L | (0.21) | (0.32) | (0.26)* | (0.30) | (0.43) | (0.33) |
| LDL-C, | −0.05 | 0.28 | 0.34 | 0.49 | 0.27 | 0.32 |
| mmol/L | (0.43) | (0.82)* | (0.71)* | (0.93)** | (0.83)* | (0.62)** |
| Creatinine, | −0.9 | 2.0 | 4.9 | 4.3 | 4.6 | 5.4 |
| $\mu$mol/L | (7.9) | (8.2)** | (9.1)** | (7.1)** | (10.2)** | (8.5)** |
| Creatine | −7.7 | 40.2 | 82.5 | 100.4 | 108.7 | 59.4 |
| phosphokinase, | (90.1) | (46.5)* | (80.6)** | (126.5)** | (140.2)** | (94.0)** |
| U/L | | | | | | |
| Lymphocytes, $\times 10^9$/L | −0.09 | 0.12 | 0.01 | −0.08 | −0.12 | −0.13 |
| | (0.50) | (0.58) | (0.79) | (0.67) | (0.53) | (0.49) |
| Neutrophils, $\times 10^9$/L | −0.5 | −1.1 | −0.9 | −0.9 | −0.9 | −0.4 |
| | (2.20) | (2.13) | (1.60) | (1.90) | (2.16) | (1.99) |
| NK cells, | −0.1 | −1.3 | −3.1 | −3.3 | −5.3 | −4.9 |
| CD3−/16−/ | (4.46) | (4.54) | (4.09)** | (4.67)* | (4.24)* | (5.12)** |
| 56+, %[†] | | | | | | |

Abbreviations: ALT—alanine aminotransferase; AST—aspartate aminotransferase; BID—twice daily; HDL-C—high-density lipoprotein cholesterol; LDL-C—low-density lipoprotein cholesterol; NK—natural killer; QD—once daily.

*P < 0.05;

**P < 0.01 relative to placebo; P value for difference between treatment groups in baseline and mean change from baseline using a contrast within the one-way analysis of variance.

[†]Mean percentage change from baseline at week 12.

Safety analysis population.

TABLE 19E

| | | | | | | |
|---|---|---|---|---|---|---|
| Incidence of Patients with Laboratory Abnormalities at Week 12 | | | | | | |
| | | Compound 1 | | | | |
| | Placebo (n = 50) | 3 mg BID (n = 50) | 6 mg BID (n = 50) | 12 mg BID (n = 50) | 18 mg BID (n = 50) | 24 mg QD (n = 49) |
| ALT, U/L | | | | | | |
| Grade 3 (3.0-8.0 × ULN) | 0 | 0 | 1 | 2 | 1 | 0 |
| Grade 4 (>8.0 × ULN) | 0 | 0 | 0 | 0 | 1 | 0 |
| AST, U/L | | | | | | |
| Grade 3 (3.0-8.0 × ULN) | 0 | 1 | 1 | 0 | 1 | 0 |
| Grade 4 (>8.0 × ULN) | 0 | 0 | 0 | 0 | 0 | 0 |
| Neutrophils, $\times 10^9$/L | | | | | | |
| Grade 3 (0.5-0.9) | 0 | 0 | 0 | 1 | 3 | 1 |
| Grade 4 (<0.5) | 0 | 0 | 0 | 0 | 0 | 0 |
| Lymphocytes, $\times 10^9$/L | | | | | | |
| Grade 3 (0.5-0.9) | 7 | 8 | 13 | 16 | 17 | 15 |
| Grade 4 (<0.5) | 0 | 1 | 0 | 0 | 1 | 0 |

Abbreviations: ALT—alanine aminotransferase; AST—aspartate aminotransferase; BID—twice daily; QD—once daily; ULN—upper limit of normal.

As can be seen from these results, the safety and tolerability profile of Compound 1 was acceptable across doses.

Figure 10:
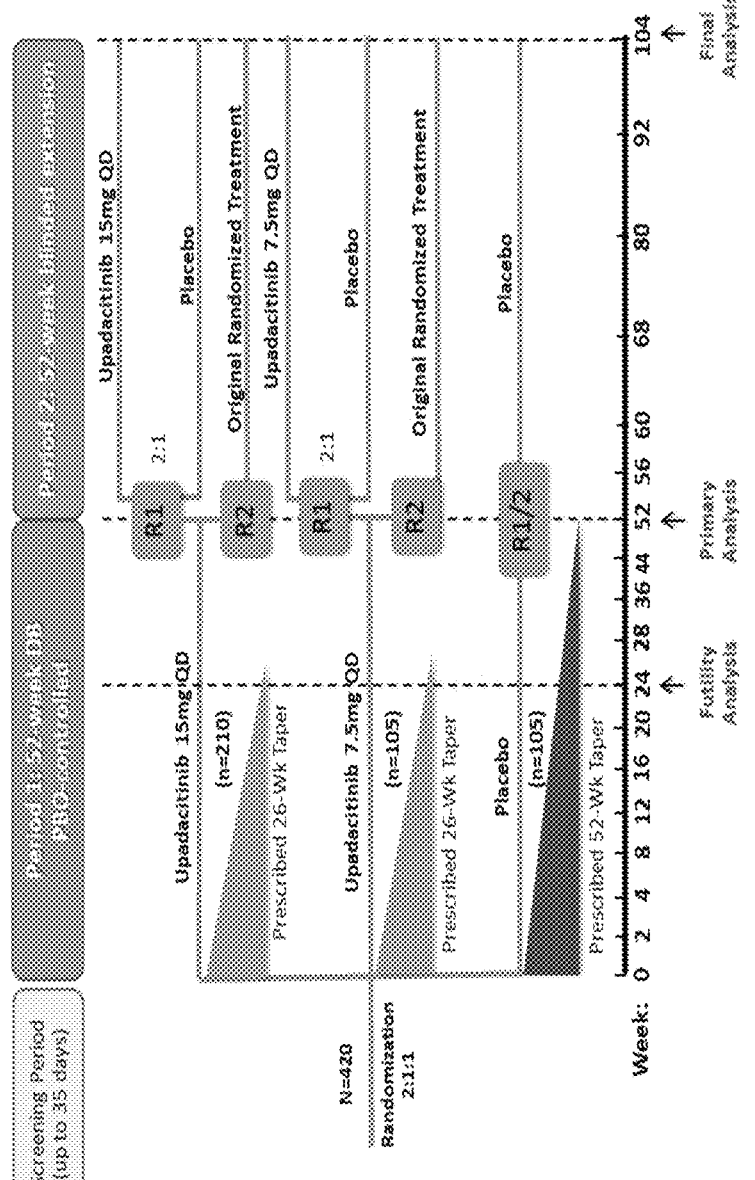
FIG. 10 is a schematic illustration of a clinical study according to a non-limiting embodiment of the disclosure, as described in Example 34.
Figure 11:
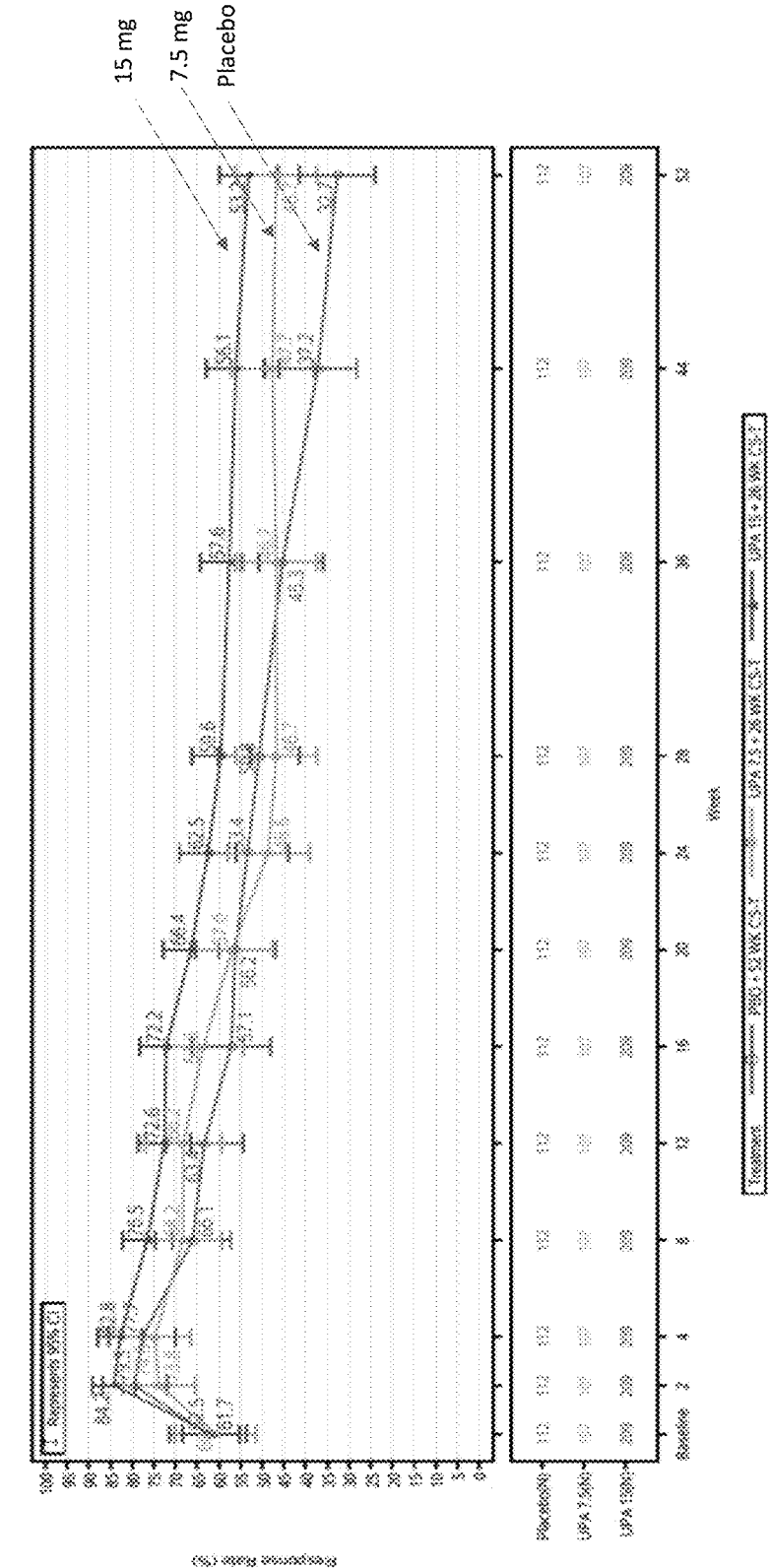
FIG. 11 is a graphical depiction of efficacy over time according to the primary endpoint of sustained remission in the clinical study of Example 34.
Figure 12:
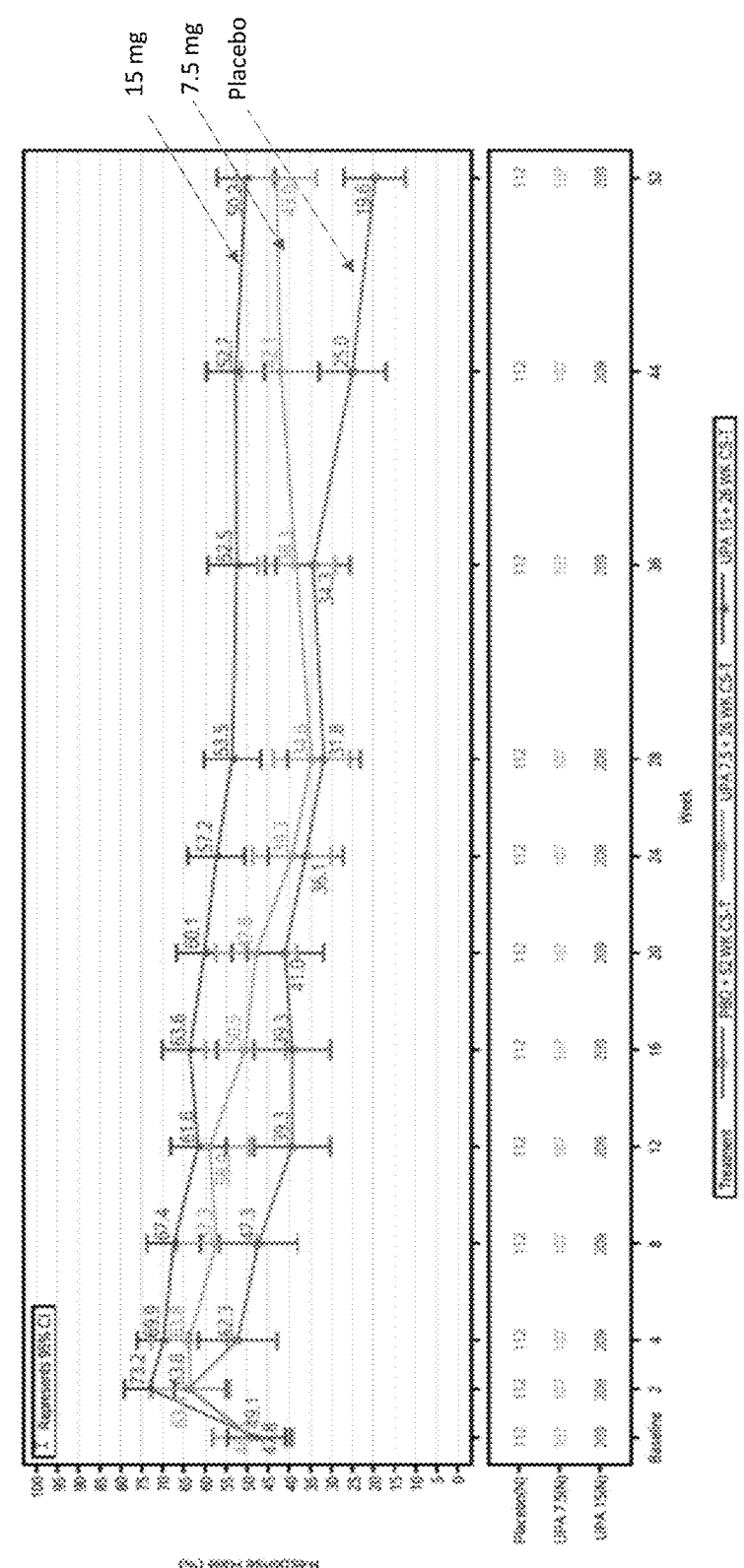
FIG. 12 is a graphical depiction of efficacy over time according to the secondary endpoint of sustained complete remission in the clinical study of Example 34.

Example 34: A Multicenter, Randomized, Double-Blind, Placebo-Controlled Study to Evaluate the Safety and Efficacy of Upadacitinib in Subjects with Giant Cell Arteritis This was a Phase 3, three-arm, two-period study to evaluate the efficacy, safety, and tolerability of upadacitinib in subjects with Giant Cell Arteritis (GCA) who were 50 years of age or older. The study included a 35-day maximum screening period, a 52-week randomized, double-blind, PBO-controlled treatment period (Period 1), a 52-week blinded extension period in which subjects were either re-randomized or continued their original treatment assignment (Period 2), and a 30-day follow-up period. The objective of the first period was to evaluate the efficacy of upadacitinib in combination with a 26-week corticosteroid (CS) taper regimen compared to placebo in combination with a 52-week CS taper regimen, as measured by the proportion of participants in sustained remission at Week 52, and to assess the safety and tolerability of upadacitinib in participants with giant cell arteritis (GCA). The objective of the second period was to evaluate the safety and efficacy of continuing versus withdrawing upadacitinib in maintaining remission in participants who achieved sustained remission in Period 1. A schematic of the study is shown in FIG. 10. Each arm of the study is described below in Table 20.

TABLE 20

Treatment Groups

| Participant Group/Arm | Intervention/Treatment |
| --- | --- |
| Experimental: Arm A Upadacitinib dose A administered daily + 26-week CS taper regimen | Drug: Oral Upadacitinib Drug: Oral Corticosteroid (CS) |
| Experimental: Arm B Upadacitinib dose B administered daily + 26-week CS taper regimen | Drug: Oral Upadacitinib Drug: Oral Corticosteroid (CS) |
| Placebo Comparator: Arm C Placebo administered daily + 52-week CS taper regimen | Drug: Oral Corticosteroid (CS) Other: Oral Placebo It will be administered orally. |

In Period 1, a total of 428 subjects were randomized in a 2:1:1 ratio at Baseline to upadacitinib 15 mg once daily (QD), upadacitinib 7.5 mg QD, and placebo (PBO) QD treatment groups, and dosed, where the upadacitinib 15 mg and 7.5 mg treatment groups were required to complete a mandatory 26-week corticosteroid (CS) taper, and the PBO group were required to complete a mandatory 52-week CS taper. At the end of Period 1 (Week 52 visit), subjects who achieved sustained remission for at least 24 consecutive weeks prior to Week 52 visit were re-randomized in 2:1 ratio to either continue on the same upadacitinib treatment group or switch to PBO if subject was on a upadacitinib treatment group in Period 1; or continued to receive PBO if subject was on PBO group in Period 1. Subjects who had absence of GCA signs and symptoms AND were CS-free at Week 52 visit but did not meet the sustained remission criteria for at least 24 consecutive weeks prior to Week 52 visit continued in Period 2 on their originally randomized treatment assignment in Period 1. All other subjects were discontinued from study drug and study at the end of Period 1.

Inclusion Criteria
    Inclusion criteria were as follows:
    Diagnosis of giant cell arteritis (GCA) according to the following criteria:
        History of erythrocyte sedimentation rate (ESR)$>=50$ mm/hour or high sensitivity C-reactive protein (hsCRP)/CRP $>=1.0$ mg/dL
        Presence of at least one of the following: Unequivocal cranial symptoms of GCA or Unequivocal symptoms of polymyalgia rheumatica (PMR)
        Presence of at least one of the following: temporal artery biopsy revealing features of GCA or evidence of large vessel vasculitis by angiography or cross-sectional imaging such as ultrasound, magnetic resonance imaging (MRI), computed tomography (CT) or positron emission tomography (PET).
    Active GCA, either new onset or relapsing, within 8 weeks of Baseline.
    Clinically stable CGA to allow the participant to safely initiate the corticosteroid (CS) taper regimen in Table 20.
    Participants must have received treatment with $>=40$ mg prednisone (or equivalent) at any time prior to Baseline and be receiving prednisone (or equivalent)$>=20$ mg once daily (QD) at Baseline.
Exclusion Criteria
    Exclusion criteria were as follows:
    Prior exposure to any Janus Kinase (JAK) inhibitor.
    Treatment with an interleukin-6 (IL-6) inhibitor within 4 weeks of study start, or prior treatment with an IL-6 inhibitor and experienced a disease flare during treatment.
    Use of any of the following systemic immunosuppressant treatments within the specified timeframe prior to study start:
        Anakinra within 1 week of study start;
        Methotrexate, hydroxychloroquine, cyclosporine, azathioprine, or mycophenolate within 4 weeks of study start;
        Oral corticosteroid (CS) for conditions other than GCA within 4 weeks of study start, or intravenous CS within 4 weeks of study start;
        Greater than or equal to 8 weeks for leflunomide if no elimination procedure was followed, or adhere to an elimination procedure;
        Cell-depleting agents or alkylating agents including cyclophosphamide within 6 months of study start;
        Current or past history of infection including herpes zoster or herpes simplex, human immunodeficiency virus (HIV), active Tuberculosis, active or chronic recurring infection, active hepatitis B or C.
Primary Outcome Measure
    The primary outcome measure was the percentage of participants achieving sustained remission from Week 12 through Week 52. Sustained remission was defined as having achieved absence of GCA signs and symptoms and adherence to the corticosteroid (CS) taper regimen in Table 20.
Secondary and Other Outcome Measures
    The secondary outcome measure was the percentage of participants achieving sustained complete remission. Sustained complete remission was defined as having absence of GCA signs and symptoms; normalization of erythrocyte sedimentation rate (ESR); Normalization of high sensitivity C-reactive protein (hs-CRP), and adherence to the CS taper regimen in Table 20. Other outcome measures included:
        Cumulative Corticosteroid (CS) exposure. The cumulative exposure to corticosteroid(s) was assessed.

Time to First Disease Flare. Disease flare was defined as an event determined by the investigator to represent recurrence of GCA signs or symptoms or an ESR measurement >30 mm/hr (attributable to GCA) AND requiring an increase in CS dose.

Number of Disease Flares per Participant. The number of disease flares per participant during Period 1 was assessed.

Percentage of Participants Who Experience at Least 1 Disease Flare. The percentage of participants who experienced at least 1 disease flare was assessed.

Percentage of Participants in Complete Remission. Complete remission was defined as having achieved absence of GCA signs and symptoms; normalization of ESR; normalization of hs-CRP and adherence to the CS taper regimen in Table 20.

Change from Baseline in the 36-item Short Form Quality of Life Questionnaire (SF-36) Physical Component Score (PCS).

Change from Baseline in Functional Assessment of Chronic Illness Therapy-Fatigue (FACIT-Fatigue).

Assessment of Treatment Satisfaction Questionnaire for Medication (TSQM) Patient Global Satisfaction Subscale.

Rate of CS-related Adverse Events. The rate of CS-related adverse events was assessed.

Results

Demographic, Baseline Characteristics, and Subject Disposition

A total of 428 subjects were randomized and dosed (112 in PBO, 107 in upadacitinib 7.5 mg and 209 in upadacitinib 15 mg). In Period 1, 299 (69.9%) subjects completed study drug (Table 21). The rate of premature discontinuation from study drug was higher in the PBO group (36.6%) than in the upadacitinib 7.5 mg (31.8%) and upadacitinib 15 mg (25.8%) groups. The most common reason for study drug premature discontinuation was due to adverse event, followed by lack of efficacy. Demographics and baseline characteristics were generally balanced among treatment groups (Table 22).

TABLE 21

| Subject Disposition in the Period 1 (Population: Full Analysis Set 1 (FAS1)) | | | | |
| --- | --- | --- | --- | --- |
| Subject Disposition | PBO + 52 WK CS Taper (N = 112) n (%) | UPA 7.5 MG + 26 WK CS Taper (N = 107) n (%) | UPA 15 MG + 26 WK CS Taper (N = 209) n (%) | Total (N = 428) n (%) |
| Randomized and dosed | 112 (100) | 107 (100) | 209 (100) | 428 (100) |
| Completed Study Drug in Period 1 | 71 (63.4) | 73 (68.2) | 155 (74.2) | 299 (69.9) |
| Prematurely Discontinued Study Drug in Period 1 (Primary Reasons) | 41 (36.6) | 34 (31.8) | 54 (25.8) | 129 (30.1) |
| Adverse Event | 23 (20.5) | 18 (16.8) | 32 (15.3) | 73 (17.1) |
| Withdrew Consent | 3 (2.7) | 7 (6.5) | 8 (3.8) | 18 (4.2) |
| Lost to Follow-Up | 0 | 0 | 0 | 0 |
| Lack of Efficacy | 8 (7.1) | 4 (3.7) | 7 (3.3) | 19 (4.4) |
| COVID-19 Infection | 0 | 0 | 0 | 0 |
| COVID-19 Logistical Restrictions | 1 (0.9) | 0 | 0 | 1 (0.2) |
| Other | 6 (5.4) | 5 (4.7) | 7 (3.3) | 18 (4.2) |

TABLE 22

| Demographics and Baseline Disease Characteristics (Population: FAS1) | | | |
| --- | --- | --- | --- |
| Demographic and Baseline Characteristics | PBO + 52 WK CS Taper (N = 112) | UPA 7.5 MG + 26 WK CS Taper (N = 107) | UPA 15 MG + 26 WK CS Taper (N = 209) |
| Female, n (%) | 77 (68.8) | 80 (74.8) | 156 (74.6) |
| Age (years), Mean (Range) | 71.6 (52-87) | 71.1 (54-88) | 70.8 (51-88) |
| Age group (years), n (%) | 95 (84.8) | 88 (82.2) | 167 (79.9) |
| ≥65 | 36 (32.1) | 39 (36.4) | 65 (31.1) |
| ≥75 | | | |
| Weight (kg), Mean (SD) | 71.1 (16.03) | 67.9 (15.66) | 69.0 (15.95) |
| Prior Use of IL-6 Inhibitor = Yes, n (%) | 7 (6.3) | 7 (6.5) | 9 (4.3) |
| Baseline CS Dose, n (%) >30 mg | 53 (47.3) | 52 (48.6) | 99 (47.4) |
| New Onset of GCA = Yes, n (%) | 76 (67.9) | 75 (70.1) | 148 (70.8) |

TABLE 22-continued

| Demographics and Baseline Disease Characteristics (Population: FAS1) | | | |
|---|---|---|---|
| Demographic and Baseline Characteristics | PBO + 52 WK CS Taper (N = 112) | UPA 7.5 MG + 26 WK CS Taper (N = 107) | UPA 15 MG + 26 WK CS Taper (N = 209) |
| duration since diagnosis (days), Mean (SD) New Onset Disease Relapsing Disease | 38.2 (14.79) 665.7 (816.30) | 35.7 (11.06) 999.2 (1179.02) | 39.5 (28.13) 664.9 (687.54) |
| Baseline ESR (mm/hr), Mean (SD) | 21.7 (25.51) | 19.9 (21.10) | 19.5 (17.46) |
| Baseline hsCRP (mg/dL), Mean (SD) | 5.7 (9.53) | 6.0 (9.42) | 6.7 (12.71) |

Efficacy

Primary and Secondary Efficacy Endpoints

The primary endpoint and secondary endpoints were tested for each upadacitinib treatment group (15 mg or 7.5 mg) vs. placebo. Graphical depictions of efficacy are provided in FIGS. 11, 12, 13A, 13B, 14A, 14B, 15, and 16. Based on the alpha-spending approach, upadacitinib 15 mg met the primary endpoint (sustained remission from Week 12 through Week 52; upadacitinib 15 mg: 46.4% vs. PBO: 29.0%, p=0.0019). Upadacitinib 15 mg also achieved 9 of the 11 secondary endpoints (Table 23). Numerically better efficacy was observed in the upadacitinib 7.5 mg treatment group; however, none of the endpoints achieved statistical significance (Table 23). Under type-I error control using the graphical approach for Japan PMDA, upadacitinib 15 mg met the primary endpoint but did not achieve any of the secondary endpoints (Table 24). Upadacitinib 7.5 mg did not meet the primary or any of the secondary endpoints. The efficacy of upadacitinib 15 mg was in general consistent across pre-specified subgroups, with treatment differences in favor of upadacitinib 15 mg.

TABLE 23

| Overview of Primary and Secondary Endpoints under type-I error control for global except PMDA (Population: FAS1) | | | | | |
|---|---|---|---|---|---|
| | Estimate* | Estimate* Placebo-Adj. Diff[&] | | p-value vs. PBO | |
| Endpoints | PBO + 52 WK CS Taper (N = 112) | UPA 7.5 MG + 26 WK CS Taper (N = 107) | UPA 15 MG + 26 WK CS Taper (N = 209) | UPA 7.5 MG + 26 WK CS Taper (N = 107) | UPA 15 MG + 26 WK CS Taper (N = 209) |
| Primary Endpoint | | | | | |
| Sustained remission from Week 12 through Week 52, n (%) | 33 (29.0) | 44 (41.1) $\Delta$ = 12.1 | 97 (46.4) $\Delta$ = 17.1 | 0.0579[NS] | 0.0019[S] |
| Secondary Endpoints | | | | | |
| Sustained complete remission from Week 12 through Week 52, n (%) | 18 (16.1) | 28 (26.2) $\Delta$ = 9.9 | 78 (37.1) $\Delta$ = 20.7 | 0.0699[NS] | <0.0001[S] |
| Cumulative CS exposure through Week 52, Median (mg) | (N = 90) 2882.0 | (N = 86) 1905.0 — | (N = 180) 1615.0 — | <0.0001[NS] | <0.0001[S] |
| Time to first disease flare through Week 52, Median (days) | 323.0 | — HR = 0.75 | — HR = 0.57 | 0.1778[NS] | 0.0025[S] |
| Experience at least 1 disease flare through Week 52, % | 55.6 | 41.3 OR = 0.60 | 34.3 OR = 0.47 | 0.0633[NS] | 0.0014[S] |
| Complete remission at Week 52, n (%) | 22 (19.6) | 46 (43.0) $\Delta$ = 23.5 | 105 (50.2) $\Delta$ = 30.3 | <0.0001[NS] | <0.0001[S] |
| Complete remission at Week 24, n (%) | 40 (36.1) | 42 (39.3) $\Delta$ = 3.2 | 120 (57.2) $\Delta$ = 20.8 | 0.6276[NS] | 0.0002[S] |
| Change from Baseline in the SF-36 PCS at Week 52, LS Mean (SE) | (N = 44) −1.2892 (1.0260) | (N = 49) 1.3202 (1.0032) $\Delta$ = 2.6094 | (N = 123) 2.4634 (0.6565) $\Delta$ = 3.7526 | 0.0670[NS] | 0.0019[S] |
| Number of disease flares per subject through Week 52 | 0.7 | 0.6 RR = 0.8 | 0.4 RR = 0.6 | 0.2722[NS] | 0.0010[S] |
| Change from Baseline in FACIT-Fatigue at Week 52, LS Mean (SE) | (N = 45) −2.4 (1.18) | (N = 49) 1.1 (1.15) $\Delta$ = 3.5 | (N = 123) 1.7 (0.75) $\Delta$ = 4.0 | 0.0338[NS] | 0.0036[S] |
| Assessment of TSQM patient global satisfaction subscale at Week 52, LS Mean (SE) | (N = 45) 68.8428 (2.5462) | (N = 52) 74.2644 (2.4463) $\Delta$ = 5.4216 | (N = 126) 71.5753 (1.6448) $\Delta$ = 2.7325 | 0.1203[NS] | 0.3573[NS] |

TABLE 23-continued

Overview of Primary and Secondary Endpoints under type-I error control for global except PMDA (Population: FAS1)

| | Estimate* | Estimate* Placebo-Adj. Diff[&] | | p-value vs. PBO | |
|---|---|---|---|---|---|
| Endpoints | PBO + 52 WK CS Taper (N = 112) | UPA 7.5 MG + 26 WK CS Taper (N = 107) | UPA 15 MG + 26 WK CS Taper (N = 209) | UPA 7.5 MG + 26 WK CS Taper (N = 107) | UPA 15 MG + 26 WK CS Taper (N = 209) |
| Rate of CS-related AEs through Week 52 | 1.7 | 1.7 RR = 0.9 | 2.0 RR = 1.1 | 0.7749[NS] | 0.4371[NS] |

[&]Diff: stratum-adjusted treatment difference; HR: hazard ratio; OR: odds ratio; RR: rate ratio.

*Percentage for categorical endpoints, least squares mean for continuous endpoints (except for cumulative CS exposure), median for cumulative CS exposure and time to first disease flare, and mean number of events per subject per patient-year for number of disease flares and rate of CS-related AEs.
[S/NS]Achieved/not achieved statistical significance according to the pre-specified testing strategy for overall type-I error control.

TABLE 24

Overview of Primary and Secondary Endpoints under Type-I Error Control for PMDA (Population: FAS1)

| | Estimate* PBO + 52 | Estimate* Placebo-Adj. Diff[&] | | p-value vs. PBO | |
|---|---|---|---|---|---|
| Endpoints | WK CS Taper (N = 112) | UPA 7.5 MG + 26 WK CS Taper (N = 107) | UPA 15 MG + 26 WK CS Taper (N = 209) | UPA 7.5 MG + 26 WK CS Taper (N = 107) | UPA 15 MG + 26 WK CS Taper (N = 209) |
| Primary Endpoint | | | | | |
| Sustained remission from Week 12 through Week 52, n (%) | 33 (29.0) | 44 (41.1) Δ = 12.1 | 97 (46.4) Δ = 17.1 | 0.0579[NS] | 0.0019[S] |
| Secondary Endpoints | | | | | |
| Sustained complete remission from Week 12 through Week 52, n (%) | 18 (16.1) | 28 (26.2) Δ = 9.9 | 78 (37.1) Δ = 20.7 | 0.0699[NS] | <0.0001[NS] |
| Cumulative CS exposure through Week 52, Median (mg) | (N = 90) 2882.0 | (N = 86) 1905.0 — | (N = 180) 1615.0 — | <0.0001[NS] | <0.0001[NS] |
| Time to first disease flare through Week 52, Median (days) | 323.0 | — HR = 0.75 | — HR = 0.57 | 0.1778[NS] | 0.0025[NS] |
| Experience at least 1 disease flare through Week 52, % | 55.6 | 41.3 OR = 0.60 | 34.3 OR = 0.47 | 0.0633[NS] | 0.0014[NS] |
| Complete remission at Week 52, n (%) | 22 (19.6) | 46 (43.0) Δ = 23.5 | 105 (50.2) Δ = 30.3 | <0.0001[NS] | <0.0001[NS] |
| Complete remission at Week 24, n (%) | 40 (36.1) | 42 (39.3) Δ = 3.2 | 120 (57.2) Δ = 20.8 | 0.6276[NS] | 0.0002[NS] |
| Change from Baseline in the SF-36 PCS at Week 52, LS Mean (SE) | (N = 44) −1.2892 (1.0260) | (N = 49) 1.3202 (1.0032) Δ = 2.6094 | (N = 123) 2.4634 (0.6565) Δ = 3.7526 | 0.0670[NS] | 0.0019[NS] |
| Number of disease flares per subject through Week 52 | 0.7 | 0.6 RR = 0.8 | 0.4 RR = 0.6 | 0.2722[NS] | 0.0010[NS] |
| Change from Baseline in FACIT-Fatigue at Week 52, LS Mean (SE) | (N = 45) −2.4 (1.18) | (N = 49) 1.1 (1.15) Δ = 3.5 | (N = 123) 1.7 (0.75) Δ = 4.0 | 0.0338[NS] | 0.0036[NS] |
| Assessment of TSQM patient global satisfaction subscale at Week 52, LS Mean (SE) | (N = 45) 68.8428 (2.5462) | (N = 52) 74.2644 (2.4463) Δ = 5.4216 | (N = 126) 71.5753 (1.6448) Δ = 2.7325 | 0.1203[NS] | 0.3573[NS] |

TABLE 24-continued

Overview of Primary and Secondary Endpoints under Type-I Error Control for PMDA (Population: FAS1)

| | Estimate* PBO + 52 | Estimate* Placebo-Adj. Diff[&] | | p-value vs. PBO | |
| --- | --- | --- | --- | --- | --- |
| Endpoints | WK CS Taper (N = 112) | UPA 7.5 MG + 26 WK CS Taper (N = 107) | UPA 15 MG + 26 WK CS Taper (N = 209) | UPA 7.5 MG + 26 WK CS Taper (N = 107) | UPA 15 MG + 26 WK CS Taper (N = 209) |
| Rate of CS-related AEs through Week 52 | 1.7 | 1.7 RR = 0.9 | 2.0 RR = 1.1 | 0.7749[NS] | 0.4371[NS] |

[&]Diff: stratum-adjusted treatment difference; HR: hazard ratio; OR: odds ratio; RR: rate ratio.

Pharmacokinetics and Preliminary Exposure-Response Analyses for Efficacy

Pharmacokinetics

The pharmacokinetics of upadacitinib in subjects with GCA were consistent with prior assessments in subjects with rheumatoid arthritis (RA). The median upadacitinib average plasma concentration for the 7.5 mg and 15 mg treatment groups were 7.9 ng/ml and 15.7 ng/ml, respectively.

Preliminary Exposure-Response Analyses for Efficacy

Figures 13A, 13B:
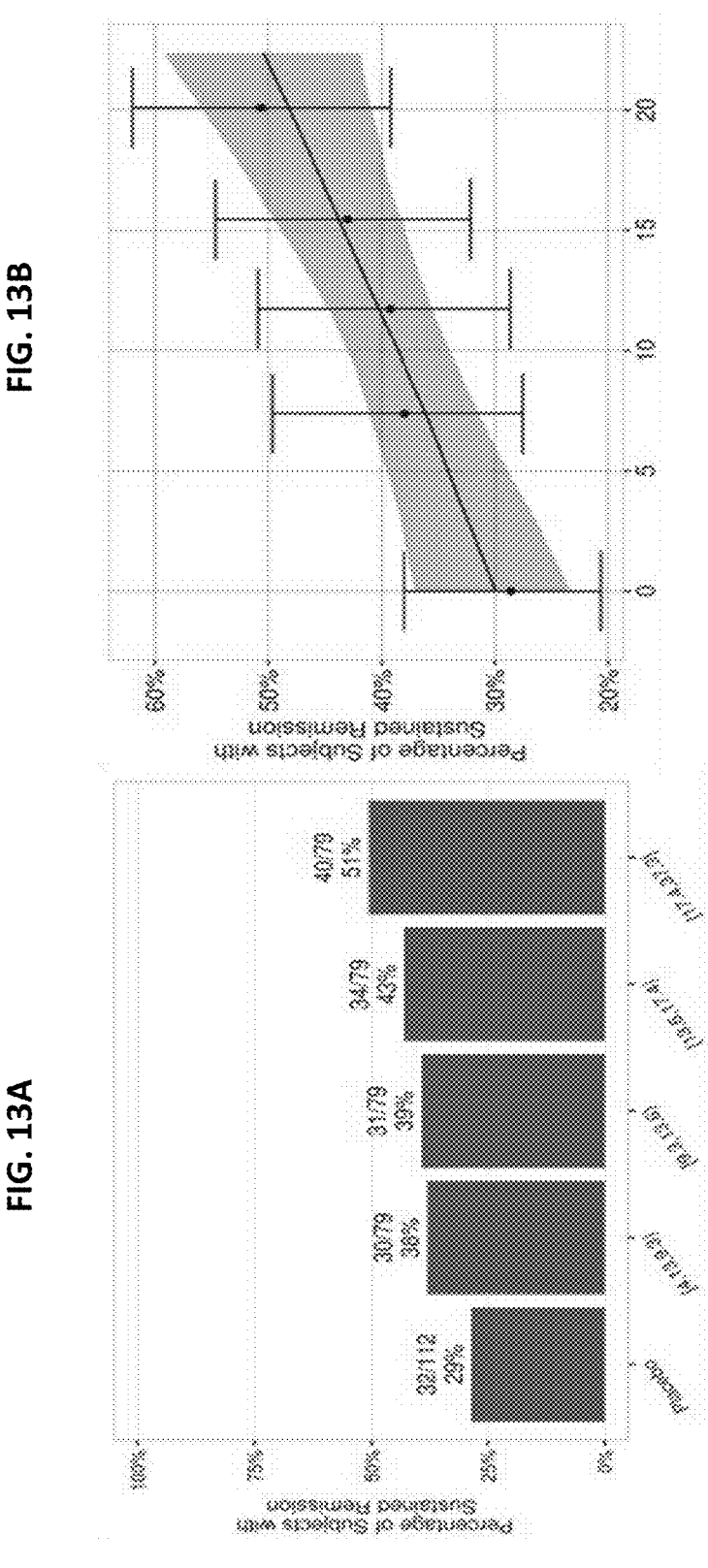
FIG. 13A is a graphical depiction of the proportion of patients achieving sustained remission from week 12 to week 52 in the clinical study of Example 34 (Quartile plot).
FIG. 13B is a graphical depiction of the proportion of patients achieving sustained remission from week 12 to week 52 in the clinical study of Example 34 (Logistic regression model).
Figure 15:
FIG. 15 is a graphical depiction of cumulative exposure through week 52 in the clinical study of Example 34.
Figure 16:
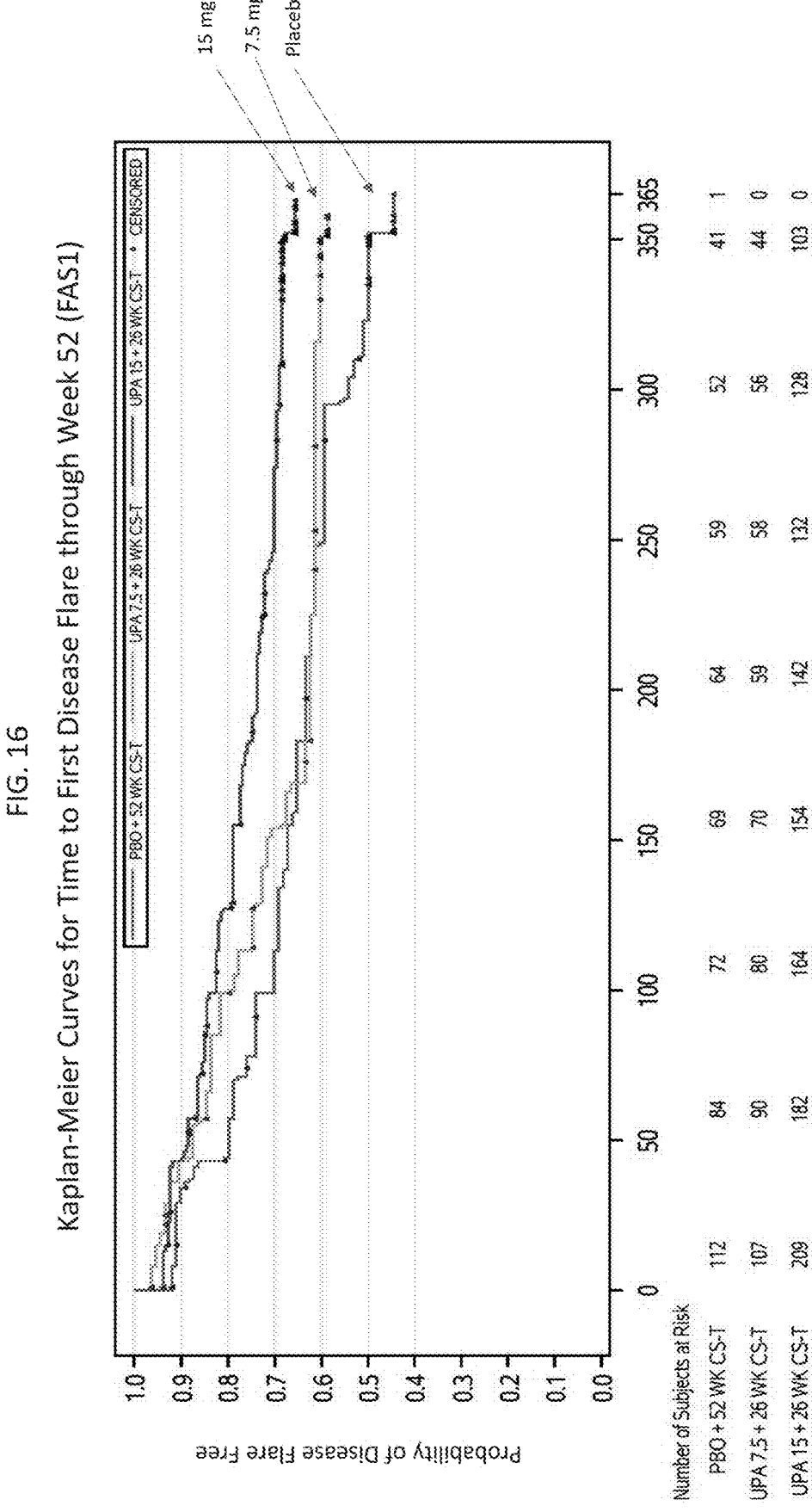
FIG. 16 is a graphical depiction of time to first disease flare through week 52 in the clinical study of Example 34.

There was a clear trend for increase in response for both sustained remission and sustained complete remission from Week 12 through Week 52 with increasing upadacitinib plasma exposures, with the highest response observed in the highest quartile of exposures (FIGS. 13A and 14A). A linear model with a clear exposure-response relationship (nominal $p<0.01$) was selected as the optimal model to describe both endpoints (FIGS. 13B and 14B). Simulations based on the logistic regression models showed that upadacitinib 15 mg is predicted to provide 9% and 10% higher efficacy compared to upadacitinib 7.5 mg for sustained remission and sustained complete remission, respectively.

Safety

Both upadacitinib treatment groups were generally safe and well-tolerated in subjects with GCA. No new safety signals were identified with upadacitinib 7.5 mg and 15 mg treatment groups in this GCA population as compared to the safety profile of upadacitinib in previously approved indications. It is notable that no new safety signals were identified with upadacitinib in this trial, which was comprised of an elderly patient population on high dose steroids at Baseline (~50%>30 mg/day) and at higher risk for multiple complications, including but not limited to, major cardiovascular events, malignancy, serious infections, etc. Based upon the overall positive benefit and risk assessment, orally administered upadacitinib 15 mg effectively treated GCA, which is a disease with a high unmet need.

What is claimed is:

1. A method of treating inflammation of the aorta in a human patient in need thereof, comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg.

2. The method of claim 1, wherein the patient is an adult.

3. The method of claim 2, wherein the patient had inadequately responded to treatment with oral corticosteroids.

4. The method of claim 2, wherein the method further comprises administering an oral corticosteroid to the patient.

5. The method of claim 3, wherein the method further comprises administering an oral corticosteroid to the patient.

6. The method of claim 1, wherein the therapeutically effective amount of Compound 1 is administered as 15.4 mg of Freebase Hydrate Form C.

7. A method of treating giant cell arteritis (GCA) in a patient in need thereof, the method comprising orally administering once daily to the patient 15 mg of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the patient achieves remission of GCA 12 weeks following the first daily administration.

8. The method of claim 7, wherein the patient achieves sustained remission of GCA from 12 weeks following the first daily administration through 52 weeks following the first daily administration.

9. The method of claim 7, wherein the patient achieves complete remission of GCA 12 weeks following the first daily administration.

10. The method of claim 9, wherein the patient achieves sustained complete remission of GCA from 12 weeks following the first daily administration through 52 weeks following the first daily administration.

11. A method of inducing remission of giant cell arteritis (GCA) in a patient in need thereof, the method comprising orally administering once daily to the patient 15 mg of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the patient achieves remission of GCA 12 weeks following the first daily administration.

12. The method of claim 11, wherein the patient achieves complete remission of GCA 12 weeks following the first daily administration.

13. A method of inducing and sustaining remission of giant cell arteritis (GCA) in a patient in need thereof, the method comprising orally administering once daily to the patient 15 mg of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the patient achieves sustained remission of GCA from 12 weeks following the first daily administration through 52 weeks following the first daily administration.

14. The method of claim 13, wherein the patient achieves complete remission of GCA 12 weeks following the first daily administration.

15. The method of claim 14, wherein the patient achieves sustained complete remission of GCA from 12 weeks following the first daily administration through 52 weeks following the first daily administration.

* * * * *